US009249226B2

(12) United States Patent
de Weers et al.

(10) Patent No.: US 9,249,226 B2
(45) Date of Patent: Feb. 2, 2016

(54) ANTIBODIES AGAINST HUMAN CD38

(75) Inventors: Michel de Weers, Houten (NL); Tim Walseth, Roseville, MN (US); Jan van de Winkel, Zeist (NL); Tom Vink, Alphen a/d Rijn (NL); Paul Parren, Odijk (NL)

(73) Assignee: GENMAB A/S, Copenhagen (DK)

( * ) Notice: Subject to any disclaimer, the term of this patent is extended or adjusted under 35 U.S.C. 154(b) by 169 days.

(21) Appl. No.: 13/702,857

(22) PCT Filed: Jun. 8, 2011

(86) PCT No.: PCT/EP2011/059507
§ 371 (c)(1),
(2), (4) Date: Dec. 17, 2012

(87) PCT Pub. No.: WO2011/154453
PCT Pub. Date: Dec. 15, 2011

(65) Prior Publication Data
US 2013/0209355 A1    Aug. 15, 2013

Related U.S. Application Data

(60) Provisional application No. 61/353,082, filed on Jun. 9, 2010.

(30) Foreign Application Priority Data

Jun. 9, 2010  (DK) .................................. 2010 00498

(51) Int. Cl.
| C07K 16/30 | (2006.01) |
|---|---|
| C07K 16/28 | (2006.01) |
| A61K 39/395 | (2006.01) |
| A61K 45/06 | (2006.01) |

(52) U.S. Cl.
CPC ......... *C07K 16/2896* (2013.01); *A61K 39/3955* (2013.01); *A61K 45/06* (2013.01); *C07K 2317/21* (2013.01); *C07K 2317/34* (2013.01); *C07K 2317/565* (2013.01); *C07K 2317/732* (2013.01); *C07K 2317/75* (2013.01); *C07K 2317/76* (2013.01)

(58) Field of Classification Search
CPC ........... C07K 16/2896; C07K 2317/21; C07K 2317/24
See application file for complete search history.

(56) References Cited

U.S. PATENT DOCUMENTS

| 5,618,920 | A | 4/1997 | Robinson et al. | |
|---|---|---|---|---|
| 6,171,586 | B1 | 1/2001 | Lam et al. | |
| 6,455,043 | B1 | 9/2002 | Grillo-Lopez | |
| 7,109,304 | B2 | 9/2006 | Hansen et al. | |
| 7,829,673 | B2 * | 11/2010 | De Weers et al. | 530/387.1 |
| 2004/0019915 | A1 | 1/2004 | Challita-Eid et al. | |
| 2004/0141982 | A1 | 7/2004 | Lust et al. | |
| 2004/0167319 | A1 | 8/2004 | Teeling et al. | |
| 2005/0037969 | A1 | 2/2005 | Lu et al. | |
| 2005/0266008 | A1 | 12/2005 | Graziano et al. | |
| 2006/0019303 | A1 | 1/2006 | Castle et al. | |
| 2007/0218060 | A1 | 9/2007 | Long et al. | |
| 2009/0076249 | A1 | 3/2009 | De Weers et al. | |
| 2010/0285004 | A1 | 11/2010 | Tesar et al. | |

FOREIGN PATENT DOCUMENTS

| WO | 89/08114 | A1 | 9/1989 |
|---|---|---|---|
| WO | 92/01049 | A2 | 1/1992 |
| WO | 94/17184 | A1 | 8/1994 |
| WO | 96/16990 | A1 | 6/1996 |
| WO | 98/16245 | A1 | 4/1998 |
| WO | 98/16254 | A1 | 4/1998 |
| WO | 98/50435 | A1 | 11/1998 |
| WO | 99/62526 | A2 | 12/1999 |
| WO | 00/06194 | A2 | 2/2000 |
| WO | 00/40265 | A1 | 7/2000 |
| WO | 02/06347 | A1 | 1/2002 |
| WO | 02/32288 | A2 | 4/2002 |
| WO | 03/080672 | A1 | 10/2003 |
| WO | 2004/019915 | A1 | 3/2004 |
| WO | 2004/035607 | A2 | 4/2004 |
| WO | 2004/045512 | A2 | 6/2004 |
| WO | 2004/058288 | A1 | 7/2004 |
| WO | 2005/042019 | A1 | 5/2005 |
| WO | 2005/044855 | A2 | 5/2005 |
| WO | 2005/103083 | A2 | 11/2005 |
| WO | 2006/088951 | A2 | 8/2006 |
| WO | 2006/099875 | A1 | 9/2006 |
| WO | 2006/125640 | A2 | 11/2006 |
| WO | WO2006/125640 | A2 * | 11/2006 |
| WO | 2008/047242 | A2 | 4/2008 |

OTHER PUBLICATIONS

NCBI NP_001766 for human CD38, lasted updated Jun. 1, 2014.*
Shubinsky & Schlesinger, Immunity 1997; 7:315-24.*
Genmab Post-ASH Seminar, Dec. 2013, pp. 1 and 70-73.*
Deckert et al., Clin. Cancer Res. 2014; 20:4574-83.*
Almagro & Fransson, Frontiers in Bioscience 2008; 13:1619-33.*
PJ Carter, Nat Rev Immunol, 2006; 6:343-357.*
ASH 2014 Abstract #3474, Direct in Vitro Comparison of Daratumumab with Surrogate Analogs of CD38 Antibodies MOR03087, SAR650984 and Ab79, Lammerts van Bueren et al., Oral and Poster Abstracts, Dec. 7, 2014.*
Aarhus, Robert et al., "ADP-ribusyl Cyclase and CD38 Catalyze the Synthesis of a Calcium-mobilizing Metabolite from NADP," The Journal of Biological Chemistry, vol. 270(51):30327-30333 (1995).
Abebanjo, Olugbenga A. et al., "A new function for CD38/ADP-ribosyl cyclase in nuclear ca2+ homeostasis," Nature Cell Biology, vol. 1:409-414 (1999).

(Continued)

*Primary Examiner* — Sheela J Huff
*Assistant Examiner* — Jessica H Roark
(74) *Attorney, Agent, or Firm* — Nelson Mullins Riley & Scarborough LLP; Jane E. Remillard, Esq.; Christopher L. Frank

(57) ABSTRACT

Isolated monoclonal antibodies which bind to human CD38 and related antibody-based compositions and molecules, are disclosed. Also disclosed are pharmaceutical compositions comprising the antibodies and therapeutic and diagnostic methods for using the antibodies.

52 Claims, 20 Drawing Sheets

(56) References Cited

OTHER PUBLICATIONS

Adams, Julian et al., "Proteasome inhibition: a new strategy in cancer treatment," Investigational New Drugs, vol. 18:109-121 (2000).

Antonelli, Alessandro et al., "Human Anti-CD38 Autoantibodies Raise Intracellular Calcium and Stimulate Insulin Release in Human Pancreatic Islets," Diabetes, vol. 50:985-991 (2001).

Ausiello, C.M. et al., "Functional topography of discrete domains of human CD38," Tissue Antigens, vol. 56:539-547 (2000).

Berenbaum, M.C., "Synergy, additivism and antagonism in immunosuppression, A Critical Review," Clin. Exp. Immunol., vol. 28:1-18 (1977).

Boccadoro, Mario et al., "Preclinical evaluation of the proteasome inhibitor bortezomib in cancer therapy," Cancer Cell International, vol. 5(18):1-9 dor 10.1186/1475-2867-5-18 (2005).

Bolognesi, A. et al., "CD38 as a target of IB4 mAb carrying saporin-S6: Design of an immunotoxin for ex vivo depletion of hematological CD38+ neoplasia," Journal of Biological Regulators and Homeostatic Agents, vol. 19:145-152 (2005).

Burgess, Wilson H. et al., "Possible Dissociation of the Heparin-binidng and Mitogenic Activities of Heparin-binding (Acidic Fibroblast Growth Factor-1 from Its Receptor-binding Activities by Site-directed Mutagenesis of a Single Lysine Residue," The Journal of Cell Biology, vol. 111:2129-2138 (1990).

Casset, Florence et al., "A peptide mimetic of an anti-CD4 monoclonal antibody by rational design," Biochemical and Biophysical Research Communications, vol. 307:198-205 (2003).

Cavo, Michele et al., "Superiority of thalidomide and dexamethasone over vincristine-doxorubicin-dexamethasone (VAD) as primary therapy in preparation for autologous transplantation for multiple myeloma," Blood, vol. 106(1):35-39 (2005).

Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).

Chou, Ting-Chao, "Drug Combination Studies and Their Synergy Quantification Using the Chau-Talalay Method," Cancer Res., vol. 70(2):440-446 (2010).

Colman, P.M., "Effects of amino acid sequence changes on anibody-antigen interactions," Research in Immunology, vol. 145:33-36 (1994).

Cotner, Thomas et al., "Human T Cell Proteins Recognized by Rabbit Heteroantisera and Monoclonal Antibodies," Int. J. Immunopharmac., vol. 3(3):255-268 (1981).

Davies, Julian et al., "Affinity improvement of single antibody VH domains: residues in all three hypervariable regions affect antigen binding," Immunotechnology, vol. 2:169-179 (1996).

De Weers, Michel et al., "Daratumumab, a Novel Therapeutic Human CD38 Monoclonal Antibody, Induces Killing of Multiple Myeloma and Other Hematological Tumors," The Journal of Immunology, vol. 186:1840-1848 (2011).

De Weers, M. et al., "Humax-CD38, a New Human CD38 Monoclonal Antibody, Effectively Mediates Killing of Multiple Myeloma and Plasma Cell Leukemia Cells," abstract, submitted for the 16th European Congress of Immunology—ECI2006. Sep. 6-9, 2006—Paris, France.

De Weers, M. et al., "HuMax-CD38, a new human CD38 monoclonal antibody, effectively mediates killing of multiple myeloma and plasma cell leukemia cells," Genmab, 1 page (2006).

De Weers, Michel, "HuMax-CD38," Presentation at the Regional Myeloma Group Meeting (2007).

Donovan, K.A. et al., "Binding and internalization of an antibody engineered ant-CD38 single chain variable fragment (scFv) by human myeloma cells," Blood, vol. 90(10):88A (1997).

Ellis, Jonathan H. et al., "Engineered Anti-CD38 Monoclonal Antibodies for Immunotherapy of Multiple Myeloma" The Journal of Immunology, vol. 155:925-937 (1995).

Ferrero, Enza et al., "Characterization and phylogenetic epitope mapping of CD38 ADPR cyclase in the cynomolgus macaque," BMC Immunology, vol. 5(21):1-13 doi10.1186/1471-2172-5-21 (2004).

Field-Smith, Antonia et al., "Bortezomib (Velcade) in the treatment of multiple myeloma," Therapeutics and Clinical Risk Management, vol. 2(3):271-279 (2006).

Franco, Luisa et al., "The transmembrane glycoprotein CD38 is a catalytically active transporter responsible for generation and influx of the second messenger cyclic ADP-ribose across membranes," FASEB J., vol. 12:1507-1520 (1998).

Funaro, Ada et al., "CD38 Functions Are Regulated Through an Internalization Step," The Journal of Immunology, vol. 160:2238-2247 (1998).

Funaro, Ada et al., "Human CD38: a versatile leukocyte molecule with emerging clinical perspectives," Fundamental and Clinical Immunology, vol. 3(3):101-113 (1995).

Funaro, Ada et al., "Identification and characterization of an active soluble form of human CD38 in normal and pathological fluids," International Immunology, vol. 8(11):1643-1650 (1996).

Funaro, Ada et al., "Involvement of the multilineage CD38 molecule in a unique pathway of cell activation and proliferation," The Journal of Immunology, vol. 145(8):2390-2396 (1990).

Genmab, "Humax-CD38 Effective in Preclinical Studies," retrieved online at /findarticles.com/p/articles/mi_hb5570/is_200512/ai_n24200986 (2005).

Graeff, Richard M. et al., "Enzymatic Synthesis and Characterizations of Cyclic GDP-ribose. A Procedure for Distinguishing Enzymes with ADP-Ribosyl Cyclase Activity," The Journal of Biological Chemistry, vol. 269 (48):30260-30267 (1994).

Green, L.L. et al., "Antigen-specific human monoclonal antibodies from mice engineered with human Ig heavy and light chain YACs," Nature Genetics, vol. 7:13-21 (1994).

Hara-Yokoyama, Miki et al., "Alteration of enzymatic properties of cell-surface antigen CD38 by agonistic anti-CD38 antibodies that prolong B cell survival and induce activation," International Immunopharmacology, vol. 8:59-70 (2008).

Holm, Patrik et al., "Functional mapping and single chain construction of the anti-cytokeratin 8 monoclonal antibody TS1," Molecular Immunology, vol. 44:1075-1084 (2007).

Holt, Lucy J. et al., "Domain antibodies: proteins for therapy," Trends in Biotechnology, vol. 21(11):484-490 (2003).

Hoshino, Shin-ichi et al., "Mapping of the Catalytic and Epitopic Sites of Human CD38/NAD+ Glycohydrolase to a Functional Domain in the Carboxyl Terminus," The Journal of Immunology, vol. 158:741-747 (1997).

Howard, Maureen et al., "Formation and Hydrolysis of Cyclic ADP-Ribose Catalyzed by Lymphocyte Antigen CD38," Science, vol. 262:1056-1059 (1993).

Ikehata, Fumiko et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," J. Clin. Invest., vol. 102(2):395-401 (1998).

Jackson, David G. et al., "Isolation of a cDNA Encoding the Human CD38 (T10) Molecule, a Cell Surface Glycoprotein with an Unusual Discontinuous Pattern of Expression During Lymphocyte Differentiation," The Journal of Immunology, vol. 144(7):2811-2815 (1990).

Jagannath, Sundar, "Multiple Myeloma Update from the American Society of Clinical Oncology (ASCO) 41st Annual Meeting," Update from the American Society of Clinical Oncology (ASCO) 41st Annual Meeting: Poster Sessions, 3 pages (2005).

Johnson, Malisha R. et al., "Primary plasma cell leukemia: morphologic immunophenotypic, and cytogenetic featues of 4 cases treated with chemotherapy and stem cell transplantation," Annals of Diagnostic Pathology, vol. 10:263-268 (2006).

Konopleva, Marina et al., "CD38 in Hematopoietic Malignancies," Human CD38 and Related Molecules.Chem Immunol., vol. 75:189-206 (2000).

Konopleva, Marina et al., "Ligation of Cell Surface CD38 Protein with Agonistic Monoclonal Antibody Induces a Cell Growth Signal in Myeloid Leukemia Cells," The Journal of Immunology, vol. 161:4702-4708 (1998).

Kropff, Martin H. et al., "Bortezomib in combination with dexamethasone for relapsed multiple myeloma," Leukemia Research, vol. 29:587-590 (2005).

(56) References Cited

OTHER PUBLICATIONS

Lande, Roberto et al., "CD38 ligation plays a direct role in the induction of IL-1b, IL-6, and IL-10 secretion in resting human monocytes," Cellular Immunology, vol. 220:30-38 (2002).

Lazar, Eliane et al., "Transforming Growth Factor a: Mutation of Aspartic Acid 47 and Leucine 48 Results in Different Biological Activities," Molecular and Cellular Biology, vol. 8(3):1247-1252 (1988).

Lin, Michael C. et al., "Structure-Function Relationships in Glucagon: Properties of Highly Purified Des-His-, Monoiodo-, and [Des-Asn28, Thr29](homoserine lactone27)-glucagon," Biochemistry, vol. 14(8):1559-1563 (1975).

Lonberg, Nils et al., "Antigen-specific human antibodies from mice comprising four distinct genetic modifications," Nature, vol. 368:856-859 (1994).

MacCallum, Robert M. et al., "Antibody-antigen Interactions: Contact Analysis and Binding Site Topography," J. Mol. Biol., vol. 262:732-745 (1996).

Malavasi, Fabio et al., "Human CD38: a glycoprotein in search of a function," Immunology Today, vol. 15(3):95-97.

Maloney, David G. et al., "Antibody Therapy for Treatment of Multiple Myeloma," Seminars in Hematology, vol. 36(1 Suppl. 3):30-33 (1999).

Mills, Charity et al., "Characterization of Monoclonal Antibodies that Inhibit CD38 ADP-Ribosyl Cyclase Activity," Poster with abstract presented at a student conference at the University of Minnesota (2007).

Mukherjee, Jean et al., "Production and Characterization of Protective Human Antibodies against Shiga Toxin 1," Infection and Immunity, vol. 70(10):5896-5899 (2002).

Orlowski, Robert Z., "The Ubiquitin Proteasome Pathway from Bench to Bedside," American Society of Hematology, pp. 220-225 (2005).

Osterborg, Anders et al., "Natural Interferon-alpha in Combination With Melphalan/Prednisone Versus Melphalan/Prednisone in the Treatment of Multiple Myeloma Stages II and III: A Randomized Study From the Myeloma Group of Central Sweden," Blood, vol. 81(6):1428-1434 (1993).

Padlan, Eduardo A. et al., "Identification of specificity-determining residues in antibodies," Faseb J., vol. 9:133-139 (1995).

Parren, "HuMax-CD38," Conference Proceeding, Presentation for the 23rd International Conference on Advances in the Application of Monoclonal Antibodies in Clinical Oncology, Myconos, Greece (2006).

Parren, "HuMax-CD38," Conference Proceedings, Presentation for the CD38 metting in Torino (2006).

Parren, P.W.H.I. et al., "HuMax-CD38, a new human CD38 monoclonal antibody, effectively mediates killing of multiple myeloma and plasma cell leukemia cells," PWHI Conference Proceeding, Presentation for the CD38 meeting in Torino, Jun. 8-10, 2006.

Paul, William E., "Fv Structure and Diversity in Three Dimensions," Fundamantal Immunology, Third Edition, Raven Press, New York, pp. 292-295 (1993).

Peipp, M. et al., "Fully Human CD38 Antibodies Efficiently Trigger ADCC and CDC of Multiple Myeloma and Plasma Cell Leukemia Cells," Conference Proceedings, Poster Presentation at the 2005 Annual Meeting of the American Society of Hematology, 1 page, Dec. 12, 2005.

Peipp, Matthias et al., "Fully Human CD38 Antibodies Efficiently Trigger ADCC and CDC of Multiple Myeloma Cell Lines and Primary Tumor Cells," Conference Proceedings, Poster presentation of the 2005 Annual Meeting of the American Society of Hematology, 1 page (2005).

Peipp, Matthias et al., AN PREV200600185745, "Fully human CD38 antibodies efficiently trigger ADCC of multiple myeloma cell lines and primary tumor cells," Blood, vol. 106(11):944A, 47th Annual Meeting of the American-Society-of-Hematology (2005).

Rudikoff, Stuart et al., "Single amino acid substitution altering antigen-binding specificity," Proc. Natl. Acad. Sci., USA, vol. 79:1979-1983 (1982).

Schwartz, Gerald P., "A superactive insulin: [B10-Aspartic acid]insulin(human)," Proc. Natl. Acad. Sci. USA, vol. 84:6408-6411 (1987).

Shimazaki, Chihiro, "Advances in the Treatment of Multiple Myeloma—standard early-stage treatment," Medical Practice, vol. 22(8):1395-1398 (2005).

Skolnick, Jeffrey et al., "From genes to protein structure and function: novel applications of computational approaches in the genomic era," TibTech, vol. 18:34-39 (2000).

Stevenson, George T., "CD38 as a Therapeutic Target," Mol. Med., vol. 12(11-12):345-346 (2006).

Takasawa, Shin et al., "Synthesis and Hydrolysis of Cyclic ADP-Ribose by Human Leukocyte Antigen CD38 and Inhibition of the Hydrolysis by ATP," The Journal of Biological Chemistry, vol. 268(35):26052-26054 (1993).

Tamura, Midori et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, vol. 164:1432-1441 (2000).

Terada, Hideo, "What is multiple myeloma?" Modern Physician, vol. 26(5):883-887 (2006).

Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).

Van Der Veer, Michael S. et al., "Towards effective immunotherapy of myeloma: enhanced elimination of myeloma cells by combination of lenalidomide with the human CD38 monoclonal antibody daratumumab," Haematologica, vol. 96(2):284-290 (2011).

Van Spriel, Annemiek B. et al., "Immunotherapeutic perspective for bispecific antibodies," Immunology Today, vol. 21(8):391-397 (2000).

Wiesenthal, "Synergy analysis of 'classic' and newer drug combinations," Human Tumor Assay Journal, retrieved online at: /weisenthal.org/synergy1.htm, 1 page (2012).

Wu, Herren et al., "Humanization of a Murine Monoclonal Antibody by Simultaneous Optimization of Framework and CDR Residues," J. Mol. Biol., vol. 294:151-162 (1999).

Yamashita, Y. et al., "A monoclonal antibody against a murine CD38 homologue delivers a signal to B cells for prolongation of survival and protection against apoptosis in vitro: unresponsiveness of X-linked immunodeficient B cells," Immunology, vol. 85:248-255 (1995).

Zocchi, Elena et al., "A Single Protein Immunologically Identified as CD38 Displays NAD+ Glycohydrolase, ADP-Ribosyl Cyclase and Cyclic ADP-Ribose Hydrolase Activities at the Outer Surface of Human Erythrocytes," Biochemical and Biophysical Research Communications, vol. 196(3):1459-1465 (1993).

Zubiaur, Mercedes et al., "CD38 Ligation Results in Activation of the Raf-1/Mitogen-Activated Protein Kinase and the CD3-z/z-Associated Protein-70 Signaling Pathways in Jurkat T Lymphocytes," The Journal of Immunology, vol. 159:193-205 (1997).

Written Opinion for Application No. PCT/DK2006/000166, dated Sep. 25, 2007.

International Search Report for Application No. PCT/DK2006/000166, dated Aug. 14, 2006.

International Search Report for Application No. PCT/EP20111059507, 6 pages, dated Sep. 6, 2011.

De Weers, M. et al., "HuMax-CD38, a new human CD38 monoclonal antibody, effectively mediates killing of multiple myeloma and plasma cell leukemia cells," Poster presented at the 1st Joint Meeting of European National Societies of Immunology under auspices of EFIS, Sep. 6-9, 2006.

Goldmacher, Victor S. et al., "Anti-CD38-Blocked Ricin: An Immunotoxin for the Treatment of Multiple Myeloma," Blood, vol. 84(9):3017-3025 (1994).

Peng, Kah-Whye et al., "Oncolytic measles viruses displaying a single-chain antibody against CD38, a myeloma cell marker," Blood, vol. 101(7):2557-2562 (2003).

Stevenson, Freda K. et al., "Preliminary Studies for an Immunotherapeutic Approach to the Treatment of Human Myeloma Using Chimeric Anti-CD38 Antibody," Blood, vol. 77(5):1071-1079 (1991).

Vooijs, W.C. et al., "Evaluation of CD38 as Target for Immunotherapy in Multiple Myeloma," Blood, vol. 85 (8):2282-2284 (1995).

* cited by examiner

A)

A) (continued)

B)

B) (continued)

A)

B)

C)

D)

A)

B)

A)

A)

SEQUENCE LISTING

<160> NUMBER OF SEQ ID NOS: 55

<210> SEQ ID NO 1
<211> LENGTH: 363
<212> TYPE: DNA
<213> ORGANISM: homo sapiens

<400> SEQUENCE: 1
caggtccaac tggtgcagtc tggggctgag gtgaagaagc ctgggtcctc ggtgaaggtc      60
tcctgcaagg cttttggagg caccttcagc agctacgcta tcagctgggt gcgacaggcc     120
cctggacaag gcttgagtg gatgggaagg atcatccgtt tccttggtat agcaaactac     180
gcacagaagt tccagggcag agtcacgctt atcgcggaca atccacgaa cacagcctac      240 atggagctga gcagcctgag atctgaggac acggccgttt attactgtgc gggggaacct     300
ggggagcggg accccgatgc tgttgatatc tggggccaag ggacaatggt caccgtctct     360
tca                                                                   363

<210> SEQ ID NO 2
<211> LENGTH: 121
<212> TYPE: PRT
<213> ORGANISM: homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Arg Phe Leu Gly Ile Ala Asn Tyr Ala Gln Lys Phe
    50                  55                  60

Gln Gly Arg Val Thr Leu Ile Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Glu Arg Asp Pro Asp Ala Val Asp Ile Trp Gly
            100                 105                 110

Gln Gly Thr Met Val Thr Val Ser Ser
        115                 120

<210> SEQ ID NO 3
<211> LENGTH: 9
<212> TYPE: PRT
<213> ORGANISM: homo sapiens

<400> SEQUENCE: 3

Gly Gly Thr Ser Phe Ser Ser Tyr Ala
1               5

<210> SEQ ID NO 4
<211> LENGTH: 8
<212> TYPE: PRT
<213> ORGANISM: homo sapiens

<400> SEQUENCE: 4

Ile Ile Arg Phe Leu Gly Ile Ala
1               5

<210> SEQ ID NO 5
<211> LENGTH: 14
<212> TYPE: PRT
<213> ORGANISM: homo sapiens

<400> SEQUENCE: 5

Ala Gly Glu Pro Gly Glu Arg Asp Pro Asp Ala Val Asp Ile
1               5                   10

<210> SEQ ID NO 6
<211> LENGTH: 364
<212> TYPE: DNA
<213> ORGANISM: homo sapiens

<400> SEQUENCE: 6
caggtccaac tggtgcagtc tggggctgag gtgaagaagc ctgggtcctc ggtgaaggtc     60
tcctgcaagg cttttggagg caccttcagc agctatgcta tcagctgggt acgacaggcc    120
cctggacaag gcttgagtg gatgggaagg atcatccgtt ccttggtaa agcaaatcac    180 gcacagaagt tccagggcag agtcacgctt accgcgaca atccacgaa acagcctac    240 atggagctga gcagcctgag atctgaggac acggccgttt attactgtgc ggggaacct    300 ggggatcggg accccgatgc tgttgatatc tggggccaag gacaatggt caccgtctct    360 tcag                                                                 364

<210> SEQ ID NO 7
<211> LENGTH: 121
<212> TYPE: PRT
<213> ORGANISM: homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Arg Phe Leu Gly Lys Ala Asn His Ala Gln Lys Phe
    50                  55                  60

Gln Gly Arg Val Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Asp Arg Asp Pro Asp Ala Val Asp Ile Trp Gly
            100                 105                 110

Gln Gly Thr Met Val Thr Val Ser Ser
        115                 120

<210> SEQ ID NO 8
<211> LENGTH: 8
<212> TYPE: PRT
<213> ORGANISM: homo sapiens

<400> SEQUENCE: 8

Gly Gly Thr Phe Ser Ser Tyr Ala
1               5

<210> SEQ ID NO 9
<211> LENGTH: 8
<212> TYPE: PRT

<213> ORGANISM: homo sapiens

<400> SEQUENCE: 9

Ile Ile Arg Phe Leu Gly Lys Ala
1               5

<210> SEQ ID NO 10
<211> LENGTH: 14
<212> TYPE: PRT
<213> ORGANISM: homo sapiens

<400> SEQUENCE: 10

Ala Gly Glu Pro Gly Asp Arg Asp Pro Asp Ala Val Asp Ile
1               5                   10

<210> SEQ ID NO 11
<211> LENGTH: 364
<212> TYPE: DNA
<213> ORGANISM: homo sapiens

<400> SEQUENCE: 11
caggtccaac tggtgcagtc tggggctgag gtgaagaagc ctgggtcctc ggtgaaggtc    60
tcctgcaagg cttttggagg caccttcagc agttatgcta ttagctgggt gcgacaggcc   120
cctggacaag gcttgagtg gatgggaagg atcatccgtt tccttggtaa aacaaatcac    180
gcacagaagt tccagggcag agtcacactt accgcggaca aatccacgaa cacagcctac   240
atggagctga gcagcctgag atctgaggac acggccgttt attactgtgc gggggaacct   300
ggggatcggg accccgatgc tgttgatatc tggggccaag ggacaatggt caccgtctct   360
tcag                                                                364

<210> SEQ ID NO 12
<211> LENGTH: 121
<212> TYPE: PRT
<213> ORGANISM: homo sapiens

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Arg Phe Leu Gly Lys Thr Asn His Ala Gln Lys Phe
    50                  55                  60

Gln Gly Arg Val Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Pro Gly Asp Arg Asp Pro Asp Ala Val Asp Ile Trp Gly
            100                 105                 110

Gln Gly Thr Met Val Thr Val Ser Ser
        115                 120

<210> SEQ ID NO 13
<211> LENGTH: 8
<212> TYPE: PRT
<213> ORGANISM: homo sapiens

<400> SEQUENCE: 13

Gly Gly Thr Phe Ser Ser Tyr Ala
1               5

<210> SEQ ID NO 14
<211> LENGTH: 8
<212> TYPE: PRT
<213> ORGANISM: homo sapiens

<400> SEQUENCE: 14

Ile Ile Arg Phe Leu Gly Lys Thr
1               5

<210> SEQ ID NO 15
<211> LENGTH: 14
<212> TYPE: PRT
<213> ORGANISM: homo sapiens

<400> SEQUENCE: 15

Ala Gly Glu Pro Gly Asp Arg Asp Pro Asp Ala Val Asp Ile
1               5                   10

<210> SEQ ID NO 16
<211> LENGTH: 364
<212> TYPE: DNA
<213> ORGANISM: homo sapiens

<400> SEQUENCE: 16
caggtccagc tggtgcagtc tggggctgag gtgatgaagc ctgggtcctc ggtgaaggtc      60
tcctgcaagg cttccggagg caccttccgc agctatgcta tcagttgggt gcgacaggcc     120
cctggacaag gcttgagtg gatgggaagg atcatcgttt tccttggtaa aacaaactac     180
gcacagaagt tccagggcag agtcacgctt accgcggaca atccacgac acagcctac     240 atggagctga gcagcctgag atctgaggac acggccgtgt attactgtac gggggaacct     300
ggggctcggg accccgacgc ttttgatatc tggggccaag ggacaatggt caccgtctct     360
tcag                                                                  364

<210> SEQ ID NO 17
<211> LENGTH: 121
<212> TYPE: PRT
<213> ORGANISM: homo sapiens

<400> SEQUENCE: 17

Gln Val Gln Leu Val Gln Ser Gly Ala Glu Val Met Lys Pro Gly Ser
1               5                   10                  15

Ser Val Lys Val Ser Cys Lys Ala Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Arg Ile Ile Val Phe Leu Gly Lys Thr Asn Tyr Ala Gln Lys Phe
    50                  55                  60

Gln Gly Arg Val Thr Leu Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Thr Gly Glu Pro Gly Ala Arg Asp Pro Asp Ala Phe Asp Ile Trp Gly
            100                 105                 110

Gln Gly Thr Met Val Thr Val Ser Ser
        115                 120

<210> SEQ ID NO 18
<211> LENGTH: 8
<212> TYPE: PRT
<213> ORGANISM: homo sapiens

<400> SEQUENCE: 18

Gly Gly Thr Phe Arg Ser Tyr Ala
1               5

<210> SEQ ID NO 19
<211> LENGTH: 8
<212> TYPE: PRT
<213> ORGANISM: homo sapiens

<400> SEQUENCE: 19

Ile Ile Val Phe Leu Gly Lys Thr
1               5

<210> SEQ ID NO 20
<211> LENGTH: 14
<212> TYPE: PRT
<213> ORGANISM: homo sapiens

<400> SEQUENCE: 20

Thr Gly Glu Pro Gly Ala Arg Asp Pro Asp Ala Phe Asp Ile
1               5                   10

<210> SEQ ID NO 21
<211> LENGTH: 364
<212> TYPE: DNA
<213> ORGANISM: homo sapiens

<400> SEQUENCE: 21
caggtccagc tggtgcagtc tggggctgag gtgaagaagc ctgggtcctc ggtgaaggtc      60
tcctgcaagc cttccggagg caccttcagg agctacgcta tcagctgggt acgacaggcc     120
cctggacaag ggcttgagtg gatgggaagg atcatcgttt tccttggtaa agtaaactac     180
gcacagaggt tcagggcag agtcacgctt accgcggaca atccacgac acagcctac       240
atggagctga gcagcctgag atctgaggac acggccgtgt attactgtac ggggggaaccct    300
ggggctcggg accccgacgc ttttgatatc tggggccaag ggacaatggt caccgtctct    360
tcag                                                                   364

<210> SEQ ID NO 22
<211> LENGTH: 121
<212> TYPE: PRT
<213> ORGANISM: homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Pro Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Arg Ile Ile Val Phe Leu Gly Lys Val Asn Tyr Ala Gln Arg Phe
    50                  55                  60

Gln Gly Arg Val Thr Leu Thr Ala Asp Lys Ser Thr Thr Thr Ala Tyr
65                  70                  75                  80

```
Met Glu Leu Ser Ser Leu Arg Ser Glu Asp Thr Ala Val Tyr Tyr Cys
             85                  90                  95

Thr Gly Glu Pro Gly Ala Arg Asp Pro Asp Ala Phe Asp Ile Trp Gly
        100                 105                 110

Gln Gly Thr Met Val Thr Val Ser Ser
        115                 120
```

<210> SEQ ID NO 23
<211> LENGTH: 8
<212> TYPE: PRT
<213> ORGANISM: homo sapiens

<400> SEQUENCE: 23

```
Gly Gly Thr Phe Arg Ser Tyr Ala
1               5
```

<210> SEQ ID NO 24
<211> LENGTH: 8
<212> TYPE: PRT
<213> ORGANISM: homo sapiens

<400> SEQUENCE: 24

```
Ile Ile Val Phe Leu Gly Lys Val
1               5
```

<210> SEQ ID NO 25
<211> LENGTH: 14
<212> TYPE: PRT
<213> ORGANISM: homo sapiens

<400> SEQUENCE: 25

```
Thr Gly Glu Pro Gly Ala Arg Asp Pro Asp Ala Phe Asp Ile
1               5                   10
```

<210> SEQ ID NO 26
<211> LENGTH: 321
<212> TYPE: DNA
<213> ORGANISM: homo sapiens

<400> SEQUENCE: 26

```
gacatccaga tgacccagtc tccatcctca ctgtctgcat ctgtaggaga cagagtcacc      60
atcacttgtc gggcgagtca gggtattcgc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt acccgctcac tttcggcgga    300
gggaccaagg tggagatcaa a                                              321
```

<210> SEQ ID NO 27
<211> LENGTH: 107
<212> TYPE: PRT
<213> ORGANISM: homo sapiens

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45
```

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
                100                 105

<210> SEQ ID NO 28
<211> LENGTH: 6
<212> TYPE: PRT
<213> ORGANISM: homo sapiens

<400> SEQUENCE: 28

Gly Gly Ile Arg Ser Trp
1               5

<210> SEQ ID NO 29
<211> LENGTH: 3
<212> TYPE: PRT
<213> ORGANISM: homo sapiens

<400> SEQUENCE: 29

Ala Ala Ser
1

<210> SEQ ID NO 30
<211> LENGTH: 9
<212> TYPE: PRT
<213> ORGANISM: homo sapiens

<400> SEQUENCE: 30

Gln Gln Tyr Asn Ser Tyr Pro Leu Thr
1               5

<210> SEQ ID NO 31
<211> LENGTH: 322
<212> TYPE: DNA
<213> ORGANISM: homo sapiens

<400> SEQUENCE: 31
gacatccaga tgacccagtc tccatcctca ctgtctgcat ctgtaggaga cagagtcacc    60
atcacttgtc gggcgagtca gggtattcgc agctggttag cctggtatca gcagaaacca   120
gagaaagccc ctaagtccct gatctatgct gcatccagtt tgcaaagtgg ggtcccatca   180
aggttcagcg gcagtggatc tgggacagat tcactctca ccatcagcag cctgcagcct   240
gaagattttg caacttatta ctgccaacag tataatagtt acccgctcac tttcggcgga   300
gggaccaagg tggagatcaa ac                                            322

<210> SEQ ID NO 32
<211> LENGTH: 107
<212> TYPE: PRT
<213> ORGANISM: homo sapiens

<400> SEQUENCE: 32

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Ser Trp
                20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 33
<211> LENGTH: 6
<212> TYPE: PRT
<213> ORGANISM: homo sapiens

<400> SEQUENCE: 33

Gln Gly Ile Arg Ser Trp
1               5

<210> SEQ ID NO 34
<211> LENGTH: 3
<212> TYPE: PRT
<213> ORGANISM: homo sapiens

<400> SEQUENCE: 34

Ala Ala Ser
1

<210> SEQ ID NO 35
<211> LENGTH: 9
<212> TYPE: PRT
<213> ORGANISM: homo sapiens

<400> SEQUENCE: 35

Gln Gln Tyr Asn Ser Tyr Pro Leu Thr
1               5

<210> SEQ ID NO 36
<211> LENGTH: 322
<212> TYPE: DNA
<213> ORGANISM: homo sapiens

<400> SEQUENCE: 36
gacatccaga tgacccagtc tccatcctca ctgtctgcat ctgtaggaga cagagtcacc    60
atcacttgtc gggcgagtca gggtattcgc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgctcac tttcggcgga   300
gggaccaagg tggagatcaa ac                                            322

<210> SEQ ID NO 37
<211> LENGTH: 107
<212> TYPE: PRT
<213> ORGANISM: homo sapiens

<400> SEQUENCE: 37

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 38
<211> LENGTH: 6
<212> TYPE: PRT
<213> ORGANISM: homo sapiens

<400> SEQUENCE: 38

Gln Gly Ile Arg Ser Trp
1               5

<210> SEQ ID NO 39
<211> LENGTH: 3
<212> TYPE: PRT
<213> ORGANISM: homo sapiens

<400> SEQUENCE: 39

Ala Ala Ser
1

<210> SEQ ID NO 40
<211> LENGTH: 9
<212> TYPE: PRT
<213> ORGANISM: homo sapiens

<400> SEQUENCE: 40

Gln Gln Tyr Asn Ser Tyr Pro Leu Thr
1               5

<210> SEQ ID NO 41
<211> LENGTH: 322
<212> TYPE: DNA
<213> ORGANISM: homo sapiens

<400> SEQUENCE: 41
gacatccaga tgacccagtc tccatcctca ctgtctgcat ctgtaggaga cagagtcacc      60
atcacttgtc gggcgagtca gggtattcgc agctggttag cctggtatca gcagaaacca     120
gagaaagccc ctaagtccct gatctatgct gcatccagtt tgcaaagtgg ggtcccatca     180
aggttcagcg gcagtggatc tgggacagat tcactctca ccatcagcag cctgcagcct     240
gaagattttg caacttatta ctgccaacag tataataatt atccgctcac tttcggcgga    300
gggaccaagg tggagatcaa ac                                              322

<210> SEQ ID NO 42
<211> LENGTH: 107
<212> TYPE: PRT
<213> ORGANISM: homo sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys
            100                 105

<210> SEQ ID NO 43
<211> LENGTH: 6
<212> TYPE: PRT
<213> ORGANISM: homo sapiens

<400> SEQUENCE: 43

Gln Gly Ile Arg Ser Trp
1               5

<210> SEQ ID NO 44
<211> LENGTH: 3
<212> TYPE: PRT
<213> ORGANISM: homo sapiens

<400> SEQUENCE: 44

Ala Ala Ser
1

<210> SEQ ID NO 45
<211> LENGTH: 9
<212> TYPE: PRT
<213> ORGANISM: homo sapiens

<400> SEQUENCE: 45

Gln Gln Tyr Asn Asn Tyr Pro Leu Thr
1               5

<210> SEQ ID NO 46
<211> LENGTH: 322
<212> TYPE: DNA
<213> ORGANISM: homo sapiens

<400> SEQUENCE: 46
gacatccaga tgacccagtc tccatcctca ctgtctgcat ctgtaggaga cagagtcacc      60
atcacttgtc gggcgagtca gggtattcgc agctggttag cctggtatca gcagaaacca    120
gagaaagccc ctaagtccct gatctatgct gcatccagtt tgcaaagtgg ggtcccatca    180
aggttcagcg gcagtggatc tgggacagat tcactctcac ccatcagcag cctgcagcct    240
gaagattttg caacttatta ctgccaacag tataataatt atccgctcac tttcggcgga    300
gggaccaagg tggagatcaa ac                                             322

<210> SEQ ID NO 47
<211> LENGTH: 107
<212> TYPE: PRT
<213> ORGANISM: homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys
            100                 105

<210> SEQ ID NO 48
<211> LENGTH: 6
<212> TYPE: PRT
<213> ORGANISM: homo sapiens

<400> SEQUENCE: 48

Gln Gly Ile Arg Ser Trp
1               5

<210> SEQ ID NO 49
<211> LENGTH: 3
<212> TYPE: PRT
<213> ORGANISM: homo sapiens

<400> SEQUENCE: 49

Ala Ala Ser
1

<210> SEQ ID NO 50
<211> LENGTH: 9
<212> TYPE: PRT
<213> ORGANISM: homo sapiens

<400> SEQUENCE: 50

Gln Gln Tyr Asn Asn Tyr Pro Leu Thr
1               5

<210> SEQ ID NO 51
<211> LENGTH: 300
<212> TYPE: PRT
<213> ORGANISM: homo sapiens

<400> SEQUENCE: 51

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

```
Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Gly Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 52
<211> LENGTH: 300
<212> TYPE: PRT
<213> ORGANISM: Homo sapiens

<400> SEQUENCE: 52

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
```

```
                145               150               155               160
Gly Glu Phe Asn Thr Ser Lys Ile Asn Tyr Gln Ser Cys Pro Asp Trp
                    165               170               175

Arg Lys Asp Cys Ser Asn Asn Pro Val Ser Val Phe Trp Lys Thr Val
                    180               185               190

Ser Arg Arg Phe Ala Glu Ala Ala Cys Asp Val Val His Val Met Leu
                    195               200               205

Asn Gly Ser Arg Ser Lys Ile Phe Asp Lys Asn Ser Thr Phe Gly Ser
                    210               215               220

Val Glu Val His Asn Leu Gln Pro Glu Lys Val Gln Thr Leu Glu Ala
225                 230               235               240

Trp Val Ile His Gly Gly Arg Glu Asp Ser Arg Asp Leu Cys Gln Asp
                    245               250               255

Pro Thr Ile Lys Glu Leu Glu Ser Ile Ile Ser Lys Arg Asn Ile Gln
                    260               265               270

Phe Ser Cys Lys Asn Ile Tyr Arg Pro Asp Lys Phe Leu Gln Cys Val
                    275               280               285

Lys Asn Pro Glu Asp Ser Ser Cys Thr Ser Glu Ile
                    290               295               300

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide

<400> SEQUENCE: 53

Cys Pro Pro Cys
1

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Tyr Pro Tyr Asp Val Pro Asp Tyr Ala
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic peptide

<400> SEQUENCE: 55

His His His His His His
1               5
```

ANTIBODIES AGAINST HUMAN CD38

RELATED APPLICATIONS

This application is a 35 U.S.C. 371 national stage filing of International Application No. PCT/EP2011/059507 filed Jun. 8, 2011, which claims priority to 61/353,082 filed Jun. 9, 2010; and PA 2010 00498 filed Jun. 9, 2010. The contents of the aforementioned applications are hereby incorporated by reference.

FIELD OF THE INVENTION

The present invention relates to antibodies directed to human CD38 and to uses of such antibodies, in particular therapeutic uses.

BACKGROUND OF THE INVENTION

CD38 is a type II transmembrane glycoprotein which is normally found on hemopoietic cells and in solid tissues. With regard to hemopoietic cells, the majority of medullary thymocytes are CD38$^+$, resting and circulating T- and B-cells are CD38$^-$ and activated cells are CD38$^+$. CD38 is also expressed on approximately 80% of resting NK cells and monocytes and on lymph node germinal center lymphoblasts, plasma B cells and some intrafollicular cells. CD38 can also be expressed by dendritic cells. A significant proportion of normal bone marrow cells, particular precursor cells, express CD38. In addition, 50-80% of umbilical cord blood cells is CD38$^+$ and remains so in human blood for the first two to three years of life. In addition to lymphoid precursor cells, CD38 is also expressed on erythrocytes and on platelets. With regard to solid tissues, CD38 is expressed in the gut by intra-epithelial cells and lamina propria lymphocytes, by Purkinje cells and neurofibrillary tangles in the brain, by epithelial cells in the prostate, β-cells in the pancreas, osteoclasts in the bone, retinal cells in the eye, and sarcolemma of smooth and striated muscle.

CD38 is also expressed in a variety of malignant hematological diseases, including multiple myeloma, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression could be involved, include, e.g. broncho-epithelial carcinomas of the lung, breast cancer (evolving from malignant proliferation of epithelial lining in ducts and lobules of the breast), pancreatic tumors, evolving from the b-cells (insulinomas), tumors evolving from epithelium in the gut (e.g. adenocarcinoma and squamous cell carcinoma), carcinoma in the prostate gland, seminomas in testis and ovarian cancers. In CNS, neuroblastomas express CD38.

Other disclosures also suggest the role of CD38 in autoimmunity such as Graves disease and thyroiditis (Antonelli A, et. al., Clin. Exp. Immunol. 126, 426-431, 2001), and type 1 and 2 Diabetes (Mallone R and Perin P C, Diabetes Metab Res Rev 2006; 22: 284-294) and inflammation of airway smooth muscle cells during asthma (Desphande et al. 2004 am J Respir Cell Mol Biol 31: 36-42)

CD38 is a multifunctional protein. Functions ascribed to CD38 include both receptor mediation in adhesion and signaling events and (ecto-) enzymatic activity. As an ectoenzyme, CD38 uses NAD$^+$ as substrate for the formation of cyclic ADP-ribose (cADPR) and ADPR, but also of nicotinamide and nicotinic acid-adenine dinucleotide phosphate (NAADP). cADPR has been shown to act as second messenger for Ca$^{2+}$ mobilization from the endoplasmatic reticulum. The CD38/cyclic ADP ribose system: 1) in lung, contributes to airway smooth muscle tone and responsiveness through its effects on agonist induced elevation of intra-cellular Ca$^{2+}$ (Desphande et al. 2005 Am J physiol Lung cell Mol Physiol 288: L773-L788), 2) regulates migration of neutrophil chemotaxis to bacterial chemoattractants, migration of DC precursors from blood to peripheral sites and migration of mature DCs from sites of inflammation to lymph nodes (Partida-Sanchez et al. Nat Med 7: 1209-121, 2001; Morita et al. 2008 J Pharmacol Sci. 2008 March; 106 (3):492-504; Partida-Sanchez et al. Immunity 20: 279-291, 2004), 3) is involved in astrocyte calcium signaling which has implications for neuroinflammation and HIV-1-associated dementia (Banerjee S. et. al., J. Neurimmune Pharmacol., 3, 154-164 (2008)), 4) regulates FcγR-mediated phagocytosis in murine macrophages (Song E., et. al., Biochem. and Biophys. Res. Comm., 367, 156-161, (2008), 5) is linked to insulin secretion Okamoto, Molecular and Cellular Biochemistry, 193, 115-118, 1999 and 6) has a key role in neuropeptide release and regulating maternal and social behaviors (Jin D et al. Nature 446: 41-45, 2007). In addition to signaling via Ca$^{2+}$, CD38 signaling occurs via cross-talk with antigen-receptor complexes on T and B cells or other types of receptor complexes, e.g. MHC molecules, and is in this way involved in several cellular responses, but also in switching and secretion of IgG1.

Several anti-CD38 antibodies are described in the literature, for instance in Lande R, et al., Cell Immunol. 220 (1), 30-8 (2002), Ausiello C M, et al., Tissue Antigens. 56 (6), 539-47 (2000), and Cotner T, et al., Int J Immunopharmacol. 3 (3), 255-68 (1981). Antibody binding to CD38 can have different effects on the functions of CD38. For instance, mouse anti-CD38 antibody IB4 has been shown to induce T cell activation as indicated by Ca$^{2+}$ mobilization in Jurkat cells (Zubiaur M, et al., J. Immunol. 159 (1), 193-205 (1997), to induce significant proliferation of peripheral blood mononuclear cells (PBMCs), to induce release of significant IL-6 levels and to induce release of detectable IFN-γ levels (Lande, Zubiaur Morra, Ansiello supra). Hara-Yokoyama et al. Int Immunopharmacol 8, 59-70 (2008) described one anti-mouse CD38 antibody (CS/2) which inhibits the NAD$^+$ glycohydrolase activity of CD38 and another anti-mouse CD38 antibody (clone 90) which stimulates the NAD$^+$ glycohydrolase activity of an isolated extracellular domain of CD38, but has little effect on the NAD$^+$ glycohydrolase activity of cell-surface CD38. As it can be seen from data presented below, the antibodies of the present invention provide activity on the surface of CD38 positive cells.

WO2006099875 (Genmab) describes several human anti-CD38 antibodies, including 003 and 005. Antibody 005 was shown to inhibit the production of cGDPR from NGD$^+$ by CD38.

In view of the multiple functions of human CD38, there is a need for new therapeutic antibodies that more specifically modulate particular functions of CD38.

SUMMARY OF THE INVENTION

The present invention provides a new class of anti-CD38 antibodies which through interacting with particular amino acids of human CD38 have a strong stimulating effect on the cADPR hydrolase activity of CD38 leading to decreased levels of cADPR. Furthermore, the anti-CD38 antibodies inhibit the ability of CD38 to catalyze the formation, via a base-exchange reaction, of nicotinic acid adenine dinucleotide 2'-phosphate (NAADP).

These antibodies are useful for the treatment of several diseases, including autoimmune and (chronic) inflammatory diseases, such as Type 1 and 2 diabetes, thyroiditis, Graves disease, arthritis, neuroinflammation and asthma.

Recent scientific work suggests that cADPR synthesized extracellularly by CD38, may be transported into cells through nucleoside transporters and then mobilize Ca(2+) through a FK506-binding protein-dependent process. This process may be involved in fMLP-induced intracellular Ca(2+) signaling and migration in human neutrophils (Morita et al. 2008 J Pharmacol Sci. 2008 March; 106 (3):492-504), migration of DC precursors from blood to peripheral sites and migration of mature DCs from sites of inflammation to lymph nodes (Partida-Sanchez et al. Immunity 20: 279-291, 2004). Without being bound by any particular theory, the reduction of cADPR levels obtained by treatment with an antibody of the present invention may thus reduce migration of neutrophils and dendritic cells and have anti-inflammatory effects. Accordingly, while the antibodies of the invention may be useful for a number of purposes, they may be particularly useful for the treatment of inflammation, e.g. in connection with autoimmune disease, because of their unique effects on the enzymatic activities of CD38, through binding at a particular site on CD38.

BRIEF DESCRIPTION OF THE DRAWINGS

FIG. 2(A) shows binding of the anti-CD38 antibodies 025, 026, 028 and 049 to wild type (WT) and mutant (T237A, Q272R, and S274F) CD38. FIG. 2(B) shows binding of the anti-CD38 antibodies 025, 028 and 049 to wild type (WT) and mutant (D202G) CD38.

FIG. 6(A) shows the percentage inhibition of cGDPR production (by recombinant human CD38 protein) in the presence of CD38 specific antibodies 025, 026, 028, 049 and 056 (3 μg/mL). FIG. 6(B) shows the effect of the anti-CD38 antibodies on cGDPR production in time. The anti-CD38 antibodies were used at a final concentration of 10 μg/ml. FIG. 6(C) shows the effect of the anti-CD38 antibodies on cGDPR production using serial dilutions (0.01-30 μg/mL) of 028 or isotype control HuMab-KLH. FIG. 6(D) shows the percentage inhibition of cGDPR production (by cellular expressed CD38 (CHO-CD38 cells)) in the presence of serial dilutions (0.01-30 μg/mL) of 028 or IgG1 isotype control HuMab-KLH.

FIG. 7(A) indicates the elution position of the products and substrates. FIG. 7(B) shows the antibody concentration dependence on $8NH_2$-cADPR production. HuMab-KLH (open circles), mAb-028 (closed circles).

FIG. 8(A) shows the results of incubating CD38 recombinant protein with cADPR or NAD in the presence of 10 μg HuMab-KLH (CD38+10 μg HuMab-KLH), 10 μg Ab 028 (CD38+10 μg Ab 028), or no antibody (CD38 control). Products of each reaction were analyzed by HPLC. FIG. 8(B) shows CD38 antibody titration at different concentrations on cADPR hydrolase activity as analyzed by HPLC. FIG. 8(C) shows the results of incubating CD38 recombinant protein with $^{32}P$-cADPR in the presence of mAb-003, mAb-028, daratumumab (005), or HuMab-KLH. Products were analyzed by thin layer chromatography. HuMab-KLH (open circles), mAb-028 (closed circles).

FIG. 9(A) shows the effect of the antibodies on NAADP production at the indicated concentrations. FIG. 9(B) shows the effect of mAb-028 titration on the rate of NAADP formation.

Figure 1:
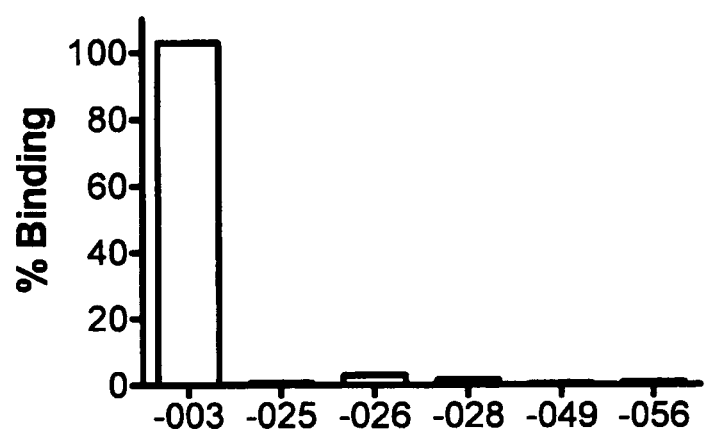
FIG. 1 shows cross-block studies of antibodies of the invention. More particularly, the figure shows the binding of 005-FITC to CHO-CD38 cells treated with excess unlabelled CD38-specific antibodies 025, 026, 028, 049 and 056.

```
                    SEQUENCE LIST
                        VH-region

SEQ ID NO: 1    VH 028 DNA
                caggtccaac tggtgcagtc tggggctgag gtgaagaagc ctgggtcctc ggtgaaggtc
                tcctgcaagg cttttggagg caccttcagc agctacgcta tcagctgggt gcgacaggcc
                cctggacaag ggcttgagtg gatgggaagg atcatccgtt tccttggtat agcaaactac
                gcacagaagt tccagggcag agtcacgctt atcgcggaca aatccacgaa cacagcctac
                atggagctga gcagcctgag atctgaggac acggccgttt attactgtgc gggggaacct
                ggggagcggg accccgatgc tgttgatatc tggggccaag ggacaatggt caccgtctct
                tca SEQ ID NO: 2    VH 028
                QVQLVQSGAE VKKPGSSVKV SCKAFGGTFS SYAISWVRQA PGQGLEWM
                GR IIRFLGIANYAQKFQGRVTL IADKSTNTAY MELSSLRSED TAVYYCAGEP
                GERDPDAVDI WGQGTMVTVSS

SEQ ID NO: 3    VH 028 CDR1
                GGTSFSSYA
```

| SEQUENCE LIST |
| --- |
| VH-region |

SEQ ID NO: 4    VH 028 CDR2
                IIRFLGIA

SEQ ID NO: 5    VH 028 CDR3
                AGEPGERDPDAVDI

SEQ ID NO: 6    VH 025 DNA
                caggtccaactggtgcagtctggggctgaggtgaagaagcctgggtcctcggtgaaggtc
                tcctgcaaggcttttggaggcaccttcagcagctatgctatcagctgggtacgacaggcc
                cctggacaagggcttgagtggatgggaaggatcatccgtttccttggtaaagcaaatcac
                gcacagaagttccagggcagagtcacgcttaccgcggacaaatccacgaacacagcctac
                atggagctgagcagcctgagatctgaggacacggccgtttattactgtgcgggggaacct
                ggggatcgggaccccgatgctgttgatatctggggccaagggacaatggtcaccgtctct
                tcag SEQ ID NO: 7    VH 025
                QVQLVQSGAEVKKPGSSVKVSCKAFGGTFSSYAISWVRQAPGQGLEWM
                GRIIRFLGKANHAQKFQGRVTLTADKSTNTAYMELSSLRSEDTAVYYCAGE
                PGDRDPDAVDIWGQGTMVTVSS

SEQ ID NO: 8    VH 025 CDR1
                GGTFSSYA

SEQ ID NO: 9    VH 025 CDR2
                IIRFLGKA

SEQ ID NO: 10   VH 025 CDR3
                AGEPGDRDPDAVDI

SEQ ID NO: 11   VH 026 DNA
                caggtccaactggtgcagtctggggctgaggtgaagaagcctgggtcctcggtgaaggtc
                tcctgcaaggcttttggaggcaccttcagcagttatgctattagctgggtgcgacaggcc
                cctggacaagggcttgagtggatgggaaggatcatccgtttccttggtaaaacaaatcac
                gcacagaagttccagggcagagtcacacttaccgcggacaaatccacgaacacagcctac
                atggagctgagcagcctgagatctgaggacacggccgtttattactgtgcgggggaacct
                ggggatcgggaccccgatgctgttgatatctggggccaagggacaatggtcaccgtctct
                tcag SEQ ID NO: 12   VH 026
                QVQLVQSGAEVKKPGSSVKVSCKAFGGTFSSYAISWVRQAPGQGLEWMGRIIR
                FLGKTNHAQKFQGRVTLTADKSTNTAYMELSSLRSEDTAVYYCAGEPGDRDPD
                AVDIWGQGTMVTVSS

SEQ ID NO: 13   VH 026 CDR1
                GGTFSSYA

SEQ ID NO: 14   VH 026 CDR2
                IIRFLGKT

SEQ ID NO: 15   VH 026 CDR3
                AGEPGDRDPDAVDI

SEQ ID NO: 16   VH 049 DNA
                caggtccagctggtgcagtctggggctgaggtgatgaagcctgggtcctcggtgaaggtc
                tcctgcaaggcttccggaggcaccttccgcagctatgctatcagttgggtgcgacaggcc
                cctggacaagggcttgagtggatgggaaggatcatccgttttccttggtaaaacaaactac
                gcacagaagttccagggcagagtcacgcttaccgcggacaaatccacgaccacagcctac
                atggagctgagcagcctgagatctgaggacacggccgtgtattactgtacgggggaacct
                ggggctcgggaccccgacgcttttgatatctggggccaagggacaatggtcaccgtctct
                tcag SEQ ID NO: 17   VH 049
                QVQLVQSGAEVMKPGSSVKVSCKASGGTFRSYAISWVRQAPGQGLEWM
                GRIIVFLGKTNYAQKFQGRVTLTADKSTTTAYMELSSLRSEDTAVYYCTGEP
                GARDPDAFDIWGQGTMVTVSS

SEQ ID NO: 18   VH 049 CDR1
                GGTFRSYA

SEQ ID NO: 19   VH 049 CDR2
                IIVFLGKT

-continued

SEQUENCE LIST
VH-region

SEQ ID NO: 20   VH 049 CDR3
                TGEPGARDPDAFDI

SEQ ID NO: 21   VH 056 DNA
                caggtccagctggtgcagtctggggctgaggtgaagaagcctggggtcctcggtgaaggtc
                tcctgcaagccttccggaggcaccttcaggagctacgctatcagctgggtacgacaggcc
                cctggacaagggcttgagtggatgggaaggatcatcgttttccttggtaaagtaaactac
                gcacagaggtttcagggcagagtcacgcttaccgcggacaaatccacgaccacagcctac
                atggagctgagcagcctgagatctgaggacacggccgtgtattactgtacgggggaacct
                ggggctcgggaccccgacgcttttgatatctggggccaagggacaatggtcaccgtctct
                tcag SEQ ID NO: 22   VH 056
                QVQLVQSGAEVKKPGSSVKVSCKPSGGTFRSYAISWVRQAPGQGLEWMGRIIVFL
                GKVNYAQRFQGRVTLTADKSTTTAYMELSSLRSEDTAVYYCTGEPGARDPDAFDIW
                GQGTMVTVSS

SEQ ID NO: 23   VH 056 CDR1
                GGTFRSYA

SEQ ID NO: 24   VH 056 CDR2
                IIVFLGKV

SEQ ID NO: 25   VH 056 CDR3
                TGEPGARDPDAFDI

SEQ ID NO: 26   VL 028 DNA
                gacatccagatgacccagtctccatcctcactgtctgcatctgtaggagacagagtcaccatcacttgtcgggcgag
                tcagggtattcgcagctggttagcctggtatcagcagaaaccagagaaagcccctaagtccctgatctatgctgcat
                ccagttttgcaaagtggggtcccatcaaggttcagcggcagtggatctgggacagatttcactctcaccatcagcag
                cctgcagcctgaagattttgcaacttattactgccaacagtataatagttacccgctcactttcggcggagggaccaa
                ggtggagatcaaa SEQ ID NO: 27   VL 028
                DIQMTQSPSSLSASVGDRVTITCRASQGIRSWLAWYQQKPEKAPKSLIYAASSLQSGVP
                SRFSGSGSGTDFTLTISSLQPEDFATYYCQQYNSYPLTFGGGTKVEIK

SEQ ID NO: 28   VL 028 CDR1
                GGIRSW

SEQ ID NO: 29   VL 028 CDR2
                AAS

SEQ ID NO: 30   VL 028 CDR3
                QQYNSYPLT

SEQ ID NO: 31   VL 025 DNA
                gacatccagatgacccagtctccatcctcactgtctgcatctgtaggagacagagtcacc
                atcacttgtcgggcgagtcagggtattcgcagctggttagcctggtatcagcagaaacca
                gagaaagcccctaagtccctgatctatgctgcatccagttttgcaaagtggggtcccatca
                aggttcagcggcagtggatctgggacagatttcactctcaccatcagcagcctgcagcct
                gaagattttgcaacttattactgccaacagtataatagttacccgctcactttcggcgga
                gggaccaaggtggagatcaaac SEQ ID NO: 32   VL 025
                DIQMTQSPSSLSASVGDRVTITCRASQGIRSWLAWYQQKPEKAPKSLIYAASSLQSGVP
                SRFSGSGSGTDFTLTISSLQPEDFATYYCQQYNSYPLTFGGGTKVEIK

SEQ ID NO: 33   VL 025 CDR1
                QGIRSW

SEQ ID NO: 34   VL 025 CDR2
                AAS

SEQ ID NO: 35   VL 025 CDR3
                QQYNSYPLT

SEQ ID NO: 36   VL 026 DNA
                gacatccagatgacccagtctccatcctcactgtctgcatctgtaggagacagagtcacc
                atcacttgtcgggcgagtcagggtattcgcagctggttagcctggtatcagcagaaacca
                gagaaagcccctaagtccctgatctatgctgcatccagttttgcaaagtggggtcccatca
                aggttcagcggcagtggatctgggacagatttcactctcaccatcagcagcctgcagcct
                gaagattttgcaacttattactgccaacagtataatagttacccgctcactttcggcgga
                gggaccaaggtggagatcaaac

```
                        SEQUENCE LIST
                          VH-region

SEQ ID NO: 37   VL 026
                DIQMTQSPSSLSASVGDRVTITCRASQGIRSWLAWYQQKPEKAPKSLIY
                AASSLQSGVPSRFSGSGSGTDFTLTISSLQPEDFATYYCQQYNSYPLTFGGGTKVEIK

SEQ ID NO: 38   VL 026 CDR1
                QGIRSW

SEQ ID NO: 39   VL 026 CDR2
                AAS

SEQ ID NO: 40   VL 026 CDR3
                QQYNSYPLT

SEQ ID NO: 41   VL 049 DNA
                gacatccagatgacccagtctccatcctcactgtctgcatctgtaggagacagagtcacc
                atcacttgtcgggcgagtcagggtattcgcagctggttagcctggtatcagcagaaacca
                gagaaagcccctaagtccctgatctatgctgcatccagttttgcaaagtggggtcccatca
                aggttcagcggcagtggatctgggacagatttcactctcaccatcagcagcctgcagcct
                gaagattttgcaacttattactgccaacagtataataattatccgctcactttcggcgga
                gggaccaaggtggagatcaaac SEQ ID NO: 42   VL 049
                DIQMTQSPSSLSASVGDRVTITCRASQGIRSWLAWYQQKPEKAPKSLIYAA
                SSLQSGVPSRFSGSGSGTDFTLTISSLQPEDFATYYCQQYNNYPLTFGGGTKVEIK

SEQ ID NO: 43   VL 049 CDR1
                QGIRSW

SEQ ID NO: 44   VL 049 CDR2
                AAS

SEQ ID NO: 45   VL 049 CDR3
                QQYNNYPLT

SEQ ID NO: 46   VL 056 DNA
                gacatccagatgacccagtctccatcctcactgtctgcatctgtaggagacagagtcacc
                atcacttgtcgggcgagtcagggtattcgcagctggttagcctggtatcagcagaaacca
                gagaaagcccctaagtccctgatctatgctgcatccagttttgcaaagtggggtcccatca
                aggttcagcggcagtggatctgggacagatttcactctcaccatcagcagcctgcagcct
                gaagattttgcaacttattactgccaacagtataataattatccgctcactttcggcgga
                gggaccaaggtggagatcaaac SEQ ID NO: 47   VL 056
                DIQMTQSPSSLSASVGDRVTITCRASQGIRSWLAWYQQKPEKAPKSLIYAASS
                LQSGVPSRFSGSGSGTDFTLTISSLQPEDFATYYCQQYNNYPLTFGGGTKVEIK

SEQ ID NO: 48   VL 056 CDR1
                QGIRSW

SEQ ID NO: 49   VL 056 CDR2
                AAS

SEQ ID NO: 50   VL 056 CDR3
                QQYNNYPLT

SEQ ID NO: 51   Mutant human CD38
                MANCEFSPVSGDKPCCRLSRRAQLCLGVSILVLILVVVLAVVVPRWRQQWSGPGTTKRF
                PETVLARCVKYTEIHPEMRHVDCQSVWDAFKGAFISKHPCNITEEDYQPLMKLGTQTVP
                CNKILLWSRIKDLAHQFTQVQRDMFTLEDTLLGYLADDLTWCGEFNTSKINYQSCPDWR
                KDCSNNPVSVFWKTVSRRFAEAACGVVHVMLNGSRSKIFDKNSTFGSVEVHNLQPEKV
                QTLEAWVIHGGREDSRDLCQDPTIKELESIISKRNIQFSCKNIYRPDKFLQCVKNPEDSS
                CTSEI SEQ ID NO: 52   Human CD38
                MANCEFSPVSGDKPCCRLSRRAQLCLGVSILVLILVVVLAVVVPRWRQQWSGPGTTKRF
                PETVLARCVKYTEIHPEMRHVDCQSVWDAFKGAFISKHPCNITEEDYQPLMKLGTQTVP
                CNKILLWSRIKDLAHQFTQVQRDMFTLEDTLLGYLADDLTWCGEFNTSKINYQSCPDWR
                KDCSNNPVSVFWKTVSRRFAEAACDVVHVMLNGSRSKIFDKNSTFGSVEVHNLQPEKV
                QTLEAWVIHGGREDSRDLCQDPTIKELESIISKRNIQFSCKNIYRPDKFLQCVKNPEDSS
                CTSEI
```

CDR regions are indicated according to IMGT.

The sequence of human CD38 is described in sequence 52. A mutant of human CD38 wherein S was mutated to F at position 274 was described in WO2006099875 as SEQ. ID NO: 34, and a mutation wherein Q was mutated to R at position 272 was described in WO2006099875 as SEQ. ID NO: 33. A mutant of human CD38 wherein D was mutated to G at position 202 is described above as SEQ. ID NO: 51.

DETAILED DESCRIPTION OF THE INVENTION

Definitions

The term "human CD38" when used herein includes any variants, isoforms and species homologs of human CD38 (Swissprot: locus CD38_HUMAN, accession P28907) which are naturally expressed by cells or are expressed on cells transfected with the human CD38 gene.

The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An anti-CD38 antibody may also be a bispecific antibody, diabody, or similar molecule (see for instance PNAS USA 90 (14), 6444-8 (1993) for a description of diabodies). Indeed, bispecific antibodies, diabodies, and the like, provided by the present invention may bind any suitable target in addition to a portion of CD38. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21 (11):484-90); (vi) camelid or nanobodies (Revets et al; Expert Opin Biol Ther. 2005 January; 5 (1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3, IgG4, IgD, IgA, IgE, or IgM) that is encoded by heavy chain constant region genes. An "anti-CD38 antibody" is an antibody which binds to the antigen CD38.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

In a preferred embodiment, the antibody of the invention is isolated. An "isolated antibody," as used herein, is intended to refer to an antibody which is substantially free of other antibodies having different antigenic specificities (for instance an isolated antibody that specifically binds to CD38 is substantially free of antibodies that specifically bind antigens other than CD38). An isolated antibody that specifically binds to an epitope, isoform or variant of human CD38 may, however, have cross-reactivity to other related antigens, for instance from other species (such as CD38 species homologs). Moreover, an isolated antibody may be substantially free of other cellular material and/or chemicals. In one embodiment of the present invention, a combination of "isolated" monoclonal antibodies having different specificities is combined in a well-defined composition.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1} \times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

The antibodies of the present invention have an effect on enzymatic systems as described in the examples section. The antibodies are described by stimulatory effects or inhibitory effects on different parameters. The stimulatory and inhibitory effects may be measured as disclosed in the examples herein.

An antibody as described and claimed herein may also be a functional variant of any of the specific antibodies described herein. Such a variant antibody is an antibody that differs from a specific antibody described herein by one or more suitable amino acid residue alterations, that is substitutions, deletions, insertions, or terminal sequence additions, for instance in the constant domain, and/or the variable regions (or any one or more CDRs thereof) in a single variant antibody. A functional variant of a $V_L$, $V_H$, or CDR region used in the context of an anti-CD38 antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-CD38 antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci. 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W.H. Freeman and Company.

As explained above, typically, amino acid sequence alterations, desirably do not substantially change the structural characteristics of the parent sequence (e.g., a replacement amino acid should not tend to disrupt secondary structure that characterizes the function of the parent sequence), but may be associated with advantageous properties, such as changing the functional or pharmacokinetic properties of the antibodies, for example increasing the half-life, altering the immunogenicity, providing a site for covalent or non-covalent binding to another molecule, reducing susceptibility to proteolysis, reducing susceptibility to oxidation, or altering the glycosylation pattern.

Examples of functional properties of antibodies, which may be altered or retained in variant anti-CD38 antibodies of the present invention compared to antibodies of prior art are for example:
(1) high affinity binding to CD38 and/or
(2) binding to transfected cells, e.g. CHO or HEK293 cells expressing CD38 and/or
(3) induction of CDC and/or
(4) induction of ADCC and/or
(5) alteration of enzymatic activity and/or
(6) induction of apoptosis after secondary cross-linking and/or
(7) phagocytosis The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 5, for instance no more than 4, 3, 2, or 1 amino acid difference from the amino acid sequence encoded by the germline immunoglobulin gene.

As used herein, the term "inhibits growth" (e.g. referring to cells, such as tumor cells) is intended to include any measurable decrease in the cell growth when contacted with an anti-CD38 antibody as compared to the growth of the same cells not in contact with an anti-CD38 antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g. effector cell phagocytosis, ADCC, CDC, and/or apoptosis.

The term "bispecific antibody" is intended to include any antibody which has two different binding specificities. The term "bispecific antibodies" also includes diabodies (see for instance Holliger, P. et al., PNAS USA 90, 6444-6448 (1993), Poljak, R. J. et al., Structure 2, 1121-1123 (1994)).

An "antibody deficient in effector function" or an "effector-function-deficient antibody" refers to an antibody which has a significantly reduced or no ability to activate one or more immune effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC).

The term "monovalent antibody" means in the context of the present invention that an antibody molecule is capable of binding a single molecule of the antigen, and thus is not able of antigen crosslinking.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell.

The term "vector," as used herein, is intended to refer to a nucleic acid molecule capable of transporting another nucleic acid to which it has been linked. Various types of vectors are well-known in the art. One type of vector is a plasmid.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK293 cells, NS/0 cells, and lymphocytic cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD38 antibodies when immunized with CD38 antigen and/or cells expressing CD38. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The terms "B-cell neoplasms" or "mature B-cell neoplasms" in the context of the present invention include small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an anti-CD38 antibody may vary according to factors such as the disease state, age, sex, and weight of the individual, and the ability of the anti-CD38 antibody to elicit a desired response in the individual. A therapeutically effective amount is also one in which any toxic or detrimental effects of the antibody or antibody portion are outweighed by the therapeutically beneficial effects.

An "anti-idiotypic" (Id) antibody is an antibody which recognizes unique determinants generally associated with the antigen-binding site of an antibody.

Antibodies of the Invention

The invention relates to an antibody that binds to human CD38 (SEQ ID NO: 52), wherein the antibody does not bind to a variant of human CD38 wherein Asp in position 202 has been substituted with Gly to the same degree that it binds to human CD38. In one embodiment, the EC50 of the binding of the antibody to the variant of human CD38 wherein Asp in position 202 has been substituted with Gly is less than 50%, such as less than 10%, less than 5%, or less than 1% of the EC50 of the binding of the antibody to human CD38.

In one embodiment, the antibody as defined above binds to a variant of human CD38 wherein Gln in position 272 has been substituted with Arg to the same degree that it binds to human CD38. In one embodiment, the EC50 of the binding of the antibody to the variant of human CD38 wherein Gln in position 272 has been substituted with Arg is at least 80%, such as at least 90%, such as at least 95%, such as at least 98% of the EC50 of the binding of the antibody to human CD38.

In one embodiment, the antibody as defined in any of the embodiments above binds to a variant of human CD38 wherein the Ser in position 274 has been substituted with Phe to the same degree that it binds to human CD38. In one embodiment, the EC50 of the binding of the antibody to a variant of human CD38 is at least 75%, such as at least 80%, such as at least 90%, such as at least 95%, such as at least 98% of the EC50 of the binding of the antibody to human CD38.

In one embodiment, the antibody as defined above possesses the following binding characteristics: (i) it does not bind to a variant of human CD38 wherein Asp in position 202 has been substituted with Gly to the same degree that it binds to human CD38, (ii) it binds to a variant of human CD38 wherein Gln in position 272 has been substituted with Arg to the same degree that it binds to human CD38, (iii) it binds to a variant of human CD38 wherein the Ser in position 274 has been substituted with Phe to the same degree that it binds to human CD38.

In one embodiment, the antibody as defined in any of the embodiments above binds human CD38 and has an inhibitory effect on the CD38 cyclase activity and a stimulatory effect on the CD38 hydrolase activity as measured in the assays of Example 8, such as wherein the inhibitory effect is at least 50-66% compared to the inhibitory effect on the CD38 cyclase activity in the absence of antibody.

In one embodiment, the antibody as defined in any of the embodiments above is encoded by a human heavy chain nucleic acid comprising a nucleotide sequence in its variable region as set forth in SEQ ID NO: 1, 6, 11, 16 or 21, and a human light chain nucleic acid comprising a nucleotide sequence in its variable region as set forth in SEQ ID NOs: 26, 31, 36, 41 or 46.

In one embodiment, the antibody as defined in any of the embodiments above is encoded by a human heavy chain and a human light chain nucleic acid comprising nucleotide sequences in their variable regions as set forth in SEQ ID NOs: 1 and 26, 6 and 31, 11 and 36, 16 and 41, or 21 and 46, respectively.

In one embodiment, the antibody as defined in any of the embodiments above comprises a VH CDR3 comprising
  a) the sequence as set forth in SEQ ID NOs: 5, 10, 15, 20 or 25, or
  b) a variant of said sequence, such as a variant having at most 1, 2 or 3 amino acid modifications, preferably substitutions, such as conservative substitutions.

In one embodiment, the antibody as defined in any of the embodiments above comprises a VH CDR3 having the sequence set forth in SEQ ID NOs: 5, 10, 15, 20 or 25, and comprising a VL CDR3 having the sequence set forth in SEQ ID NO: 30, 35, 40, 45 or 50.

In one embodiment, the antibody as defined in any of the embodiments above comprises SEQ ID NO: 5 and SEQ ID NO: 30, or SEQ ID NO: 10 and SEQ ID NO: 35, or SEQ ID NO: 15 and SEQ ID NO: 40, or SEQ ID NO: 20 and SEQ ID NO: 45, or SEQ ID NO: 25 and SEQ ID NO: 50 as the VH CDR3 and VL CDR3 respectively.

In one embodiment, the antibody as defined in any of the embodiments above comprises
(i) a VH CDR1 having the sequence as set forth in any of the sequences SEQ ID NOs: 3, 8, 13, 18 and 23, a VH CDR2 having the sequence as set forth in any of the sequences SEQ ID NOs: 4, 9, 14, 19 and 24, a VH CDR3 having the sequence as set forth in any of the sequences SEQ ID NOs: 5, 10, 15, 20 and 25, a VL CDR1 having the sequence as set forth in any of the sequences SEQ ID NO: 28, 33, 38, 43 and 48, a VL CDR2 having the sequence as set forth in any of the sequences SEQ ID NOs: 29, 34, 39, 44 and 49, a VL CDR3 having the sequence as set forth in any of the sequences SEQ ID NOs: 30, 35, 40, 45 and 50,
(ii) a VH CDR1 having the sequence as set forth in SEQ ID NO: 3, a VH CDR2 having the sequence as set forth in SEQ ID NOs: 4, a VH CDR3 having the sequence as set forth in SEQ ID NO: 5, a VL CDR1 having the sequence as set forth in SEQ ID NO: 28, a VL CDR2 having the sequence as set forth in SEQ ID NO: 29, a VL CDR3 having the sequence as set forth in SEQ ID NO: 30,
(iii) a VH CDR1 having the sequence as set forth in SEQ ID NO: 8, a VH CDR2 having the sequence as set forth in SEQ ID NOs: 9, a VH CDR3 having the sequence as set forth in SEQ ID NO: 10, a VL CDR1 having the sequence as set forth in SEQ ID NO 33, a VL CDR2 having the sequence as set forth in SEQ ID NO: 34, a VL CDR3 having the sequence as set forth in SEQ ID NO: 35,
(iv) a VH CDR1 having the sequence as set forth in SEQ ID NO: 13, a VH CDR2 having the sequence as set forth in SEQ ID NO: 14, a VH CDR3 having the sequence as set forth in SEQ ID NO: 15, a VL CDR1 having the sequence as set forth in SEQ ID NO: 38, a VL CDR2 having the sequence as set forth in SEQ ID NO: 39, a VL CDR3 having the sequence as set forth in SEQ ID NO: 40,
(v) a VH CDR1 having the sequence as set forth in SEQ ID NO: 18, a VH CDR2 having the sequence as set forth in SEQ ID NOs: 19, a VH CDR3 having the sequence as set forth in SEQ ID NO: 20, a VL CDR1 having the sequence as set forth in SEQ ID NO: 43, a VL CDR2 having the sequence as set forth in SEQ ID NO: 44, a VL CDR3 having the sequence as set forth in SEQ ID NO: 45,
(vi) a VH CDR1 having the sequence as set forth in SEQ ID NO: 23, a VH CDR2 having the sequence as set forth in SEQ ID NOs: 24, a VH CDR3 having the sequence as set forth in SEQ ID NO: 25, a VL CDR1 having the sequence as set forth in SEQ ID NO 48, a VL CDR2 having the sequence as set forth in SEQ ID NO: 49, a VL CDR3 having the sequence as set forth in SEQ ID NO: 50, or
(vii) a variant of any of the antibodies defined above, wherein said variant preferably has at most 1, 2 or 3 amino acid modifications, more preferably amino-acid substitutions, such as conservative amino acid substitutions in one or more of said sequences.

In one embodiment, the antibody as defined in any of the embodiments above comprises a VH region
(i) comprising the sequence of SEQ ID NOs: 2, 7, 12, 17 or 22, or
(ii) having at least 80% identity, such as 90%, or 95%, or 97%, or 98%, or 99% or 100% identity to the VH region sequence set forth in SEQ ID NOs: 2, 7, 12, 17 or 22.

In one embodiment, the antibody as defined in any of the embodiments above comprises a VL region
(i) comprising the sequence of SEQ ID NOs: 27, 32, 37, 42 or 47, or
(ii) having at least 80% identity, such as 90%, or 95%, or 97%, or 98%, or 99% or 100% identity to a VL region sequence selected from the group consisting of: SEQ ID NOs: 27, 32, 37, 42 or 47.

In one embodiment, the antibody as defined in any of the embodiments above comprises a VH region comprising any of the sequences of SEQ ID NOs: 2, 7, 12, 17 and 22, and a VL region comprising any of the sequences of SEQ ID NOs: 27, 32, 37, 42 and 47.

In one embodiment, the antibody as defined in any of the embodiments above comprises
(i) a VH region comprising the sequence as set forth in SEQ ID NO: 2, and a VL region comprising any the sequence as set forth in SEQ ID NO: 27,
(ii) a VH region comprising the sequence as set forth in SEQ ID NO: 7, and a VL region comprising any the sequence as set forth in SEQ ID NO: 32,
(iii) a VH region comprising the sequence as set forth in SEQ ID NO: 12, and a VL region comprising any the sequence as set forth in SEQ ID NO: 37,
(iv) a VH region comprising the sequence as set forth in SEQ ID NO: 17, and a VL region comprising any the sequence as set forth in SEQ ID NO: 42, or
(v) a VH region comprising the sequence as set forth in SEQ ID NO: 22, and a VL region comprising any the sequence as set forth in SEQ ID NO: 47.

In one embodiment, the invention relates to an anti-CD38 antibody which binds to the same epitope on CD38 as an anti-CD38 antibody as described in any one of the embodiments above.

In one embodiment, the invention relates to an anti-CD38 antibody which has substantially the same specific binding characteristics for binding human CD38 as described in any one of the embodiments above.

In one embodiment, the antibody as defined in any of the embodiments above is capable of inducing antibody-dependent cellular cytotoxicity (ADCC), such as in Daudi cells, preferably with an $EC_{50}$ value of 5 nM or less, e.g. 1 nM or less, such as 0.2 nM or less, as determined by the method described in Example 6 herein.

In one embodiment, the antibody as defined in any of the embodiments above is not capable of inducing ADCC in Daudi cells according to the method described in Example 6 herein.

In one embodiment, the antibody as defined in any of the embodiments above is not capable of inducing complement-dependent cytotoxicity (CDC) in CHO-CD38 cells.

In one embodiment, the antibody as defined in any of the embodiments above binds to human CD38 with a $K_D$ of $10^{-8}$ M or less, preferably with a $K_D$ of $10^{-9}$ M or less.

In one embodiment, the antibody as defined in any of the embodiments above is a human monovalent antibody.

In one embodiment, the antibody as defined in any of the embodiments above is a full length IgG1, IgG2, IgG3, IgG4, IgD, IgA, IgE, or IgM antibody, such as an IgG1 antibody, preferably an IgG1,κ antibody or an IgM antibody, preferably an IgM,κ antibody.

In one embodiment, the antibody as defined in any of the embodiments above is an antibody fragment or a single-chain antibody.

In one embodiment, the antibody as defined in any of the embodiments above is an effector-function-deficient antibody, such as a stabilized human IgG4 antibody.

In one embodiment, such stabilized IgG4 antibody is an antibody wherein arginine at position 409 in the heavy chain constant region of human IgG4 is substituted with lysine, threonine, methionine, or leucine, preferably lysine. In one embodiment, such antibody comprises a Lys residue at the position corresponding to 409 or the CH3 region of the antibody has been replaced by the CH3 region of human IgG1, of human IgG2 or of human IgG3. In one embodiment, such antibody does not comprise a Cys-Pro-Pro-Cys sequence in the hinge region. In another embodiment, such antibody does comprise a Cys-Pro-Pro-Cys sequence in the hinge region.

In one embodiment, the antibody as defined in any of the embodiments above is a monovalent antibody.

In one embodiment, such monovalent antibody is constructed by a method comprising:
i) providing a nucleic acid construct encoding the light chain of said monovalent antibody, said construct comprising a nucleotide sequence encoding the VL region of SEQ ID NO: 27, 32, 37, 42 or 47 and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;
ii) providing a nucleic acid construct encoding the heavy chain of said monovalent antibody, said construct comprising a nucleotide sequence encoding the VH region of SEQ ID NO: 2, 7, 12 17 or 22 and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;
iii) providing a cell expression system for producing said monovalent antibody;
iv) producing said monovalent antibody by co-expressing the nucleic acid constructs of (i) and (ii) in cells of the cell expression system of (iii).

In one embodiment, the $C_H$ region comprising the $C_H2$ and $C_H3$ regions has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

In one embodiment, such monovalent antibody is of the IgG4 subtype, but the $C_H3$ region has been modified so that one or more of the following amino acid substitutions have been made: Thr (T) in position 366 has been replaced by Ala (A); Leu (L) in position 368 has been replaced by Ala (A); Leu (L) in position 368 has been replaced by Val (V); Phe (F) in position 405 has been replaced by Ala (A); Phe (F) in position 405 has been replaced by Leu (L); Tyr (Y) in position 407 has been replaced by Ala (A); Arg (R) in position 409 has been replaced by Ala (A).

In one embodiment, the heavy chain of such monovalent antibody has been modified such that the entire hinge has been deleted.

In one embodiment, the sequence of said monovalent antibody has been modified so that it does not comprise any acceptor sites for N-linked glycosylation.

In one embodiment, the antibody as defined in any of the embodiments above inhibits the CD38 catalyzed synthesis of cGDPR by at least 25%, such as at least 30% after 90 minutes at a concentration of 3 μg/ml as determined by the spectophotometric method described in Example 8 of the specification.

In one embodiment, the antibody as defined in any of the embodiments above inhibits the CD38 catalyzed synthesis of cADPR by at least 25%, such as at least 30% after 90 minutes at a concentration of 3 μg/ml as determined by the HPLC method described in Munshi et al., J. Biol. Chem. 275, 21566-21571 (2000).

In one embodiment, the antibody stimulates the hydrolase activity of CD38 by at least 25%.

In one embodiment, the antibody stimulates the NAD hydrolase activity of CD38 by at least 25%.

In one embodiment, the antibody as defined in any of the embodiments above stimulates the cADPR-hydrolase activity of CD38 by at least 25%.

In one embodiment, the antibody as defined in any of the embodiments above inhibits the ability of CD38 to catalyze the formation, via a base-exchange reaction, of NAADP with an IC50 of below 0.5 μg/mL, such as of below 0.2 μg/mL by the method described in Example 8 of the specification.

In one embodiment, the invention relates to an antibody drug conjugate comprising an antibody as defined in any of the embodiments above, wherein the antibody has been conjugated to a cytotoxic agent, a radioisotope, or a drug. In one embodiment, the antibody has been conjugated to an auristatin or a functional peptide analog or derivate thereof via a linker.

In one embodiment, the invention relates to a bispecific antibody comprising an antibody as defined in any of the embodiments above and a second binding specificity for a human effector cell or a cancer antigen. In one embodiment, the second binding specificity is for a human Fc receptor or for a T cell receptor, such as CD3.

In one embodiment, the invention relates to an isolated nucleic acid encoding an antibody as defined in any of the embodiments above.

In one embodiment, the invention relates to an expression vector comprising a nucleotide sequence encoding one or more of the amino acid sequences as defined in any of the embodiments above.

In one embodiment, the expression vector further comprises a nucleotide sequence encoding the constant region of a light chain, a heavy chain or both light and heavy chains of a human antibody.

In one embodiment, the invention relates to a recombinant eukaryotic or prokaryotic host cell which produces an antibody as defined in any of the embodiments above.

In one embodiment, the invention relates to a pharmaceutical composition comprising an antibody, an immunoconjugate, a bispecific antibody, or an expression vector as defined in any of the embodiments above and a pharmaceutically acceptable carrier.

In one embodiment, the invention relates to an antibody as defined in any of the embodiments above for use as a medicament.

In one embodiment, the invention relates to an antibody as defined in any of the embodiments above for use in inhibiting growth and/or proliferation, migration or inducing phagocytosis of a tumor cell expressing CD38.

In one embodiment, the invention relates to an antibody as defined in any of the embodiments above for use in treating rheumatoid arthritis.

In one embodiment, the invention relates to an antibody as defined in any of the embodiments above for use in treating a disorder selected from chronic lymphocytic leukemia (CLL), acute lymphoblastic leukemia (ALL), acute myelogenous leukemia (adults) (AML), mantle cell lymphoma, follicular lymphoma, and diffuse large B-cell lymphoma.

In one embodiment, the invention relates to an antibody as defined in any of the embodiments above for use in treating multiple myeloma.

In one embodiment, the invention relates to a method for producing an anti-CD38 antibody as defined in any of the embodiments above, said method comprising the steps of
a) culturing a host cell as defined in any of the embodiments above, and
b) purifying the anti-CD38 antibody from the culture media.

In one embodiment, the invention relates to diagnostic composition comprising an antibody as defined in any of the embodiments above.

In one embodiment, the invention relates to a method for detecting the presence of CD38 antigen, or a cell expressing CD38, in a sample comprising:
  contacting the sample with an anti-CD38 antibody as defined in any of the embodiments above under conditions that allow for formation of a complex between the antibody or bispecific molecules and CD38; and
  analyzing whether a complex has been formed.

In one embodiment, the invention relates to a kit for detecting the presence of CD38 antigen, or a cell expressing CD38, in a sample comprising an anti-CD38 antibody as defined in any of the embodiments above and instructions for use of the kit.

In one embodiment, the invention relates to an anti-idiotypic antibody which binds to an anti-CD38 antibody as defined in any of the embodiments above.

In one embodiment, the invention relates to a method of inhibiting growth and/or proliferation migration or inducing phagocytosis of a cell expressing CD38, comprising administration of an antibody, an immunoconjugate, a bispecific antibody, an expression vector or a pharmaceutical composition as defined in any of the embodiments above, such that the growth and/or proliferation, migration or phagocytosis of the cell is inhibited.

In one embodiment, the invention relates to a method of treating a disease or disorder involving cells expressing CD38 in a subject, which method administration of an antibody, an immunoconjugate, a bispecific antibody, an expression vector or a pharmaceutical composition as defined in any of the embodiments above to a subject in need thereof.

In one embodiment, the disease or disorder is rheumatoid arthritis.

In another embodiment, the disease or disorder is selected from chronic lymphocytic leukemia (CLL), acute lymphoblastic leukemia (ALL), acute myelogenous leukemia (adults) (AML), mantle cell lymphoma, follicular lymphoma, and diffuse large B-cell lymphoma.

In yet another embodiment, the disease or disorder is multiple myeloma.

In one embodiment, the method as defined in any of the embodiments above comprises administration of one or more further therapeutic agents to the subject, such as one or more further therapeutic agents are selected from a chemotherapeutic agent, an anti-inflammatory agent, or an immunosuppressive and/or immunomodulatory agent. In one embodiment, the one or more further therapeutic agents are selected from a group consisting of cisplatin, gefitinib, cetuximab, rituximab, ofatumumab, bevacizumab, erlotinib, bortezomib, thalidomide, pamidronate, zoledronic acid, clodronate, risendronate, ibandronate, etidronate, alendronate, tiludronate, arsenic trioxide, lenalidomide, dexamethasone, prednisolone, filgrastim, pegfilgrastim, sargramostim, suberoylanilide hydroxamic acid, and SCIO-469.

An embodiment of the invention provides an antibody that binds to human CD38, wherein the antibody does not bind to a variant of human CD38 wherein Asp in position 202 has been substituted with Gly.

An embodiment of the invention provides an antibody according to the embodiment above, wherein the EC50 of the binding of the antibody to a variant of human CD38 is less than 50%, such as less than 10%, less than 5%, or less than 1% of the EC50 of the binding of the peptide to human CD38.

An embodiment of the invention provides an antibody according to any of the above embodiments, wherein the antibody binds to a variant of human CD38 wherein the Gln in position 272 has been substituted with Arg to the same degree that it binds to human CD38.

An embodiment of the invention provides an antibody according to the above embodiment, wherein the EC50 of the binding of the antibody to a variant of human CD38 is at least 80%, such as at least 90%, such as at least 95%, such as at least 98% of the EC50 of the binding of the peptide to human CD38.

An embodiment of the invention provides an antibody according to any of the above embodiments, wherein the antibody binds to a variant of human CD38 wherein the Ser in position 274 has been substituted with Phe to the same degree that it binds to human CD38.

An embodiment of the invention provides an antibody according to the above embodiment, wherein the EC50 of the binding of the antibody to a variant of human CD38 is at least 75%, such as at least 80%, such as at least 90%, such as at least 95%, such as at least 98% of the EC50 of the binding of the peptide to human CD38.

An embodiment of the invention provides an antibody according to any of the above embodiments, wherein the antibody possesses the following binding characteristics: (i) it does not bind to a variant of human CD38 wherein Asp in position 202 has been substituted with Gly to the same degree that it binds to human CD38 (ii) it binds to a variant of human CD38 wherein the Gln in position 272 has been substituted with Arg to the same degree that it binds to human CD38 (iii) it binds to a variant of human CD38 wherein the Ser in position 274 has been substituted with Phe to the same degree that it binds to human CD38.

An embodiment of the invention provides an antibody according to any of the above embodiments, that binds human CD38 and has an inhibitory effect on the CD38 cyclase activity and a stimulatory effect on the CD38 hydrolase activity as measured in the assays of Example 8.

An embodiment of the invention provides an antibody according to the above embodiment, wherein the inhibitory effect is at least 50-66% compared to CD38 alone.

An embodiment of the invention provides an antibody binding to human CD38 encoded by a human heavy chain nucleic acids comprising nucleotide sequences in their variable regions as set forth the in seq id no.: 1, 6, 11, 16 or 21, and a human light chain comprising nucleotide sequences in their variable regions as set forth in seq id no. 26, 31, 36, 41 or 46, and comprising conservative sequence modifications of the sequences set forth above.

An embodiment of the invention provides an antibody according to the above embodiment, encoded by a human heavy chain and a human light chain nucleic acids comprising nucleotide sequences in their variable regions as set forth the in seq id no.: 1 and 26, 6 and 31, 11 and 36, 16 and 41 or 21 and 46, respectively, and comprising conservative sequence modifications of the sequences set forth above.

An embodiment of the invention provides an antibody binding to human CD38 comprising a VH CDR3 region having
  a) the sequence as set forth in SEQ ID NOs: 5, 10, 15, 20 or 25 30 or
  b) a variant of said sequence, such as a variant having at most 1, 2 or 3 amino-acid modifications, preferably substitutions, such as conservative substitutions.

An embodiment of the invention provides an antibody binding to human CD38 comprising a VH CDR3 region having the sequence as set forth in SEQ ID NOs: 5, 10, 15, 20, 25 or 30 and comprising a VL CDR3 region having the sequence set forth in SEQ ID NO: 30, 35, 40, 45 or 50;

An embodiment of the invention provides an antibody binding to human CD38 comprising a VH CDR3 region having the sequence as set forth in SEQ ID NO: 5 and a VL CDR3 region comprising SEQ ID NO: 30, or SEQ ID NO: 10 and SEQ ID NO: 35, or SEQ ID NO: 15 and SEQ ID NO: 40, or SEQ ID NO: 20 and SEQ ID NO: 45, or SEQ ID NO: 25 and SEQ ID NO: 45, or SEQ ID NO: 30 and SEQ ID NO: 50, as VH CDR3 region and VL CDR3 region respectively.

An embodiment of the invention provides an anti-CD38 antibody according to any of the above embodiments, wherein the antibody comprises a VH CDR1 region having the sequence as set forth in any of the sequences SEQ ID NOs: 3, 8, 13, 18 or 23, a VH CDR2 region having the sequence as set forth in any of the sequences SEQ ID NOs: 4, 9, 14, 19 or 24, a VL CDR3 region having the sequence as set forth in any of the sequences SEQ ID NOs: 30, 35, 40, 45 or 50, and a VH CDR3 region having the sequence as set forth in SEQ ID NOs: 5, 10, 15, 20 or 25.

An embodiment of the invention provides an antibody which binds to CD38, wherein the antibody comprises a VH CDR1 region having the sequence as set forth in any of the sequences SEQ ID NOs: 3, 8, 13, 18 or 23, a VH CDR2 region having the sequence as set forth in any of the sequences SEQ ID NOs: 4, 9, 14, 19 or 24, a VH CDR3 region having the sequence as set forth in SEQ ID NOs: 5, 10, 15, 20 or 25, a VL CDR1 region as set forth in SEQ ID NOs: 28, 33, 38, 43 or 48, a VL CDR2 region as set forth in SEQ ID NOs: 29, 34, 39, 44 or 49, a VL CDR3 region having the sequence as set forth in any of the sequences SEQ ID NOs: 30, 35, 40, 45 or 50 or
  a variant of said antibody, wherein said variant preferably has at most 1, 2 or 3 amino-acid modifications, more preferably amino-acid substitutions, such as conservative amino-acid substitutions in said sequences.

An embodiment of the invention provides an antibody which binds to CD38, wherein the antibody comprises a VH CDR1 region having the sequence as set forth in any of the sequences SEQ ID NOs: 3, 8, 13, 18 or 23, a VH CDR2 region having the sequence as set forth in any of the sequences SEQ ID NOs: 4, 9, 14, 19 or 24, a VH CDR3 region having the sequence as set forth in SEQ ID NOs: 5, 10, 15, 20 or 25, a VL CDR1 region as set forth in SEQ ID NOs: 28, 33, 38, 43 or 48, a VL CDR2 region as set forth in SEQ ID NOs: 29, 34, 39, 44 or 49, a VL CDR3 region having the sequence as set forth in any of the sequences SEQ ID NOs: 30, 35, 40, 45 or 50;

An embodiment of the invention provides an anti-CD38 antibody according to any of the above embodiments, comprising a VH having at least 80% identity, such as 90%, or 95%, or 97%, or 98%, or 99% or 100% identity to the VH region sequence set forth in SEQ ID NOs: 2, 7, 12, 17, or 22.

An embodiment of the invention provides an anti-CD38 antibody according to any of the above embodiments, comprising a VL having at least 80% identity, such as 90%, or 95%, or 97%, or 98%, or 99% or 100% identity to a VL region sequence selected from the group consisting of: SEQ ID NOs: 27, 32, 37, 42 or 47.

An embodiment of the invention provides an anti-CD38 antibody according to any of the above embodiments, comprising a VH region comprising the sequence of SEQ ID NOs: 2, 7, 12, 17 or 22 and a VL region comprising the sequence of SEQ ID NOs: SEQ ID NOs: 27, 32, 37, 42 or 47.

An embodiment of the invention provides an antibody which competes with an antibody according to any of the above embodiments, for binding to CD38.

An embodiment of the invention provides an anti-CD38 antibody, which competes for CD38 binding with an anti-CD38 antibody comprising a VH region comprising any of the sequences of SEQ ID NOs: 2, 7, 12, 17 or 22 and a VL region comprising any of the sequences of SEQ ID NO: 27, 32, 37, 42 or 47.

An embodiment of the invention provides an anti-CD38 antibody according to any of the above embodiments, wherein the antibody binds to the same epitope on CD38 as an anti-CD38 antibody as described in any of the above embodiments.

An embodiment of the invention provides an antibody having substantially the same specific binding characteristics for binding human CD38 has an antibody according to any of the above embodiments.

An embodiment of the invention provides an anti-CD38 antibody according to any of the above embodiments, wherein the antibody is capable of inducing complement-dependent cytotoxicity (CDC) in CHO-CD38 cells.

An embodiment of the invention provides an anti-CD38 antibody according to any of the above embodiments, wherein the antibody is capable of inducing antibody-dependent cellular cytotoxicity (ADCC).

An embodiment of the invention provides an anti-CD38 antibody of claim 25, wherein said antibody induces ADCC in Daudi cells, preferably with an $EC_{50}$ value of 5 nM or less, e.g. 1 nM or less, such as 0.2 nM or less, as determined by the method described in Example 6 herein.

An embodiment of the invention provides an anti-CD38 antibody according to any of the above embodiments, wherein the antibody is not capable of inducing ADCC.

An embodiment of the invention provides an anti-CD38 antibody according to any of the above embodiments, wherein the antibody is not capable of inducing complement-dependent cytotoxicity (CDC).

An embodiment of the invention provides an anti-CD38 antibody according to any of the above embodiments, wherein the antibody binds to human CD38 with a $K_D$ of $10^{-8}$ M or less, preferably with a $K_D$ of $10^{-9}$ M or less.

An embodiment of the invention provides an anti-CD38 antibody according to any of the above embodiments, wherein the antibody comprises:
 a heavy chain variable region derived from a human germline $V_H$ sequence selected from the group consisting of: IGHV1-69*04, and/or IGHJ3*02
 a light chain variable region derived from a human germline Vκ sequence selected from the group consisting of: IGKV1D-16*01, and/or IGKJ4*01.

An embodiment of the invention provides an anti-CD38 antibody according to any of the above embodiments, which is a human antibody.

An embodiment of the invention provides an antibody according to any of the above embodiments, characterized in that it is a full length IgG1, IgG2, IgG3, IgG4, IgD, IgA, IgE, or IgM antibody, such as an IgG1 antibody, preferably an IgG1,κ antibody or an IgM antibody, preferably an IgM,κ antibody.

An embodiment of the invention provides an anti-CD38 antibody according to any of the above embodiments, wherein the antibody is an antibody fragment or a single-chain antibody.

An embodiment of the invention provides an anti-CD38 antibody according to any of the above embodiments, wherein the antibody is conjugated to another moiety, such as a cytotoxic moiety, a radioisotope or a drug.

An embodiment of the invention provides an anti-CD38 antibody according to any of the above embodiments, wherein the antibody is an effector-function-deficient antibody.

An embodiment of the invention provides an anti-CD38 antibody of the above embodiment, wherein the effector-function-deficient anti-CD38 antibody is a stabilized human IgG4 antibody.

An embodiment of the invention provides an anti-CD38 antibody of the above embodiment, wherein the stabilized IgG4 antibody is an antibody wherein arginine at position 409 in the heavy chain constant region of human IgG4 is substituted with lysine, threonine, methionine, or leucine, preferably lysine.

An embodiment of the invention provides an anti-CD38 antibody of the above embodiment, wherein said antibody comprises a Lys residue at the position corresponding to 409 or the CH3 region of the antibody has been replaced by the CH3 region of human IgG1, of human IgG2 or of human IgG3.

An embodiment of the invention provides an anti-CD38 antibody of the above embodiments, wherein said antibody does not comprise a Cys-Pro-Pro-Cys (SEQ ID NO: 53) sequence in the hinge region.

An embodiment of the invention provides an anti-CD38 antibody of the above embodiments, wherein said antibody does comprise a Cys-Pro-Pro-Cys (SEQ ID NO: 53) sequence in the hinge region.

An embodiment of the invention provides an anti-CD38 antibody according to any of the above embodiments, wherein the antibody is a monovalent antibody.

An embodiment of the invention provides an anti-CD38 antibody of the above embodiment, wherein said monovalent antibody is constructed by a method comprising:
i) providing a nucleic acid construct encoding the light chain of said monovalent antibody, said construct comprising a nucleotide sequence encoding the VL region of a selected antigen specific antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;
ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;
iii) providing a cell expression system for producing said monovalent antibody;
iv) producing said monovalent antibody by co-expressing the nucleic acid constructs of (i) and (ii) in cells of the cell expression system of (iii).

An embodiment of the invention provides an anti-CD38 antibody of the above embodiment, wherein the monovalent antibody comprises
(i) a variable region of an antibody according to any of the above embodiments, or an antigen binding part of the said region, and
(ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

An embodiment of the invention provides an anti-CD38 antibody of the above embodiments wherein said monovalent antibody is of the IgG4 subtype, but the $C_H3$ region has been modified so that one or more of the following amino acid substitutions have been made: Thr (T) in position 366 has been replaced by Ala (A); Leu (L) in position 368 has been replaced by Ala (A); Leu (L) in position 368 has been replaced by Val (V); Phe (F) in position 405 has been replaced by Ala (A); Phe (F) in position 405 has been replaced by Leu (L); Tyr (Y) in position 407 has been replaced by Ala (A); Arg (R) in position 409 has been replaced by Ala (A).

An embodiment of the invention provides an anti-CD38 antibody of any of the above embodiments, the heavy chain has been modified such that the entire hinge has been deleted.

An embodiment of the invention provides an anti-CD38 antibody of any of the above embodiments, wherein the sequence of said monovalent antibody has been modified so that it does not comprise any acceptor sites for N-linked glycosylation.

An embodiment of the invention provides an antibody according to any of the above embodiments, which inhibits the synthesis of cGDPR by at least 25%, such as at least 30% after 90 minutes as determined by spectophotometric method described in Example 8 of the specification.

An embodiment of the invention provides an antibody according to any of the above embodiments which inhibits the synthesis of cADPR by at least 25%, such as at least 30% after 90 minutes at a concentration of 3 µg/ml as determined by the HPLC method described in Munshi et al., J. Biol. Chem. 275, 21566-21571 (2000).

An embodiment of the invention provides an antibody according to any of the above embodiments, which stimulate the hydrolase activity of CD38 by at least 25%.

An embodiment of the invention provides an antibody according to any of the above embodiments, which stimulate the NAD hydrolase activity by at least 25%.

An embodiment of the invention provides an antibody according to any of the above embodiments, which stimulate the cADPR-hydrolase activity by at least 25%.

An embodiment of the invention provides an isolated nucleic acid encoding a peptide according to the any of the above embodiments.

An embodiment of the invention provides an expression vector comprising a nucleotide sequence encoding one or more of the amino acid sequences according to any of the above embodiments.

An embodiment of the invention provides an expression vector according to the above embodiment, further comprising a nucleotide sequence encoding the constant region of a light chain, a heavy chain or both light and heavy chains of a human antibody.

An embodiment of the invention provides a recombinant eukaryotic or prokaryotic host cell which produces an antibody as defined in any of the above embodiments.

An embodiment of the invention provides a hybridoma which produces an antibody as defined in any of the above embodiments.

An embodiment of the invention provides a pharmaceutical composition comprising an antibody as defined in any of the above embodiments, and a pharmaceutically acceptable carrier.

An embodiment of the invention provides an antibody as defined in any of the embodiments above for use as a medicament.

An embodiment of the invention provides an antibody as defined in any of the embodiments above for use in inhibiting growth and/or proliferation, migration or inducing phagocytosis of a tumor cell expressing CD38.

An embodiment of the invention provides an antibody as defined in any of the embodiments above for use in treating rheumatoid arthritis.

An embodiment of the invention provides an antibody as defined in any of the embodiments above for use in treating multiple myeloma.

An embodiment of the invention provides an antibody as defined in any of the embodiments above for use in treating multiple sclerosis.

An embodiment of the invention provides an antibody as defined in any of the embodiments above for use in treating B-cell neoplasms such as any one of the following: small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma or AIDS-related non-Hodgkins lymphoma An embodiment of the invention provides a method for inhibiting growth and/or proliferation, migration or inducing phagocytosis of a tumor cell expressing CD38, comprising administration, to an individual in need thereof, of an antibody of any of the above embodiments.

An embodiment of the invention provides a method for producing an anti-CD38 antibody of any of the above embodiments, said method comprising the steps of
a) culturing a host cell of claim 52 or a hybridoma of the above embodiment, and
b) purifying the anti-CD38 antibody from the culture media.

An embodiment of the invention provides a diagnostic composition comprising an antibody as defined in any of the above embodiments.

An embodiment of the invention provides a method for detecting the presence of CD38 antigen, or a cell expressing CD38, in a sample comprising:
    contacting the sample with an anti-CD38 antibody of any
       of the above embodiments under conditions that allow
       for formation of a complex between the antibody or
       bispecific molecules and CD38; and
    analyzing whether a complex has been formed.

An embodiment of the invention provides a kit for detecting the presence of CD38 antigen, or a cell expressing CD38, in a sample comprising
    an anti-CD38 antibody of any of the above embodiments or
       and
    instructions for use of the kit.

An embodiment of the invention provides an anti-idiotypic antibody which binds to an anti-CD38 antibody of any of the above embodiments.

An embodiment of the invention provides a method of inhibiting growth and/or proliferation of a cell expressing CD38, comprising administration of a peptide according to any of the above embodiments, an immunoconjugate according to the above embodiment, a pharmaceutical composition according to the above embodiments or an expression vector mentioned in the above embodiments, such that the growth and/or proliferation, migration or phagocytosis of the cell is inhibited.

An embodiment of the invention provides a method of treating a disease or disorder involving cells expressing CD38 in a subject, which method comprises administration of a peptide according to any of the above embodiments, an immunoconjugate according to an embodiment above, a pharmaceutical composition according to an embodiment above, or an expression vector according to any one the embodiments above to a subject in need thereof.

An embodiment of the invention provides a method of preventing a disease or disorder involving cells expressing CD38 in a subject, which method comprises administration of a peptide according to any of the above embodiments, an immunoconjugate according to an embodiment above, a pharmaceutical composition according to an embodiment above, or an expression vector according to any one the embodiments above to a subject in need thereof.

An embodiment of the invention provides a method according to the above embodiments wherein the disease or disorder is rheumatoid arthritis.

An embodiment of the invention provides a method according to the above embodiments wherein the disease or disorder is B-cell neoplasms such as any one of the following: small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma, multiple myeloma, lymphoplasmacytic lymphoma, splenic margina zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

An embodiment of the invention provides a method according to the above embodiments wherein the disease or disorder is multiple myeloma An embodiment of the invention provides a method according to the above embodiments wherein the disease or disorder is autoimmune disease.

An embodiment of the invention provides a method according to the above embodiments wherein the disease or disorder is diabetes.

An embodiment of the invention provides a method according to the above embodiments wherein the disease or disorder is multiple sclerosis.

An embodiment of the invention provides a method according to the above embodiments wherein the disease or disorder is Grave's disease.

An embodiment of the invention provides a method according to the above embodiments wherein the disease or disorder is neuroinflammation.

An embodiment of the invention provides a method according to the above embodiments wherein the disease or disorder is inflammation of airway smooth muscle cells during asthma.

An embodiment of the invention provides a method according to the above embodiments, wherein the method comprises administration of one or more further therapeutic agents to the subject.

An embodiment of the invention provides a method according to the above embodiment, wherein the one or more further therapeutic agents are selected from a chemotherapeutic agent, an anti-inflammatory agent, or an immunosuppressive and/or immunomodulatory agent.

An embodiment of the invention provides a method according to the above embodiment, wherein the one or more further therapeutic agents are selected from a group consisting of cisplatin, gefitinib, cetuximab, rituximab, bevacizumab, erlotinib, bortezomib, thalidomide, pamidronate, zoledronic acid, clodronate, risendronate, ibandronate, etidronate, alendronate, tiludronate, arsenic trioxide, lenalidomide, filgrastim, pegfilgrastim, sargramostim, suberoylanilide hydroxamic acid, and SCIO-469.

Monoclonal antibodies of the present invention may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest.

In one embodiment, the antibody of the invention is a human antibody. Human monoclonal antibodies directed against CD38 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-

851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques.

Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated and identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

Competition for binding to CD38 or a portion of CD38 by two or more anti-CD38 antibodies may be determined by any suitable technique. Competition in the context of the present invention refers to any detectably significant reduction in the propensity for a particular molecule to bind a particular binding partner in the presence of another molecule that binds the binding partner. Typically, competition means an at least about 10% reduction, such as an at least about 15%, or an at least about 20% reduction in binding between an anti-CD38 antibody and (a) a form of CD38 (e.g. "processed", "mature", "unprocessed", "not processed" or "immature" CD38);
(b) a form of free CD38 (e.g., a CD38 fragment produced by in vivo processing);
(c) a heterodimeric peptide composed of another peptide associated with CD38, such as CD31 associated with CD38;
(d) a complex of CD38 and one or more substrates, such as cAMP, NAD+ and/or cADPR;
(e) a dimerized, associated and/or processed dimer of CD38 with a soluble ligand, such as CD31; or
(f) a portion of CD38, caused by the presence of another anti-CD38 antibody as determined by, e.g., ELISA analysis or FACS analysis (as described in the examples section) using sufficient amounts of the two or more competing anti-CD38 antibodies and CD38 molecule. It may also be the case that competition may exist between anti-CD38 antibodies with respect to more than one form of CD38, and/or a portion of CD38, e.g. in a context where the antibody-binding properties of a particular region of CD38 are retained in fragments thereof, such as in the case of a well-presented linear epitope located in various tested fragments or a conformational epitope that is presented in sufficiently large CD38 fragments as well as in CD38.

Assessing competition typically involves an evaluation of relative inhibitory binding using a first amount of a first molecule; a second amount of a second molecule; and a third amount of a third molecule (or a standard determined by binding studies that may be reasonably compared to new binding data with respect to the first and second molecules as a surrogate for actual contemporaneous data), wherein the first, second, and third amounts all are sufficient to make a comparison that imparts information about the selectivity and/or specificity of the molecules at issue with respect to the other present molecules. The first, second, and third amounts may vary with the nature of the anti-CD38 antibody and potential targets therefore at issue. For instance, for ELISA assessments, similar to those described in the Examples section, about 5-50 µg (e.g., about 10-50 µg, about 20-50 µg, about 5-20 µg, about 10-20 µg, etc.) of anti-CD38 antibody and/or CD38 targets are required to assess whether competition exists. Conditions also should be suitable for binding. Typically, physiological or near-physiological conditions (e.g., temperatures of about 20-40° C., pH of about 7-8, etc.) are suitable for anti-CD38 antibody:CD38 binding. Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to CD38 (e.g., the natural binding partners of CD38 such as CD31, also called CD31 antigen, EndoCAM, GPIIA', PECAM-1, platelet/endothelial cell adhesion molecule or naturally occurring anti-CD38 antibody)). Thus, for example, it is possible to set a criterion for competitiveness wherein at least about 10% relative inhibition is detected; at least about 15% relative inhibition is detected; or at least about 20% relative inhibition is detected before an antibody is considered sufficiently competitive. In cases where epitopes belonging to competing antibodies are closely located in an antigen, competition may be marked by greater than about 40% relative inhibition of CD38 binding (e.g., at least about 45% inhibition, such as at least about 50% inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

Competition may be considered the inverse of cross-reactivity between a molecule and two potential binding partners. In certain embodiments, a anti-CD38 antibody of the present invention specifically binds to one or more residues or regions in CD38 but also does not cross-react with other peptides, peptide regions, or molecules, e.g., the present invention provides an anti-CD38 antibody that does not cross-react with proteins with homology to CD38, such as BST-1 (bone marrow stromal cell antigen-1) and Mo5, also called CD157; or anti-CD38 antibodies that do not cross-react with CD38 in the context of normal tissue, such as tissues not involved in multiple myeloma. Typically, a lack of cross-reactivity means less than about 5% relative competitive inhibition between the molecules when assessed by ELISA and/or FACS analysis using sufficient amounts of the molecules under suitable assay conditions.

In one embodiment, the present invention provides an anti-CD38 antibody that competes with an antibody having a $V_L$ sequence of SEQ ID NO: 27 and a $V_H$ sequence of SEQ ID NO: 2, such as the antibody 028, for binding to CD38 or a portion thereof.

In one embodiment, the present invention provides an anti-CD38 antibody that competes with an antibody having a $V_L$ sequence of SEQ ID NO: 32 and a $V_H$ sequence of SEQ ID NO: 7, such as the antibody 025, for binding to CD38 or a portion thereof.

In one embodiment, the present invention provides an anti-CD38 antibody that competes with an antibody having a $V_L$ sequence of SEQ ID NO: 37 and a $V_H$ sequence of SEQ ID NO: 12, such as the antibody 026, for binding to CD38 or a portion thereof.

In one embodiment, the present invention provides an anti-CD38 antibody that competes with an antibody having a $V_L$ sequence of SEQ ID NO: 42 and a $V_H$ sequence of SEQ ID NO: 17, such as the antibody 049, for binding to CD38 or a portion thereof.

In one embodiment, the present invention provides an anti-CD38 antibody that competes with an antibody having a $V_L$ sequence of SEQ ID NO: 47 and a $V_H$ sequence of SEQ ID NO: 22, such as the antibody 056, for binding to CD38 or a portion thereof.

As discussed elsewhere herein, unless otherwise stated or clearly contradicted by context, references to binding of an anti-CD38 antibody to CD38 are intended to refer to binding in any suitable context, such as in a conformational context where the structure of CD38 is present; or in a linear epitope context. Of course, binding in a limited subset of such context(s) may be an important characteristic with respect to any anti-CD38 antibody provided by the present invention.

Additional methods for determining anti-CD38 antibody specificity by competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993), and Muller, Meth. Enzymol. 92, 589-601 (1983)).

Human CD38 comprises a number of different epitopes, which may include (1) peptide antigenic determinants that are comprised within single peptide chains within human CD38; (2) conformational antigenic determinants which consist of one or more noncontiguous amino acids on a particular chain and/or amino acids present on spatially contiguous but separate peptide chains (typically where the respective amino acid sequences of the chains are located disjointedly along the human CD38 polypeptide sequence); (3) post-translational antigenic determinants which consist, either in whole or part, of molecular structures covalently attached to human CD38, such as carbohydrate groups; or (4) combinations of (1)-(3).

An epitope in the context of the present invention includes any peptide or peptide-derivative determinant capable of specific binding to an immunoglobulin. An epitope may comprise any suitable number of amino acids, in any suitable position (with respect to the linear sequence of CD38), orientation (with respect to folded CD38, or a fragment thereof), amino acid composition (and consequently, at least in part, charge). Thus, for example, an epitope may be composed of about 3-10 amino acids, typically 3-8 amino acids, in one or more contiguous or noncontiguous locations with respect to the primary sequence of CD38 (for instance an epitope may consist essentially of 2, 3, 4, 5, 6, 7, or 8 amino acid residues distributed in 1, 2, 3, 4, or 5 noncontiguous locations in CD38). Alternatively, for example, an epitope may be considered to be defined by a region of about 5-40 contiguous amino acid residues (e.g., about 7-30 amino acid residues, about 5-20 amino acid residues, or about 3-15 amino acid residues) in CD38 (solely or in combination with a portion of an adjacent CD38 domain). In some epitopes it may be the case that just one amino acid residue or only a few amino acid residues are critical to CDR or CDR(s) recognition (and thereby most important to anti-CD38 antibody:CD38 antigen affinity and avidity). As such, an epitope may be characterized on the basis of one or more of such critical residues, with the recognition that other residues may also make some lesser contribution to the epitope. In the case of an epitope defined by a region of amino acids, it may be that one or more amino acids in the region make only a minor contribution or even negligible contribution to antibody binding, such that the residue may be subject to substitution with an appropriate different residue without resulting in "a loss" of the epitope to at least some anti-CD38 antibodies specific for it.

In one embodiment, the present invention provides a anti-CD38 antibody, such as an anti-CD38 antibody, that specifically binds to a CD38 epitope that also is specifically bound by an antibody having a $V_L$ sequence of SEQ ID NO: 27 and a $V_H$ sequence of SEQ ID NO: 2 (such as antibody 028), or an antibody having a $V_L$ sequence of SEQ ID NO: 32 and a $V_H$ sequence of SEQ ID NO: 7 (such as antibody 025), or an antibody having a $V_L$ sequence of SEQ ID NO: 37 and a $V_H$ sequence of SEQ ID NO: 12 (such as antibody 026), or an antibody having a $V_L$ sequence of SEQ ID NO: 42 and a $V_H$ sequence of SEQ ID NO: 17 (such as antibody 049), or an antibody having a $V_L$ sequence of SEQ ID NO: 47 and a $V_H$ sequence of SEQ ID NO: 22 (such as antibody 056).

It is possible that anti-CD38 antibodies having one or more CDRs that differ from the CDRs of an antibody having a $V_L$ sequence of SEQ ID NO: 27 and a $V_H$ sequence of SEQ ID NO: 2, or the CDRs of an antibody having a $V_L$ sequence of SEQ ID NO: 32 and a $V_H$ sequence of SEQ ID NO: 7, or the CDRs of an antibody having a $V_L$ sequence of SEQ ID NO: 37 and a $V_H$ sequence of SEQ ID NO: 12, or the CDRs of an antibody having a $V_L$ sequence of SEQ ID NO: 42 and a $V_H$ sequence of SEQ ID NO: 17, or the CDRs of an antibody having a $V_L$ sequence of SEQ ID NO: 47 and a $V_H$ sequence of SEQ ID NO: 22, may still be specific for the same epitope as an antibody having the CDRs of an antibody having a $V_L$ sequence of SEQ ID NO: 27 and a $V_H$ sequence of SEQ ID NO: 2, or the CDRs of an antibody having a $V_L$ sequence of SEQ ID NO: 32 and a $V_H$ sequence of SEQ ID NO: 7, or the CDRs of an antibody having a $V_L$ sequence of SEQ ID NO: 37 and a $V_H$ sequence of SEQ ID NO: 12, or the CDRs of an antibody having a $V_L$ sequence of SEQ ID NO: 42 and a $V_H$ sequence of SEQ ID NO: 17, or the CDRs of an antibody having a $V_L$ sequence of SEQ ID NO: 47 and a $V_H$ sequence of SEQ ID NO: 22, respectively. In such cases, the anti-CD38 antibody in question may recognize or be more specific/selective for particular structures or regions of the epitope than the antibody having the CDRs of an antibody having a $V_L$ sequence of SEQ ID NO: 27 and a $V_H$ sequence of SEQ ID NO: 2, or the CDRs of an antibody having a $V_L$ sequence of SEQ ID NO: 32 and a $V_H$ sequence of SEQ ID NO: 7, or the CDRs of an antibody having a $V_L$ sequence of SEQ ID NO: 37 and a $V_H$ sequence of SEQ ID NO: 12, or the CDRs of an antibody having a $V_L$ sequence of SEQ ID NO: 42 and a $V_H$ sequence of SEQ ID NO: 17, or the CDRs of an antibody having a $V_L$ sequence of SEQ ID NO: 47 and a $V_H$ sequence of SEQ ID NO: 22 respectively.

A CD38 epitope bound by an antibody having a $V_L$ sequence of SEQ ID NO: 27 and a $V_H$ sequence of SEQ ID NO: 2 (such as antibody 028), or an antibody having a $V_L$ sequence of SEQ ID NO: 32 and a $V_H$ sequence of SEQ ID NO: 7 (such as antibody 025), or an antibody having a $V_L$ sequence of SEQ ID NO: 37 and a $V_H$ sequence of SEQ ID NO: 12 (such as antibody 026), or an antibody having a $V_L$ sequence of SEQ ID NO: 42 and a $V_H$ sequence of SEQ ID NO: 17 (such as antibody 049), or an antibody having a $V_L$ sequence of SEQ ID NO: 47 and a $V_H$ sequence of SEQ ID NO: 22 (such as antibody 056), may be identified via standard mapping and characterization techniques, further refinement of which may be identified by any suitable technique, numerous examples of which are available to the skilled artisan.

These techniques may also be used to identify and/or characterize epitopes for anti-CD38 antibodies generally. As one example of such mapping/characterization methods, an epitope for an anti-CD38 antibody may be determined by epitope "foot-printing" using chemical modification of the exposed amines/carboxyls in the CD38 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry. See, e.g., Ehring H, Analytical Biochemistry, 267 (2) 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding may be identified that way. See for instance Ernst Schering Res Found Workshop. (44), 149-67 (2004), Huang et al., Journal of Molecular Biology 281 (1), 61-67 (1998) and Saito and Patterson, Methods. 9 (3), 516-24 (1996).

Epitope mapping/characterization may also be performed using mass spectrometry methods. See for instance Downward, J Mass Spectrom. 35 (4), 493-503 (2000) and Kiselar and Downward, Anal Chem. 71 (9), 1792-801 (1999).

Protease digestion techniques may also be useful in the context of epitope mapping and identification. Antigenic determinant-relevant regions/sequences may be determined by protease digestion, e.g. by using trypsin in a ratio of about 1:50 to CD38 overnight (O/N) digestion at 37° C. and pH 7-8, followed by mass spectrometry (MS) analysis for peptide identification. The peptides protected from trypsin cleavage by the CD38BP may subsequently be identified by comparison of samples subjected to trypsin digestion and samples incubated with CD38BP and then subjected to digestion by e.g. trypsin (thereby revealing a foot-print for the binder). Other enzymes like chymotrypsin, pepsin, etc. may also or alternatively be used in a similar epitope characterization method.

An anti-CD38 antibody which gives the significantly same result as an antibody having a $V_L$ sequence of SEQ ID NO: 27 and a $V_H$ sequence of SEQ ID NO: 2 (such as antibody 028), or an antibody having a $V_L$ sequence of SEQ ID NO: 32 and a $V_H$ sequence of SEQ ID NO: 7 (such as antibody 025), or an antibody having a $V_L$ sequence of SEQ ID NO: 37 and a $V_H$ sequence of SEQ ID NO: 12 (such as antibody 026), or an antibody having a $V_L$ sequence of SEQ ID NO: 42 and a $V_H$ sequence of SEQ ID NO: 17 (such as antibody 049), or an antibody having a $V_L$ sequence of SEQ ID NO: 47 and a $V_H$ sequence of SEQ ID NO: 22 (such as antibody 056), in these measurements are deemed to be an antibody that bind the same epitope as an antibody having a $V_L$ sequence of SEQ ID NO: 27 and a $V_H$ sequence of SEQ ID NO: 2 (such as antibody 028), or an antibody having a $V_L$ sequence of SEQ ID NO: 32 and a $V_H$ sequence of SEQ ID NO: 7 (such as antibody 025), or an antibody having a $V_L$ sequence of SEQ ID NO: 37 and a $V_H$ sequence of SEQ ID NO: 12 (such as antibody 026), or an antibody having a $V_L$ sequence of SEQ ID NO: 42 and a $V_H$ sequence of SEQ ID NO: 17 (such as antibody 049), or an antibody having a $V_L$ sequence of SEQ ID NO: 47 and a $V_H$ sequence of SEQ ID NO: 22 (such as antibody 056), respectively. See for instance Manca, Ann Ist Super Sanita. 27 (1), 15-9 (1991) for a discussion of similar techniques.

Epitope mapping by competitive binding to CD38 with two antibodies where one is biotinylated is another method for identifying relevant antigenic determinant regions. The binding of antibodies to linear and looped peptides of CD38 by a PEPSCAN-based enzyme-linked immuno assay is another method for identifying relevant antigenic determinant regions, see for instance Slootstra-J W et al. Mol-Divers. 1, 87-96 (1996).

Site directed mutagenesis is another method for identifying relevant antigenic determinant regions, see for instance Polyak and Deans, Blood 99, 3956-3962 (2002). Various phage display techniques may also be used to identify epitopes. See for instance Wang and Yu, Curr Drug Targets. 5(1), 1-15 (2004), Burton, Immunotechnology. 1(2), 87-94 (1995 August), Cortese et al., Immunotechnology. 1(2), 87-94 (1995) and Irving et al., Curr Opin Chem Biol. 5(3), 314-24 (2001). Consensus epitopes may also be identified through modified phage display-related techniques (see, www.cs.montana.edu/~mumey/papers/jcb03.pdf) for discussion.

Other methods potentially helpful in mapping epitopes include crystallography techniques, X-ray diffraction techniques (such as the X-ray diffraction/sequence study techniques developed by Poljak and others in the 1970s-1980s), and the application of Multipin Peptide Synthesis Technology. Computer-based methods such as sequence analysis and three dimensional structure analysis and docking may also be used to identify antigenic determinants. For example, an epitope may also be determined by molecular modeling using a structure of CD38 with docking of the structure of the Fab fragment of the individual monoclonal antibody. These and other mapping methods are discussed in Epitope Mapping A Practical Approach (Westwood and Hay Eds.) 2001 Oxford University Press.

In one embodiment, the present invention provides an anti-CD38 antibody having substantially the same specific CD38-binding characteristics of one or more mAbs selected from an antibody having a $V_L$ sequence of SEQ ID NO: 27 and a $V_H$ sequence of SEQ ID NO: 2 (such as antibody 028), or an antibody having a $V_L$ sequence of SEQ ID NO: 32 and a $V_H$ sequence of SEQ ID NO: 7 (such as antibody 025), or an antibody having a $V_L$ sequence of SEQ ID NO: 37 and a $V_H$ sequence of SEQ ID NO: 12 (such as antibody 026), or an antibody having a $V_L$ sequence of SEQ ID NO: 42 and a $V_H$ sequence of SEQ ID NO: 17 (such as antibody 049), or an antibody having a $V_L$ sequence of SEQ ID NO: 47 and a $V_H$ sequence of SEQ ID NO: 22 (such as antibody 056).

Mapping studies have indicated that several monoclonal antibodies raised against human CD38 bind to epitopes in the C-terminal region of CD38 (220-296) (Hoshino et al. and Ferrero et al.). Within this region three amino acid differences have been found between the human and the cynomolgus CD38 sequence: T237, Q272 and S274 in humans correspond to A238, R273 and F275 in cynomolgus. A limited number of amino acid differences exist between the human and the monkey CD38 sequence, for instance in the carboxyterminal part to the protein, for instance the following three amino acid differences between the human and the cynomolgus CD38 sequence: T237, Q272 and S274 in human CD38s correspond to A238, R273 and F275 in cynomolgus monkey CD38 (compare SEQ ID No. 21 and SEQ ID No. 22).

The antibodies of the present invention do not bind to human CD38 mutants wherein aspartic acid in position 202 has been substituted with a glycine to the same degree that it binds to human CD38. The present invention provides antibodies, which bind to human CD38 and which binds to a mutant human CD38, wherein the serine residue in position 274 has been substituted with a phenylalanine residue. The antibodies of the present invention also bind to human CD38 mutants wherein glutamine in position 272 has been substituted with an arginine. The antibodies of the present invention also bind to human CD38 mutants wherein the threonine in position 237 has been substituted with an alanine.

The term "do not bind to the same degree" should be interpreted so that the binding of the antibody to the mutant human CD38 is significantly lower than the binding of the antibody to the wild type human CD38. The term "bind to the same degree" should be interpreted so that the binding of the antibody to the mutant human CD38 is substantially of the same order as the binding of the antibody to the wild type human CD38. The binding of a peptide to the CD38 molecules (wild type and mutant) may be determined in a number of ways and it is within the common general knowledge of a person skilled in the art to determine whether the binding to the mutant is "significantly lower" than the binding to the wild type. A large number of different techniques for determining the binding of a peptide to another peptide are available to the person skilled in the art, for example ELISA, radioimmunoassay, BIAcore or flow cytometry.

One method of determining the binding is by determining the $EC_{50}$ of the binding of the antibody to the mutant protein and to the wild type protein and then comparing the values obtained. Another method of determining the binding is by examining the magnitude of binding at saturating concentration (for instance the plateau of binding signal), or by determining kinetic rate constants $k_{on}$ and $k_{off}$ for example by BIAcore.

In one embodiment, the binding of the antibody in question to the CD38 proteins (mutant or wild type) is by use of an ELISA as described in Example 4.

In a further embodiment, the antibody of the invention comprises a human heavy chain variable region (VH) CDR3 sequence comprising:
  an amino acid sequence selected from the group consisting of: SEQ ID NOs: 5, 10, 15, 20 and 25, or
  a variant of any of said sequences, wherein said variant preferably only has conservative amino acid modifications.

In one embodiment, said variant consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 5, 10, 15, 20 and 25.

In a further embodiment, said variant has at most 1, 2 or 3 amino-acid modifications, e.g. amino acid substitutions, preferably conservative substitutions as compared to said sequence.

In a preferred embodiment, said antibody comprises a human heavy chain variable region CDR3 sequence comprising an amino acid sequence selected from the group consisting of: SEQ ID NOs: 5, 10, 15, 20 and 25.

In an even further embodiment, the antibody of the invention comprises:
  a VH region comprising the CDR1, 2 and 3 sequences of SEQ ID NO: 3, 4 and 5; or
  a VH region comprising the CDR1, 2 and 3 sequences of SEQ ID NO: 8, 9 and 10; or
  a VH region comprising the CDR1, 2 and 3 sequences of SEQ ID NO: 13, 14 and 15; or
  a VH region comprising the CDR1, 2 and 3 sequences of SEQ ID NO: 18, 19 and 20; or
  a VH region comprising the CDR1, 2 and 3 sequences of SEQ ID NO: 23, 24 and 25; or
  a variant of any said VH regions, wherein said variant preferably only has conservative amino-acid substitutions.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 3, 8, 13, 18 or 23.

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 9, 14, 19 or 24.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 5, 10, 15, 20 or 25.

In another embodiment, the antibody the antibody comprises
a) a VL CDR3 region having the sequence as set forth in SEQ ID NO: 30 and a VH CDR3 region having a sequence selected from the group consisting of SEQ ID NO: 5,
b) a VL CDR3 region having the sequence as set forth in SEQ ID NO: 35 and a VH CDR3 region having the sequence as set forth in SEQ ID NO: 10,
c) a VL CDR3 region having the sequence as set forth in SEQ ID NO: 40 and a VH CDR3 region having the sequence as set forth in SEQ ID NO: 15,
d) a VL CDR3 region having the sequence as set forth in SEQ ID NO: 45 and a VH CDR3 region having the sequence as set forth in SEQ ID NO: 20,
e) a VL CDR3 region having the sequence as set forth in SEQ ID NO: 50 and a VH CDR3 region having the sequence as set forth in SEQ ID NO: 25,
f) a variant of any of the above, wherein said variant preferably only has conservative substitutions in said sequences In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 5, 10, 15, 20 or 25. In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 30, 35, 40, 45 or 50;

In a further embodiment, the antibody of the invention comprises:
a VH region comprising the CDR1, 2 and 3 sequences of SEQ ID NO: 3, 4 and 5, and a VL region comprising the CDR3 sequence of SEQ ID NO: 30; or
a VH region comprising the CDR1, 2 and 3 sequences of SEQ ID NO: 8, 9 and 10, and a VL region comprising the CDR3 sequence of SEQ ID NO: 35; or
a VH region comprising the CDR1, 2 and 3 sequences of SEQ ID NO: 13, 14 and 15, and a VL region comprising the CDR3 sequence of SEQ ID NO: 40; or
a VH region comprising the CDR1, 2 and 3 sequences of SEQ ID NO: 18, 19 and 20, and a VL region comprising the CDR3 sequence of SEQ ID NO: 45; or
a VH region comprising the CDR1, 2 and 3 sequences of SEQ ID NO: 23, 24 and 25, and a VL region comprising the CDR3 sequence of SEQ ID NO: 50; or
a variant of any of said antibodies, wherein said variant preferably only has conservative amino-acid substitutions in said sequences.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 3, 8, 13, 18 or 23.

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 9, 14, 19 or 24.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 5, 10, 15, 20 or 25.

In one embodiment, said variant comprises a VL CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 28, 33, 38, 43 or 48.

In one embodiment, said variant comprises a VL CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 29, 34, 39, 44 or 49.

In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 30, 35, 40, 45, or 50.

In a further embodiment, the antibody of the invention comprises:
a VH region comprising the CDR1, 2 and 3 sequences of SEQ ID NO: 3, 4 and 5 and a VL region comprising the CDR1, 2 and 3 sequences of SEQ ID NO: 28, 29 and 30; or
a VH region comprising the CDR1, 2 and 3 sequences of SEQ ID NO: 8, 9 and 10 and a VL region comprising the CDR1, 2 and 3 sequences of SEQ ID NO: 33, 34 and 35; or
a VH region comprising the CDR1, 2 and 3 sequences of SEQ ID NO: 13, 14 and 15 and a VL region comprising the CDR1, 2 and 3 sequences of SEQ ID NO: 38, 39 and 40; or
a VH region comprising the CDR1, 2 and 3 sequences of SEQ ID NO: 18, 19 and 20 and a VL region comprising the CDR1, 2 and 3 sequences of SEQ ID NO: 43, 44 and 45; or
a VH region comprising the CDR1, 2 and 3 sequences of SEQ ID NO: 23, 24 and 25 and a VL region comprising the CDR1, 2 and 3 sequences of SEQ ID NO: 48, 49 and 50; or a variant of any of said antibodies, wherein said variant preferably only has conservative amino acid modifications in said sequences.

In one embodiment, said variant comprises a VH CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 3, 8, 13, 18 or 23;

In one embodiment, said variant comprises a VH CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 4, 9, 14, 19 or 24.

In one embodiment, said variant comprises a VH CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 5, 10, 15, 20 or 25.

In one embodiment, said variant comprises a VL CDR1 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 28, 33, 38, 43 or 48.

In one embodiment, said variant comprises a VL CDR2 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 29, 34, 39, 44 or 49.

In one embodiment, said variant comprises a VL CDR3 which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 30, 35, 40, 45 or 50.

In an even further embodiment, the antibody of the invention comprises:
 a VH region comprising the sequence of SEQ ID NO: 2 and a VL region comprising the sequence of SEQ ID NO: 27; or
 a VH region comprising the sequence of SEQ ID NO: 7 and a VL region comprising the sequence of SEQ ID NO: 32; or
 a VH region comprising the sequence of SEQ ID NO: 12 and a VL region comprising the sequence of SEQ ID NO: 37; or
 a VH region comprising the sequence of SEQ ID NO: 17 and a VL region comprising the sequence of SEQ ID NO: 42; or
 a VH region comprising the sequence of SEQ ID NO: 22 and a VL region comprising the sequence of SEQ ID NO: 47; or
 a variant of any of the above, wherein said variant preferably only has conservative modifications.

In one embodiment, said variant comprises a VH region which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos: 2, 7, 12, 17 or 22.

In one embodiment, said variant comprises a VL region which consists essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID NO: 27, 32, 37, 42 or 47.

In a further embodiment the antibody of the present invention comprises a VH having at least 80% identity, such as 90%, or 95%, or 97%, or 98%, or 99% identity to a VH region sequence selected from the group consisting of: SEQ ID NO: 2, 7, 12, 17 or 22.

In a further embodiment the antibody of the present invention comprises a VL having at least 80% identity, such as 90%, or 95%, or 97%, or 98%, or 99% identity to a VL region sequence selected from the group consisting of: SEQ ID NO: 27, 32, 37, 42 or 47.

In an even further embodiment, the antibody of the invention comprises a VH region selected from the group consisting of: SEQ ID NO: 2, 7, 12, 17 or 22.

In an even further embodiment, the antibody of the invention comprises a VL region selected from the group consisting of: SEQ ID NO: 27, 32, 37, 42 or 47.

In an even further embodiment, the antibody of the invention comprises:
 a VH region comprising the sequence of SEQ ID NO: 2 and a VL region comprising the sequence of SEQ ID NO: 27; or
 a VH region comprising the sequence of SEQ ID NO: 7 and a VL region comprising the sequence of SEQ ID NO: 32; or
 a VH region comprising the sequence of SEQ ID NO: 12 and a VL region comprising the sequence of SEQ ID NO: 37; or
 a VH region comprising the sequence of SEQ ID NO: 17 and a VL region comprising the sequence of SEQ ID NO: 42; or
 a VH region comprising the sequence of SEQ ID NO: 22 and a VL region comprising the sequence of SEQ ID NO: 47; or The present invention also, in one aspect, provides anti-CD38 antibodies which are characterized with respect to their ability to compete with an antibody having:
 a VH region comprising the sequence of SEQ ID NO: 2 and a VL region comprising the sequence of SEQ ID NO: 27; or
 a VH region comprising the sequence of SEQ ID NO: 7 and a VL region comprising the sequence of SEQ ID NO: 32; or
 a VH region comprising the sequence of SEQ ID NO: 12 and a VL region comprising the sequence of SEQ ID NO: 37; or a VH region comprising the sequence of SEQ ID NO: 17 and a VL region comprising the sequence of SEQ ID NO: 42; or a VH region comprising the sequence of SEQ ID NO: 22 and a VL region comprising the sequence of SEQ ID NO: 47.

The present invention also relates to provides anti-CD38 antibodies which bind to the same epitope as an antibody having:

a VH region comprising the sequence of SEQ ID NO: 2 and a VL region comprising the sequence of SEQ ID NO: 27; or a VH region comprising the sequence of SEQ ID NO: 7 and a VL region comprising the sequence of SEQ ID NO: 32; or a VH region comprising the sequence of SEQ ID NO: 12 and a VL region comprising the sequence of SEQ ID NO: 37; or a VH region comprising the sequence of SEQ ID NO: 17 and a VL region comprising the sequence of SEQ ID NO: 42; or a VH region comprising the sequence of SEQ ID NO: 22 and a VL region comprising the sequence of SEQ ID NO: 47.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-CD38 antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In one embodiment, the antibody of the invention is a full-length antibody. In another embodiment, the antibody of the invention is an antibody fragment or a single-chain antibody.

Antibody fragments may e.g. be obtained by fragmentation using conventional techniques, and the fragments screened for utility in the same manner as described herein for whole antibodies. For example, F(ab')$_2$ fragments may be generated by treating antibody with pepsin. The resulting F(ab')$_2$ fragment may be treated to reduce disulfide bridges to produce Fab' fragments. Fab fragments may be obtained by treating an IgG antibody with papain; Fab' fragments may be obtained with pepsin digestion of IgG antibody. A F(ab') fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating a F(ab')$_2$ fragment with a reducing agent, such as dithiothreitol. Antibody fragments may also be generated by expression of nucleic acids encoding such fragments in recombinant cells (see for instance Evans et al., J. Immunol. Meth. 184, 123-38 (1995)). For example, a chimeric gene encoding a portion of a F(ab')$_2$ fragment could include DNA sequences encoding the C$_H$1 domain and hinge region of the H chain, followed by a translational stop codon to yield such a truncated antibody fragment molecule.

In one embodiment, the anti-CD38 antibody is a monovalent antibody, preferably a monovalent antibody as described in WO2007059782 (Genmab) (incorporated herein by reference). Accordingly, in one embodiment, the antibody is a monovalent antibody, wherein said anti-CD38 antibody is constructed by a method comprising:

i) providing a nucleic acid construct encoding the light chain of said monovalent antibody, said construct comprising a nucleotide sequence encoding the VL region of a selected antigen specific anti-CD38 antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;

iii) providing a cell expression system for producing said monovalent antibody;

iv) producing said monovalent antibody by co-expressing the nucleic acid constructs of (i) and (ii) in cells of the cell expression system of (iii).

Similarly, in one embodiment, the anti-CD38 antibody is a monovalent antibody, which comprises (i) a variable region of an antibody of the invention as described herein or an antigen binding part of the said region, and (ii) a C$_H$ region of an immunoglobulin or a fragment thereof comprising the C$_H$2 and C$_H$3 regions, wherein the C$_H$ region or fragment thereof has been modified such that the region corresponding to the hinge region and, if the immunoglobulin is not an IgG4 subtype, other regions of the C$_H$ region, such as the C$_H$3 region, do not comprise any amino acid residues, which are capable of forming disulfide bonds with an identical C$_H$ region or other covalent or stable non-covalent inter-heavy chain bonds with an identical C$_H$ region in the presence of polyclonal human IgG.

In a further embodiment, the heavy chain of the monovalent anti-CD38 antibody has been modified such that the entire hinge has been deleted.

In a further embodiment, said monovalent antibody is of the IgG4 subtype, but the C$_H$3 region has been modified so that one or more of the following amino acid substitutions have been made: Thr (T) in position 366 has been replaced by Ala (A); Leu (L) in position 368 has been replaced by Ala (A);

Leu (L) in position 368 has been replaced by Val (V); Phe (F) in position 405 has been replaced by Ala (A); Phe (F) in position 405 has been replaced by Leu (L); Tyr (Y) in position 407 has been replaced by Ala (A); Arg (R) in position 409 has been replaced by Ala (A).

In another further embodiment, the sequence of said monovalent antibody has been modified so that it does not comprise any acceptor sites for N-linked glycosylation.

Anti-CD38 antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-CD38 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment, the anti-CD38 antibody of the invention is an effector-function-deficient antibody. Such antibodies are particularly useful when the antibody is for use in stimulation and demping of the immune system through blocking of the inhibitory effects of CD38. For such applications, it may be advantageous that the antibody has no effector functions, such as ADCC, as this may lead to undesired cytotoxicity.

In one embodiment, the effector-function-deficient anti-CD38 antibody is a stabilized IgG4 antibody. Examples of suitable stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386 (Kirin)). Preferably, said antibody comprises a Lys or Ala residue at the position corresponding to 409 or the CH3 region of the antibody has been replaced by the CH3 region of human IgG1, of human IgG2 or of human IgG3.

In a further embodiment, the stabilized IgG4 anti-CD38 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys (SEQ ID NO: 53) sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In an even further embodiment. the stabilized IgG4 anti-CD38 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys (SEQ ID NO: 53) sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient anti-CD38 antibody is an antibody of a non-IgG4 type, e.g. IgG1, IgG2 or IgG3 which has been mutated such that the ability to mediate effector functions, such as ADCC, has been reduced or even eliminated. Examples of such mutations have e.g. been described in Dall'Acqua W F et al., J. Immunol. 177 (2):1129-1138 (2006) and Hezareh M, J. Virol.; 75 (24): 12161-12168 (2001).

Conjugates

In a further embodiment. the antibody of the invention is conjugated to another moiety, such as a cytotoxic moiety, a radioisotope or a drug.

Such antibodies may be produced by chemically conjugating the other moiety to the N-terminal side or C-terminal side of the anti-CD38 antibody or fragment thereof (e.g., an anti-CD38 antibody H chain, L chain, or anti-CD38 specific/selective fragment thereof) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

Anti-CD38 antibodies described herein may also be modified by inclusion of any suitable number of modified amino acids. Suitability in this context is generally determined by the ability to at least substantially retain CD38 selectivity and/or specificity associated with the non-derivatized parent anti-CD38 antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On Cd-Rom, Humana Press, Towata, N.J.

Anti-CD38 antibodies may also be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546.

In one embodiment, the present invention provides an anti-CD38 antibody that is conjugated to a second molecule that is selected from a radionuclide, an enzyme, an enzyme substrate, a cofactor, a fluorescent marker, a chemiluminescent marker, a peptide tag, or a magnetic particle. In one embodiment, an anti-CD38 antibody may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to an anti-CD38 antibody of the present invention. One example of indirect coupling of a second agent is coupling by a spacer moiety.

In one embodiment, anti-CD38 antibodies comprising one or more radiolabeled amino acids are provided. A radiolabeled anti-CD38 antibody may be used for both diagnostic and therapeutic purposes (conjugation to radiolabeled molecules is another possible feature). Nonlimiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. Pat. No. RE 35,500), U.S. Pat. No. 5,648,471 and U.S. Pat. No. 5,697,902.

In one embodiment, the anti-CD38 antibody of the invention is conjugated to a radioisotope or to a radioisotope-containing chelate. For example, the anti-CD38 antibody can be conjugated to a chelator linker, e.g. DOTA, DTPA or tiuxetan, which allows for the anti-CD38 antibody to be complexed with a radioisotope. The anti-CD38 antibody may also or alternatively comprise or be conjugated to one or more radiolabeled amino acids or other radiolabeled molecule. A radiolabeled anti-CD38 antibody may be used for both diagnostic and therapeutic purposes. Non-limiting examples of radioisotopes include 3H, 14C, 15N, 35S, 90Y, 99Tc, 125I, 111In, 131I, 186Re, 213Bs, 225Ac and 227Th.

In one embodiment, the anti-CD38 antibody of the invention is conjugated to auristatins or auristatin peptide analogs and derivates (U.S. Pat. No. 5,635,483; U.S. Pat. No. 5,780,588). Auristatins have been shown to interfere with microtubule dynamics, GTP hydrolysis and nuclear and cellular division (Woyke et al (2001) Antimicrob. Agents and Chemother. 45(12):3580-3584) and have anticancer (U.S. Pat. No. 5,663, 149) and antifungal activity (Pettit et al., (1998) Antimicrob. Agents and Chemother. 42:2961-2965. The auristatin drug moiety may be attached to the antibody, via an linker, through the N (amino) terminus or the C (terminus) of the peptidic drug moiety.

Exemplary auristatin embodiments include the N-terminus-linked monomethyl auristatin drug moieties DE and DF, disclosed in Senter et al., Proceedings of the American Association for Cancer Research. Volume 45, abstract number 623, presented Mar. 28, 2004 and described in US 2005/0238648).

An exemplary auristatin embodiment is MMAE (monomethyl auristatin E), wherein the wavy line indicates the covalent attachment to the linker (L) of an antibody drug conjugate:

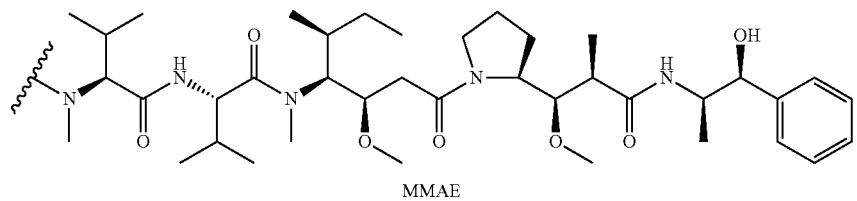 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

Another exemplary auristatin embodiment is MMAF (monomethyl auristatin F), wherein the wavy line indicates the covalent attachment to a linker (L) of an antibody drug conjugate (US2005/0238649):

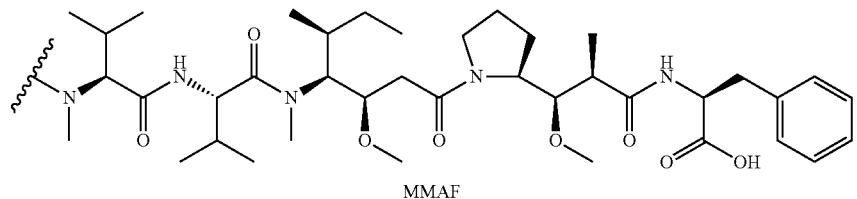

MMAF

The anti-CD38 antibody drug conjugates according to the invention comprise a linker unit between the cytostatic drug unit and the antibody unit. In some embodiments, the linker is cleavable under intracellular conditions, such that the cleavage of the linker releases the drug unit from the antibody in the intracellular environment. In yet another embodiment, the linker unit is not cleavable and the drug is for instance released by antibody degradation. In some embodiments, the linker is cleavable by a cleavable agent that is present in the intracellular environment (e.g. within a lysosome or endosome or caveola). The linker can be, e.g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e.g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker). An advantage of using intracellular proteolytic release of the therapeutic agent is that the agent is typically attenuated when conjugated and the serum stabilities of the conjugates are typically high.

In yet another embodiment, the linker unit is not cleavable and the drug is released by antibody degradation (see US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of antibody drug conjugate compound, are cleaved when the antibody drug conjugate compound presents in an extracellular environment (e.g. plasma). Whether a linker is not substantially sensitive to the extracellular environment can be determined for example by incubating with plasma the antibody drug conjugate compound for a predetermined time period (e.g. 2, 4, 8, 16 or 24 hours) and then quantitating the amount of free drug present in the plasma.

Additional exemplary embodiments comprising MMAE or MMAF and various linker components have the following structures (wherein Ab means antibody and p, representing the drug-loading (or average number of cytostatic drugs per molecule), is 1 to about 8).

Examples where a cleavable linker is combined with an auristatin include vcMMAF and vcMMAE (vc is the abbreviation for the Val-Cit (valine-citruline) based linker):

DAR). The cytostatic drug loading may range from 1 to 20 drug moieties per antibody and may occur on amino acids with useful functional groups such as, but not limited to, amino or sulfhydryl groups, as in lysine or cysteine.

Depending on the way of conjugation, p may be limited by the number of attachment sites on the antibody, for example where the attachment is a cysteine thiol, as in the present invention. Generally, antibodies do not contain many free and reactive cysteine thiol groups which may be linked to a drug moiety as most cysteine thiol residues in antibodies exist as disulfide bridges. Therefore, in certain embodiments, an antibody may be reduced with reducing agent such as dithiothreitol (DTT) or tricarbonylethylphosphine (TCEP), under partial or fully reducing conditions, to generate reactive cysteine thiol groups. In certain embodiments, the drug loading for an ADC of the invention ranges from 1 to about 8, as a maximum of 8 free cysteine thiol groups becomes available after (partial) reduction of the antibody (there are 8 cysteines involved in inter-chain disulfide bonding).

In one embodiment, the drug linker moiety is vcMMAE. The vcMMAE drug linker moiety and conjugation methods are disclosed in WO2004010957, U.S. Pat. No. 7,659,241, U.S. Pat. No. 7,829,531, U.S. Pat. No. 7,851,437 and U.S. Ser. No. 11/833,028 (Seattle Genetics, Inc.), (which are incorporated herein by reference), and the vcMMAE drug linker moiety is bound to the anti-CD38 antibodies at the cysteines using a method similar to those disclosed in therein.

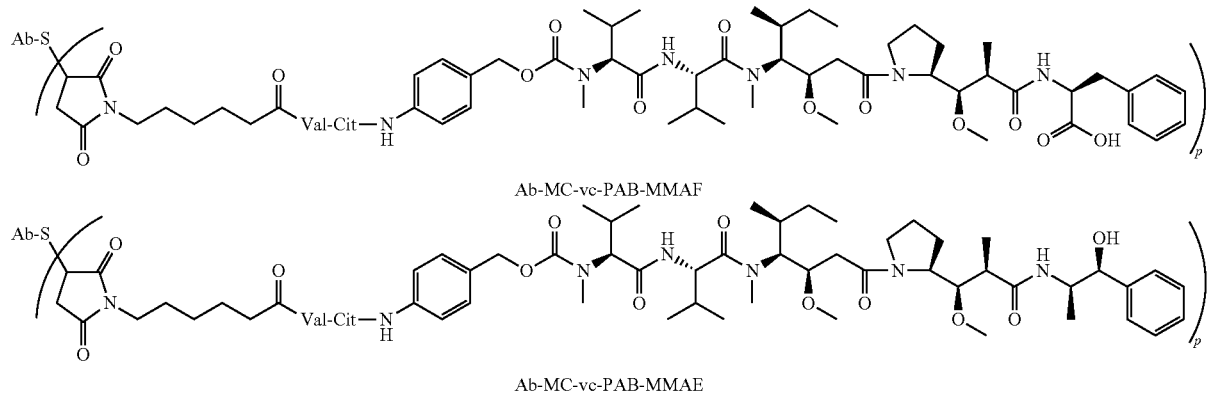

Ab-MC-vc-PAB-MMAF

Ab-MC-vc-PAB-MMAE

Other examples include auristatins combined with a non-cleavable linker, such as mcMMAF. (mc is an abbreviation of maleimido caproyl):

In one embodiment, the drug linker moiety is mcMMAF. The mcMMAF drug linker moiety and conjugation methods are disclosed in U.S. Pat. No. 7,498,298, U.S. Ser. No.

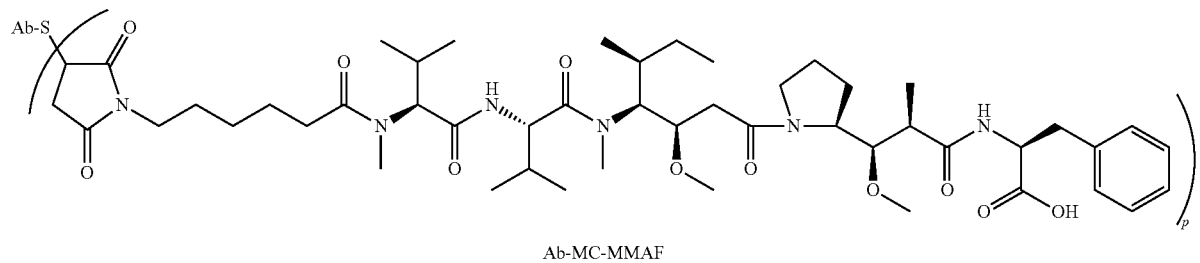

Ab-MC-MMAF

The cytostatic drug loading is represented by p and is the average number of cytostatic drug moieties per antibody in a molecule (also designated as the drug to antibody ratio, 11/833,954, and WO2005081711 (Seattle Genetics, Inc.) (which are incorporated herein by reference), and the mcMMAF drug linker moiety is bound to the anti-CD38 antibodies at the cysteines using a method similar to those disclosed in therein.

Upon purifying the anti-CD38 antibody drug conjugates they may be formulated into pharmaceutical compositions using well known pharmaceutical carriers or excipients.

In one embodiment, an anti-CD38 antibody is conjugated to a functional nucleic acid molecule. Functional nucleic acids include antisense molecules, interfering nucleic acid molecules (e.g., siRNA molecules), aptamers, ribozymes, triplex forming molecules, and external guide sequences. External guide sequences (EGSs) are molecules that bind a target nucleic acid molecule forming a complex that is recognized by RNase P, which cleaves the target molecule. The functional nucleic acid molecules may act as effectors, inhibitors, modulators, and stimulators of a specific activity possessed by a target molecule, or the functional nucleic acid molecules may possess a de novo activity independent of any other molecules. A representative sample of methods and techniques which aid in the design and use of antisense molecules may be found in the following non-limiting list of US patents: U.S. Pat. No. 5,135,917, U.S. Pat. No. 5,294,533, U.S. Pat. No. 5,627,158, U.S. Pat. No. 5,641,754, U.S. Pat. No. 5,691,317, U.S. Pat. No. 5,780,607, U.S. Pat. No. 5,786,138, U.S. Pat. No. 5,849,903, U.S. Pat. No. 5,856,103, U.S. Pat. No. 5,919,772, U.S. Pat. No. 5,955,590, U.S. Pat. No. 5,990,088, U.S. Pat. No. 5,994,320, U.S. Pat. No. 5,998,602, U.S. Pat. No. 6,005,095, U.S. Pat. No. 6,007,995, U.S. Pat. No. 6,013,522, U.S. Pat. No. 6,017,898, U.S. Pat. No. 6,018,042, U.S. Pat. No. 6,025,198, U.S. Pat. No. 6,033,910, U.S. Pat. No. 6,040,296, U.S. Pat. No. 6,046,004, U.S. Pat. No. 6,046,319 and U.S. Pat. No. 6,057,437.

Any method known in the art for conjugating the anti-CD38 antibody to the conjugated molecule(s), such as those described above, may be employed, including those methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Linkage/conjugation may be accomplished in any suitable way. For example, a covalent linkage may take the form of a disulfide bond (if necessary and suitable, an anti-CD38 antibody could be engineered to contain an extra cysteine codon. A toxin molecule, derivatized with a sulfhydryl group reactive with the cysteine of the modified anti-CD38 antibody, may form an immunoconjugate with the anti-CD38 antibody. Alternatively, a sulfhydryl group may be introduced directly to an anti-CD38 antibody using solid phase polypeptide techniques. For example, the introduction of sulfhydryl groups into peptides is described by Hiskey, Peptides 3, 137 (1981). The introduction of sulfhydryl groups into proteins is described in Maasen et al., Eur. J. Biochem. 134, 32 (1983).

Numerous types of cytotoxic compounds may be joined to proteins through the use of a reactive group on the cytotoxic compound or through the use of a cross-linking agent. A common reactive group that will form a stable covalent bond in vivo with an amine is isothiocyanate (Means et al., Chemical modifications of proteins (Holden-Day, San Francisco 1971) pp. 105-110). This group preferentially reacts with the E-amine group of lysine. Maleimide is a commonly used reactive group to form a stable in vivo covalent bond with the sulfhydryl group on cysteine (Ji., Methods Enzymol 91, 580-609 (1983)). Monoclonal antibodies typically are incapable of forming covalent bonds with radiometal ions, but they may be attached to the antibody indirectly through the use of chelating agents that are covalently linked to the antibodies. Chelating agents may be attached through amines (Meares et al., Anal. Biochem. 142, 68-78 (1984)) and sulfhydral groups (Koyama, Chem. Abstr. 120, 217262t (1994)) of amino acid residues and also through carbohydrate groups (Rodwell et al., PNAS USA 83, 2632-2636 (1986), Quadri et al., Nucl. Med. Biol. 20, 559-570 (1993)). A therapeutic or diagnostic agent may also or alternatively be attached at the hinge region of a reduced antibody component via disulfide bond formation.

In one embodiment, the present invention provides an anti-CD38 antibody, such as a human anti-CD38 antibody, conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins". A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin toxins, calicheamicins and duocarmycins. Therapeutic agents, which may be administered in combination with a an anti-CD38 antibody of the present invention as described elsewhere herein, may also be candidates for therapeutic moieties useful for conjugation to an anti-CD38 antibody of the present invention.

As indicated above, the drug moiety need not be construed as limited to classical chemical therapeutic agents. For example, the drug moiety may be a protein or polypeptide possessing a desired biological activity. In one embodiment, the anti-CD38 antibody of the present invention is attached to a chelator linker, e.g. tiuxetan, which allows for the antibody to be conjugated to a radioisotope.

Bispecific Antibodies

In a further aspect, the invention relates to a bispecific molecule comprising a first antigen binding site from an anti-CD38 antibody of the invention as described herein above and a second antigen binding site with a different binding specificity, such as a binding specificity for a human effector cell, a human Fc receptor, a T cell receptor, a B cell receptor or a binding specificity for a non-overlapping epitope of CD38, i.e. a bispecific antibody wherein the first and second antigen binding sites do not cross-block each other for binding to CD38, e.g. when tested as described in Example 3.

Exemplary bispecific antibody molecules of the invention comprise (i) two antibodies, one with a specificity to CD38 and another to a second target that are conjugated together, (ii) a single antibody that has one chain or arm specific to CD38 and a second chain or arm specific to a second molecule, (iii) a single chain antibody that has specificity to CD38 and a second molecule, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fc-region; and (x) a diabody. In one embodiment, the bispecific antibody of the present invention is a diabody, a cross-body, or a bispecific obtained via a controlled Fab arm exchange as those described in the present invention.

Examples of platforms useful for preparing bispecific antibodies include but are not limited to BiTE (Micromet), DART (MacroGenics), Fcab and Mab$^2$ (F-star), Fc-engineered IgG1 (Xencor) or DuoBody (based on Fab arm exchange, Genmab, this application).

Examples of different classes of bispecific antibodies include but are not limited to
- asymmetric IgG-like molecules, wherein the one side of the molecule contains the Fab region or part of the Fab region of at least one antibody, and the other side of the molecule contains the Fab region or parts of the Fab region of at least one other antibody; in this class, asymmetry in the Fc region could also be present, and be used for specific linkage of the two parts of the molecule;
- symmetric IgG-like molecules, wherein the two sides of the molecule each contain the Fab region or part of the Fab region of at least two different antibodies;
- IgG fusion molecules, wherein full length IgG antibodies are fused to extra Fab regions or parts of Fab regions;
- Fc fusion molecules, wherein single chain Fv molecules or stabilized diabodies are fused to Fcγ regions or parts thereof;
- Fab fusion molecules, wherein different Fab-fragments are fused together;
- ScFv- and diabody-based molecules wherein different single chain Fv molecules or different diabodies are fused to each other or to another protein or carrier molecule.

Examples of asymmetric IgG-like molecules include but are not limited to the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (EMD Serono), the Biclonic (Merus) and the DuoBody (Genmab A/S).

Example of symmetric IgG-like molecules include but are not limited to Dual Targeting (DT)-Ig (GSK/Domantis), Two-in-one Antibody (Genentech), Cross-linked Mabs (Karmanos Cancer Center), mAb$^2$ (F-Star) and CovX-body (CovX/Pfizer).

Examples of IgG fusion molecules include but are not limited to Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec) and TvAb (Roche).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual (ScFv)$_2$-Fab (National Research Center for Antibody Medicine—China).

Examples of class V bispecific antibodies include but are not limited to F(ab)$_2$ (Medarex/Amgen), Dual-Action or Bis-Fab (Genentech), Dock-and-Lock (DNL) (ImmunoMedics), Bivalent Bispecific (Biotecnol) and Fab-Fv (UCB-Celltech). Examples of ScFv- and diabody-based molecules include but are not limited to Bispecific T Cell Engager (BiTE) (Micromet9, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech).

In a further aspect, the invention relates to a bispecific molecule comprising an anti-CD38 antibody of the invention as described herein above and a second binding specificity such as a binding specificity for human cytokines. In one embodiment, said cytokine is an anti-inflammatory cytokine such as IL-1ra, IL-4, IL-6, IL-10, IL-11, IL-13, IL-16, IFN-alpha and TGF-beta. In another embodiment said cytokine is a pro-inflammatory cytokine such as IL-1alpha, IL-1beta and IL-6. In an embodiment the binding specificity is for a human effector cell, a human Fc receptor or a T cell receptor. In one embodiment, said T cell receptor is CD3. In another embodiment, said human Fc receptor is human FcγRI (CD64), human FcγRII (CD32), FcγRIII (CD16) or a human Fcα receptor (CD89). Bispecific molecules of the present invention may further include a third binding specificity, in addition to an anti-CD38 binding specificity and a binding specificity for a human effector cell, a human Fc receptor or a T cell receptor.

Exemplary bispecific antibody molecules of the invention comprise (i) two antibodies one with a specificity to CD38 and another to a second target that are conjugated together, (ii) a single antibody that has one chain specific to CD38 and a second chain specific to a second molecule, and (iii) a single chain antibody that has specificity to CD38 and a second molecule. In one embodiment, the second molecule is a cancer antigen/tumor-associated antigen such as CD20, carcinoembryonic antigen (CEA), prostate specific antigen (PSA), RAGE (renal antigen), α-fetoprotein, CAMEL (CTL-recognized antigen on melanoma), CT antigens (such as MAGE- B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Marti, MelanA, MUM-1, MUM-2, MUM-3, HLA-B7, and Ep-CAM. In one embodiment, the second molecule is a cancer-associated integrin, such as α5β3 integrin. In one embodiment, the second molecule is an angiogenic factor or other cancer-associated growth factor, such as a vascular endothelial growth factor (VEGF), a fibroblast growth factor (FGF), epidermal growth factor (EGF), epidermal growth factor receptor (EGFR), angiogenin, and receptors thereof, particularly receptors associated with cancer progression (for instance one of the HER1-HER4 receptors). Other cancer progression-associated proteins discussed herein may also be suitable second molecules.

In an embodiment of the invention, the antibody is a single antibody that has one chain specific to the CD38 epitope described in this invention comprising aspartic acid at position 202 and a second chain specific for a CD38 specific epitope that does not comprise the aspartic acid at position 202 (a non-competing antibody). Such antibody is described for example in WO2006099875 as antibody 003.

In one embodiment, a bispecific antibody of the present invention is a diabody.

Generation of Bispecific Antibodies by 2-MEA-Induced Fab-Arm Exchange

An in vitro method for producing bispecific antibodies is described in WO 2008119353 (Genmab) and reported by van der Neut-Kolfschoten et al. (Science. 2007 Sep. 14; 317 (5844):1554-7). Herein, a bispecific antibody is formed by "Fab-arm" or "half-molecule" exchange (swapping of a heavy chain and attached light chain) between two monospecific IgG4- or IgG4-like antibodies upon incubation under mildly reducing conditions. This Fab-arm exchange reaction is the result of a disulfide-bond isomerization reaction wherein the inter heavy-chain disulfide bonds in the hinge regions of monospecific antibodies are reduced and the resulting free cysteines form a new inter heavy-chain disulfide bond with cysteine residues of another antibody molecule with a different specificity. The resulting product is a bispecific antibody having two Fab arms with different sequences.

In a novel invention the knowledge of this natural IgG4 Fab-arm exchange is adapted to generate a method to produce stable IgG1-based bispecific antibodies. The bispecific antibody product generated by this method described below will no longer participate in IgG4 Fab-arm exchange. The basis for this method is the use of complimentary CH3 domains, which promote the formation of heterodimers under specific assay conditions. To enable the production of bispecific antibodies by this method, IgG1 molecules carrying certain mutations in the CH3 domain were generated: in one of the parental IgG1 antibody T350I, K370T and F405L mutations in the other parental IgG1 antibody the K409R mutation.

To generate bispecific antibodies, these two parental antibodies, each antibody at a final concentration of 0.5 mg/mL (equimolar concentration), were incubated with 25 mM 2-mercaptoethylamine-HCl (2-MEA) in a total volume of 100 μL TE at 37° C. for 90 min. The reduction reaction is stopped when the reducing agent 2-MEA is removed by using spin columns (Microcon centrifugal filters, 30 k, Millipore) according to the manufacturer's protocol. By this method the following bispecific antibodies may be generated:

A bispecfic antibody wherein the anti-CD38 antibody is 025, 026, 028, 049 or 056, and the second binding moiety is an anti-CD3 antibody.

A bispecfic antibody wherein the anti-CD38 antibody is 025, 026, 028, 049 or 056, and the second binding moiety is an anti-CD20 antibody, such as ofatumumab.

A bispecfic antibody wherein the anti-CD38 antibody is 025, 026, 028, 049 or 056, and the second binding moiety is an anti-CD16 antibody.

A bispecfic antibody wherein the anti-CD38 antibody is 025, 026, 028, 049 or 056, and the second binding moiety is an anti-CD32 antibody.

A bispecfic antibody wherein the anti-CD38 antibody is 025, 026, 028, 049 or 056, and the second binding moiety is an anti-CD64 antibody.

Nucleic Acids, Vectors, Host Cells and Method for Producing Antibodies of the Invention In a further aspect, the invention relates to nucleic acids encoding (parts of) an antibody of the invention and to expression vectors comprising such nucleic acids.

In one embodiment, the expression vector of the invention comprises a nucleotide sequence encoding one or more of the amino acid sequences selected from the group consisting of: SEQ ID NO: 1 and SEQ ID NO: 5.

In a further embodiment, the expression vector further comprises a nucleotide sequence encoding the constant region of a light chain, a heavy chain or both light and heavy chains of an antibody, e.g. a human antibody.

Such expression vectors may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-CD38 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the anti-CD38 antibody in a bacterial cell. In another embodiment, the expression vector may be a vector suitable for expression in a yeast system. Most typically, the vector will be a vector suitable for expression of the antibody of the invention in a mammalian cell, such as a CHO, HEK or PER.C6® cell (human cell line developed by DSM and Crucell N.V., the Netherlands). Another suitable vector system is the glutamine synthetase (GS) vector system developed by Lonza Biologics (see e.g. EP216846, U.S. Pat. No. 5,981,216, WO8704462, EP323997, U.S. Pat. No. 5,591,639, U.S. Pat. No. 5,658,759, EP338841, U.S. Pat. No. 5,879,936, and U.S. Pat. No. 5,891,693).

In an expression vector of the invention, anti-CD38 antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the anti-CD38-antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein. Examples of host cells include yeast, bacterial, and mammalian cells, such as a CHO, HEK or PER.C6® cells. For example, in one embodiment, the present invention provides a cell comprising a nucleic acid stably integrated into the cellular genome that comprises a sequence coding for expression of an anti-CD38 antibody of the present invention. In another embodiment, the present invention provides a cell comprising a non-integrated nucleic acid, such as a plasmid, cosmid, phagemid, or linear expression element, which comprises a sequence coding for expression of an anti-CD38 antibody of the invention.

In a further aspect, the invention relates to a hybridoma which produces an antibody of the invention as defined herein. In an even further aspect, the invention relates to a transgenic non-human animal comprising nucleic acids encoding a human heavy chain and a human light chain, wherein the animal or plant produces an antibody of the invention. Generation of such hybridomas and transgenic animals has been described above.

In a further aspect, the invention relates to a method for producing an anti-CD38 antibody of the invention, said method comprising the steps of:

a) culturing a hybridoma or a host cell of the invention as described herein above, and b) purifying the antibody of the invention from the culture media.

Pharmaceutical Compositions

In an even further aspect, the invention relates to a pharmaceutical composition comprising:

an anti-CD38 antibody as defined herein, and a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

In one embodiment the compounds of the present invention are administered in crystalline form by subcutaneous injection, cf. Yang et al., PNAS USA 100 (12), 6934-6939 (2003).

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Other carriers are well known in the pharmaceutical arts.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Methods for the preparation of such formulations are generally known to those skilled in the art. See e.g., Sustained and Controlled Release Drug Delivery Systems, J. R. Robinson, ed., Marcel Dekker, Inc., New York, 1978.

The pharmaceutical composition of the present invention may contain one antibody of the present invention or a combination of two or more antibodies of the present invention.

Therapeutic Uses

In another aspect, the invention relates to the antibody of the invention as defined herein for use as a medicament.

The anti-CD38 antibodies of the present invention have numerous therapeutic utilities involving the treatment of disorders involving cells expressing CD38. For example, the antibodies may be administered to cells in culture, e.g., in vitro or ex vivo, or to human subjects, e.g., in vivo, to treat or prevent a variety of disorders. As used herein, the term "subject" is intended to include human and non-human animals which respond to the antibody. Subjects may for instance include human patients having disorders that may be corrected or ameliorated by modulating CD38 function, such as enzymatic activity, signal transduction, induction of cytokine expression, induction of proliferation or differentiation, and/or induction of lysis and/or eliminating/reducing the number of CD38 expressing cells.

For example, the anti-CD38 antibodies may be used to elicit in vivo or in vitro one or more of the following biological activities: modulating CD38 function (such as enzymatic activity, signal transduction, induction of cytokine expression, induction of proliferation or differentiation, and/or induction of lysis), killing a cell expressing CD38, mediating phagocytosis or ADCC of a cell expressing CD38 in the presence of human effector cells, and by mediating CDC of a cell expressing CD38 in the presence of complement or by killing CD38 expressing cells by apoptosis.

The present invention provides methods for treating or preventing a disorder involving cells expressing CD38 in a subject, which method comprises administration of a therapeutically effective amount of an anti-CD38 antibody of the present invention to a subject in need thereof. Such a method involves administering to a subject an anti-CD38 antibody of the present invention in an amount effective to treat or prevent the disorder.

In one embodiment of the present invention, the disorder involving cells expressing CD38 may be cancer, i.e. a tumorigenic disorder, such as a disorder characterized by the presence of tumor cells expressing CD38 including, for example, B cell lymphoma, plasma cell malignancies, T/NK cell lymphoma and myeloid malignancies.

Examples of such tumorigenic diseases include B cell lymphomas/leukemias including precursor B cell lymphoblastic leukemia/lymphoma and B cell non-Hodgkin's lymphomas; acute promyelocytic leukemia, acute lymphoblastic leukemia and mature B cell neoplasms, such as B cell chronic lymhocytic leukemia (CLL)/small lymphocytic lymphoma (SLL), B cell acute lymphocytic leukemia, B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, plasma cell leukemia, post-transplant lymphoproliferative disorder, Waldenström's macroglobulinemia, plasma cell leukemias and anaplastic large-cell lymphoma (ALCL).

In one embodiment, the disorder involving cells expressing CD38 is multiple myeloma.

In one embodiment, the disorder involving cells expressing CD38 is selected from chronic lymphocytic leukemia (CLL), acute lymphoblastic leukemia (ALL), acute myelogenous leukemia (adults) (AML), mantle cell lymphoma, follicular lymphoma, and diffuse large B-cell lymphoma.

In one embodiment the disorder involving cells expressing CD38 is non-small cell lung cancer (NSCLC).

Examples of B cell non-Hodgkin's lymphomas are lymphomatoid granulomatosis, primary effusion lymphoma, intravascular large B cell lymphoma, mediastinal large B cell lymphoma, heavy chain diseases (including γ, μ, and α disease), lymphomas induced by therapy with immunosuppressive agents, such as cyclosporine-induced lymphoma, and methotrexate-induced lymphoma.

In one embodiment of the present invention, the disorder involving cells expressing CD38 is Hodgkin's lymphoma.

Other examples of disorders involving cells expressing CD38 include malignancies derived from T and NK cells including: mature T cell and NK cell neoplasms including T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, subcutaneous panniculitis-like T cell lymphoma, blastic NK cell lymphoma, Mycosis Fungoides/Sezary Syndrome, primary cutaneous CD30 positive T cell lymphoproliferative disorders (primary cutaneous anaplastic large cell lymphoma C-ALCL, lymphomatoid papulosis, borderline lesions), angioimmunoblastic T cell lymphoma, peripheral T cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

In another embodiment of the present invention, the disorder involving cells expressing CD38 is an immune disorder in which CD38 expressing B cells, macrophages, plasma cells, monocytes and T cells are involved, such as an inflammatory and/or autoimmune disease. Examples of immune disorders in which CD38 expressing B cells, plasma cells, monocytes and T cells are involved include autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, multiple sclerosis, HIV, and herpes virus associated diseases. Further examples are severe acute respiratory distress syndrome and choreoretinitis. Furthermore, other diseases and disorders are included such as those caused by or mediated by infection of B-cells with virus, such as Epstein-Barr virus (EBV).

In one embodiment, the disorder involving cells expressing CD38 is rheumatoid arthritis.

Further examples of inflammatory, immune and/or autoimmune disorders in which autoantibodies and/or excessive B and T lymphocyte activity are prominent and which may be treated according to the present invention include the following: vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulinaemica, and Buerger's disease; skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia greata (including alopecia universalis and alopecia totalis), dermatitis herpetiformis, erythema multiforme, and chronic autoimmune urticaria (including angioneurotic edema and urticarial vasculitis); immune-mediated cytopenias, such as autoimmune neutropenia, and pure red cell aplasia; connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; a further example is eosinophil fasciitis; arthritides, such as ankylosing spondylitis, juvenile chronic arthritis, adult Still's disease, and SAPHO syndrome; further examples are sacroileitis, reactive arthritis, Still's disease, and gout; hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldemström's purpura hyperglobulinaemica; further examples are agranulocytosis, autoimmune neutropenia, Franklin's disease, Seligmann's disease, gamma heavy chain disease, paraneoplastic syndrome secondary to thymoma and lymphomas, an, paraneoplastic syndrome secondary to thymoma and lymphomas, and factor VIII inhibitor formation; endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance; hepato-gastrointestinal disorders, such as celiac disease, Whipple's disease, primary biliary cirrhosis, chronic active hepatitis, and primary sclerosing cholangiitis; a further example is autoimmune gastritis; nephropathies, such as rapid progressive glomerulonephritis, post-streptococcal nephritis, Goodpasture's syndrome, membranous glomerulonephritis, and cryoglobulinemic nephritis; a further example is minimal change disease; neurological disorders, such as autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy; multiple sclerosis; cardiac and pulmonary disorders, such as COPD, fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer; allergic disorders, such as bronchial asthma and hyper-IgE syndrome; a further example is amaurosis fugax; ophthalmologic disorders, such as idiopathic chorioretinitis; infectious diseases, such as parvovirus B infection (including hands-and-socks syndrome); gynecological-obstretical disorders, such as recurrent abortion, recurrent fetal loss, and intrauterine growth retardation; a further example is paraneoplastic syndrome secondary to gynaecological neoplasms; male reproductive disorders, such as paraneoplastic syndrome secondary to testicular neoplasms; and transplantation-derived disorders, such as allograft and xenograft rejection, and graft-versus-host disease.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

The efficient dosages and the dosage regimens for the anti-CD38 antibodies depend on the disease or condition to be treated and may be determined by the persons skilled in the art. An exemplary, non-limiting range for a therapeutically effective amount of a compound of the present invention is about 0.005-100 mg/kg, such as 0.05-100 mg/kg or 1-100 mg/kg, such as about 0.1-50 mg/kg, for example about 0.1-20 mg/kg, such as about 0.1-10 mg/kg, for instance about 0.1, 0.3, about 0.5, about 1, 2, 3, 4, 8, 16 or 24 mg/kg.

Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms.

In one embodiment, the anti-CD38 antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the anti-CD38 antibodies may be administered by slow continuous infusion over a long period, such as more than 24 hours, in order to reduce toxic side effects.

In one embodiment the anti-CD38 antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may e.g. be repeated one or more times as necessary, for example, after 6 months or 12 months.

In one embodiment, the anti-CD38 antibodies may be administered by maintenance therapy, such as, e.g., once a week for a period of 6 months or more.

In another embodiment, the anti-CD38 antibodies may be administered by a regimen including one infusion of an anti-CD38 antibody of the present invention followed by an infusion of an anti-CD38 antibody of the present invention conjugated to a radioisotope. The regimen may be repeated, e.g., 7 to 9 days later.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

An "effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject.

A "therapeutically effective amount" for rheumatoid arthritis may result in an at least $ACR_{20}$ Preliminary Definition of Improvement in the patients, such as in at least an $ACR_{50}$ Preliminary Definition of Improvement, for instance at least an $ARC_{70}$ Preliminary Definition of Improvement. $ACR_{20}$ Preliminary Definition of Improvement is Defined as: ≥20% improvement in: Tender Joint Count (TJC) and Swollen Joint Count (SJC) and ≥20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR). $ACR_{50}$ and $ACR_{70}$ are defined in the same way with ≥50% and ≥70% improvements, respectively. For further details see Felson et al., in American College of Rheumatology Preliminary Definition of Improvement in Rheumatoid Arthritis; Arthritis Rheumatism 38, 727-735 (1995).

Alternatively, a therapeutically effective amount for rheumatoid arthritis can be measured by DAS (disease activity score), including DAS28 and/or DAS56, as defined by EULAR.

An anti-CD38 antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Combination Therapy

The anti-CD38 antibodies of the present invention may also be administered in combination therapy, i.e., combined with other therapeutic agents relevant for the disease or condition to be treated. Such administration may be simultaneous, separate or sequential. For simultaneous administration the agents may be administered as one compositions or as separate compositions, as appropriate.

Accordingly, the present invention provides methods for treating a disorder involving cells expressing CD38 as described above, which methods comprise administration of an anti-CD38 antibody of the present invention combined with one or more additional therapeutic agents as described below.

In an embodiment of the invention the antibodies of the present invention are administered as a combination with other anti-CD38 antibodies. Such antibodies are described in the present invention and in prior art. Specifically, antibodies are described in WO2006099875. More specifically, a combination of the present anti-CD38 antibodies with anti-CD38 antibodies which are non-cross-blocking, such as antibody 003 described in WO2006099875 are embodiments of the present invention.

In one embodiment, the combination therapy may include administration of a composition of the present invention together with at least one cytotoxic agent, at least one chemotherapeutic agent, at least one anti-angiogenic agent, at least one anti-inflammatory agent, and/or at least one immunosuppressive and/or immunomodulatory agent.

In one embodiment, the present invention provides a method for treating a disorder involving cells expressing CD38, such as cancer, in a subject, which method comprises administration of a therapeutically effective amount of an anti-CD38 antibody of the present invention and at least one chemotherapeutic agent to a subject in need thereof.

In one embodiment, the present invention provides a method for treating multiple myeloma, which method comprises administration of a therapeutically effective amount of an anti-CD38 antibody of the present invention and at least one chemotherapeutic agent to a subject in need thereof.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents.

In one embodiment, such a chemotherapeutic agent may be selected from an antibiotic, such as dactinomycin (formerly actinomycin), bleomycin, daunorubicin (formerly daunomycin), doxorubicin, idarubicin, mithramycin, mitomycin, mitoxantrone, plicamycin, anthramycin (AMC) and similar agents.

In one embodiment, such a chemotherapeutic agent may be selected from an anti-mitotic agent, such as taxanes, for instance docetaxel, and paclitaxel, and vinca alkaloids, for instance vindesine, vincristine, vinblastine, and vinorelbine.

In one embodiment, such a chemotherapeutic agent may be selected from a topoisomerase inhibitor, such as topotecan.

In one embodiment, such a chemotherapeutic agent may be selected from a growth factor inhibitor, such as an inhibitor of ErbB1 (EGFR) (such as gefitinib (Iressa®), cetuximab (Erbitux®), erlotinib (Tarceva®), HuMax-EGFr (zalutumumab, 2F8 disclosed in WO 2002/100348) and similar agents), an inhibitor of ErbB2 (Her2/neu) (such as trastuzumab (Herceptin®) and similar agents) and similar agents. In one embodiment, such a growth factor inhibitor may be a farnesyl transferase inhibitor, such as SCH-66336 and R115777. In one embodiment, such a growth factor inhibitor may be a vascular endothelial growth factor (VEGF) inhibitor, such as bevacizumab (Avastin®).

In one embodiment, such a chemotherapeutic agent may be a tyrosine kinase inhibitor, such as imatinib (Glivec, Gleevec STI571), lapatinib, PTK787/ZK222584 and similar agents.

In one embodiment, such a chemotherapeutic agent may be a histone deacetylase inhibitor. Examples of such histone deacetylase inhibitors include hydroxamic acid-based hybrid polar compounds, such as SAHA (suberoylanilide hydroxamic acid).

In one embodiment, such a chemotherapeutic agent may be a P38a MAP kinase inhibitor, such as SCIO-469.

In one embodiment, the present invention provides a method for treating a disorder involving cells expressing CD38 in a subject, which method comprises administration of a therapeutically effective amount of an anti-CD38 antibody of the present invention and at least one inhibitor of angiogenesis, neovascularization, and/or other vascularization to a subject in need thereof.

In one embodiment, the present invention provides a method for treating multiple myeloma, which method comprises administration of a therapeutically effective amount of an anti-CD38 antibody of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as ZD6474, SU66680, antibodies against angiogenic agents and/or their receptors (such as VEGF, bFGF, and angiopoietin-1), thalidomide (Thalomid®), thalidomide analogs (such as CC-5013 (lenalidomide, Revlimid™) and CC4047 (Actimid™), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one embodiment, the present invention provides the use of an anti-CD38 antibody of the present invention for the preparation of a pharmaceutical composition to be administered with thalidomide (Thalomid®), thalidomide analogs (such as CC-5013 (lenalidomide, Revlimid™) and/or CC4047 (Actimid™). In a further embodiment, the present invention provides the use of an anti-CD38 antibody of the present invention for the preparation of a pharmaceutical composition to be administered with thalidomide.

In one embodiment, the present invention provides the use of an anti-CD38 antibody of the present invention for the preparation of a pharmaceutical composition to be administered with an anti-CD20 antibody, such as rituximab (Rituxan®, Mabthera®), a human monoclonal anti-CD20 antibody as disclosed in WO 2004/035607, such as 11B8, 2F2 (ofatumumab, Arzerra®) or 7D8.

In one embodiment, a therapeutic agent for use in combination with the anti-CD38 antibody of the present invention for treating the disorders as described above may be a proteasome inhibitor, such as bortezomib (Velcade®).

In one embodiment, a therapeutic agent for use in combination with the anti-CD38 antibody of the present invention for treating the disorders as described above may be a corticosteroid, such as prednisone, prednisolone, dexamethasone, etc.

In one embodiment, the anti-CD38 antibody of the present invention is used in combination with lenalidomide and dexamethasone for treating the disorders as described above, such as multiple myeloma, e.g. relapsed multiple myeloma.

In one embodiment, the anti-CD38 antibody of the present invention is used in combination with bortezomib and dexamethasone for treating the disorders as described above, such as multiple myeloma, e.g. relapsed multiple myeloma.

In one embodiment, the anti-CD38 antibody of the present invention is used in combination with bortezomib and prednisolone for treating the disorders as described above, such as multiple myeloma, e.g. relapsed multiple myeloma.

In one embodiment, a therapeutic agent for use in combination with the anti-CD38 antibody of the present invention for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21 (15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J. Immunol. 137(5), 1743-9 (1986), Pohl et al., Int J Cancer. 50(6), 958-67 (1992), Bohlen et al., Cytokines Mol. Ther. 2(4), 231-8 (1996) and Maruyama, J Immunol Methods. 264 (1-2), 121-33 (2002)). Such anti-idiotypic Antibodies may optionally be conjugated to a carrier, which may be a synthetic (typically inert) molecule carrier, a protein (for instance keyhole limpet hemocyanin (KLH) (see for instance Ochi et al., Eur J. Immunol. 17 (11), 1645-8 (1987)), or a cell (for instance a red blood cell—see for instance Wi et al., J Immunol Methods. 122 (2), 227-34 (1989)).

In one embodiment, a therapeutic agent for use in combination with the anti-CD38 antibody of the present invention for treating the disorders as described above may be a bisphosphonate. Examples of potentially suitable biphosphonates are pamidronate (Aredia®), zoledronic acid (Zometa®), clodronate (Bonefos®), risendronate (Actonel®), ibandronate (Boniva®), etidronate (Didronel®), alendronate (Fosamax®), tiludronate (Skelid®), incadronate (Yamanouchi Pharmaceutical) and minodronate (YM529, Yamanouchi).

In one embodiment, a therapeutic agent for use in combination with the anti-CD38 antibody of the present invention for treating the disorders as described above may be a colony stimulating factor. Examples of suitable colony stimulating factors are granulocyte-colony stimulating factors (G-CSF), such as filgrastim (Neupogen®) and pegfilgrastim (Neulasta®), and granulocyte macrophage-colony stimulating factors (GM-CSF) such as sargramostim (Leukine®).

In one embodiment, a therapeutic agent for use in combination with the anti-CD38 antibody of the present invention for treating the disorders as described above may be a erythropoietic agent. Examples of suitable erythropoietic agents are erythropoietin (EPO), such as epoetin alfa (for instance Procrit®, Epogen®, and Eprex®) and epoetin beta (for instance NeoRecormon®) and erythropoiesis-stimulating proteins (for instance Aranesp®).

In one embodiment, a therapeutic agent for use in combination with the anti-CD38 antibody of the present invention for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins. These and other methods or uses involving naturally occurring peptide-encoding nucleic acids herein may alternatively or additionally be performed by "gene activation" and homologous recombination gene upregulation techniques, such as are described in U.S. Pat. No. 5,968,502, U.S. Pat. No. 6,063,630 and U.S. Pat. No. 6,187,305 and EP 0505500.

In one embodiment, a therapeutic agent for use in combination with the anti-CD38 antibody of the present invention for treating the disorders as described above may be an agent that modulates, e.g., enhances or inhibits, the expression or activity of Fcα or Fcγ receptors. Examples of agents suitable for this use include interleukin-1 (IL-1), interleukin-2 (IL-2), interleukin-6 (IL-6), granulocyte colony-stimulating factor (G-CSF), such as filgrastim (Neupogen®) and pegfilgrastim (Neulasta®), and granulocyte macrophage-colony stimulating factors (GM-CSF) such as sargramostim (Leukine®), interferon-γ (IFN-γ), and tumor necrosis factor (TNF).

In one embodiment, a therapeutic agent for use in combination with the anti-CD38 antibody of the present invention for treating the disorders as described above may be a cell cycle control/apoptosis regulator (or "regulating agent"). A cell cycle control/apoptosis regulator may include molecules (i) that target and modulate cell cycle control/apoptosis regulators such as cdc-25 (such as NSC 663284), (ii) cyclin-dependent kinases that overstimulate the cell cycle (such as flavopiridol (L868275, HMR1275), 7-hydroxy-staurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), agents inducing NF-κB blockade leading to inhibition of IL-6 production, antibodies that activate TRAIL receptors, IFNs, anti-sense Bcl-2, and $As_2O_3$ (arsenic trioxide, Trisenox®).

In one embodiment, a therapeutic agent for use in combination with the anti-CD38 antibody of the present invention for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogen (such as flutaminde/eulexin), a progestin (such as such as hydroxy-progesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents.

In one embodiment, a therapeutic agent for use in combination with the anti-CD38 antibody of the present invention for treating the disorders as described above may be an anti-anergic agents (for instance small molecule compounds, proteins, glycoproteins, or antibodies that break tolerance to tumor and cancer antigens). Examples of such compounds are molecules that block the activity of CTLA-4, such as MDX-010 (Phan et al., PNAS USA 100, 8372 (2003)).

In one embodiment, a therapeutic agent for use in combination with the anti-CD38 antibody of the present invention for treating the disorders as described above may be a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with the anti-CD38 antibody of the present invention for treating the disorders as described above may be an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h.

In one embodiment, a therapeutic agent for use in combination with the anti-CD38 antibody of the present invention for treating the disorders as described above may be an anti-cancer inhibitory RNA molecule (see for instance Lin et al., Curr Cancer Drug Targets. 1 (3), 241-7 (2001), Erratum in: Curr Cancer Drug Targets. 3(3), 237 (2003), Lima et al., Cancer Gene Ther. 11 (5), 309-16 (2004), Grzmil et al., Int J Oncol. 4 (1), 97-105 (2004), Collis et al., Int J Radiat Oncol Biol Phys. 57 (2 Suppl), S144 (2003), Yang et al., Oncogene. 22 (36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. No. 5,589,466, U.S. Pat. No. 5,593,972, U.S. Pat. No. 5,703,057, U.S. Pat. No. 5,879,687, U.S. Pat. No. 6,235,523, and U.S. Pat. No. 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50 (3), 613-24 (2003), Reilly et al., Methods Mol. Med. 69, 233-57 (2002) and Tirapu et al., Curr Gene Ther. 2 (1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, the present invention provides combination compositions and combination administration methods wherein an anti-CD38 antibody is combined or co-administered with an oncolytic virus.

Combination compositions and combination administration methods of the present invention may also involve "whole cell and "adoptive" immunotherapy methods. For instance, such methods may comprise infusion or re-infusion of immune system cells (for instance tumor-infiltrating lymphocytes (TILs), such as $CD4^+$ and/or $CD8^+$ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, an anti-CD38 antibody of the present invention may be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell-death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with the anti-CD38 antibody of the present invention for treating the disorders as described above are differentiation inducing agents, retinoic acid and retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with the anti-CD38 antibody of the present invention for treating the disorders as described above are cathepsin B, modulators of cathepsin D dehydrogenase activity, glutathione-S-transferase (such as glutacylcysteine synthetase and lactate dehydrogenase), estramustine, epirubicin, HSP90 inhibitor like 17-allyl amino geld-anamycin, antibodies directed against a tumor antigen such as PSA, CA125, KSA, etc., integrins like integrin β1, inhibitors of VCAM and similar agents.

Examples of other anti-cancer agents, which may be relevant as therapeutic agents for use in combination with the anti-CD38 antibodies of the present invention for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA, etc.).

In one embodiment, the present invention provides a method for treating a disorder involving cells expressing CD38, such as cancer, in a subject, which method comprises administration of a therapeutically effective amount of an anti-CD38 antibody of the present invention and radiotherapy to a subject in need thereof.

In one embodiment, the present invention provides a method for treating multiple myeloma, which method comprises administration of a therapeutically effective amount of an anti-CD38 antibody of the present invention and radiotherapy to a subject in need thereof.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT), brachytherapy (BT) or skeletal targeted radiotherapy). Radioactive elements that may be used in practicing such methods include, e.g., radium, cesium-137, iridium-192, americium-241, gold-198, cobalt-57, copper-67, technetium-99, iodide-123, iodide-131, and indium-111.

In one embodiment, the present invention provides a method for treating a disorder involving cells expressing CD38 in a subject, which method comprises administration of a therapeutically effective amount of an anti-CD38 antibody of the present invention to a subject in need thereof combined with autologous peripheral stem cell or bone marrow transplantation.

In one embodiment, the present invention provides a method for treating multiple myeloma, which method comprises administration of a therapeutically effective amount of an anti-CD38 antibody of the present invention to a subject in need thereof combined with autologous peripheral stem cell or bone marrow transplantation.

In one embodiment, the present invention provides a method for treating a disorder involving cells expressing CD38 in a subject, which method comprises administration of a therapeutically effective amount of an anti-CD38 antibody of the present invention to a subject in need thereof combined with orthopedic intervention.

In one embodiment, the present invention provides a method for treating a disorder involving cells expressing CD38 in a subject, which method comprises administration of a therapeutically effective amount of an anti-CD38 antibody of the present invention and at least one anti-inflammatory agent to a subject in need thereof.

In one embodiment such an anti-inflammatory agent may be selected from a steroidal drug and a NSAID (nonsteroidal anti-inflammatory drug).

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. antibodies described in WO2004058797, e.g. 10F8), anti-IL15 antibodies (e.g. antibodies described in WO03017935 and WO2004076620), anti-IL15R antibodies, anti-CD4 antibodies (e.g. zanolimumab), anti-CD11a antibodies (e.g., efalizumab), anti-alpha-4/beta-1 integrin (VLA4) antibodies (e.g. natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, the present invention provides a method for treating a disorder involving cells expressing CD38 in a subject, which method comprises administration of a therapeutically effective amount of an anti-CD38 antibody of the present invention and at least one immunosuppressive and/or immunomodulatory agent to a subject in need thereof.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, or antibodies binding to for instance MHC, CD2, CD3, CD4, CD7, CD28, B7, CD40, CD45, IFNγ, TNF-α, IL-4, IL-5, IL-6R, IL-6, IGF, IGFR1, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents.

In one embodiment, the anti-CD38 antibody of the present invention may be administered in combination with two or more immunosuppressive and/or immunomodulatory agents, such as in combination with prednisone and cyclosporine; prednisone, cyclosporine and azathioprine; or prednisone, cyclosporine and mycophenolate mofetil.

In one embodiment, the present invention provides a method for treating a disorder involving cells expressing CD38 in a subject, which method comprises administration of a therapeutically effective amount of an anti-CD38 antibody of the present invention and an anti-C3b(i) antibody to a subject in need thereof.

In one embodiment, the present invention provides a method for treating a disorder involving cells expressing CD38 in a subject, which method comprises administration of a therapeutically effective amount of an anti-CD38 antibody of the present invention and an anti-CD32b antibody to a subject in need thereof. In one embodiment of the present invention, the anti-CD32b antibody is selected from HuMab-016, -020, -022, -024, 026, 028, -034, -038 or -053 all disclosed in WO2009/083009.

In one embodiment, a therapeutic agent for use in combination with the anti-CD38 antibody of the present invention for treating the disorders as described above may be selected from histone deacetylase inhibitors (for instance phenylbutyrate) and/or DNA repair agents (for instance DNA repair enzymes and related compositions such as dimericine).

Methods of the present invention for treating a disorder as described above comprising administration of a therapeutically effective amount of an anti-CD38 antibody of the present invention may also comprise anti-cancer directed photodynamic therapy (for instance anti-cancer laser therapy—which optionally may be practiced with the use of photosensitizing agent, see, for instance Zhang et al., J Control Release. 93 (2), 141-50 (2003)), anti-cancer sound-wave and shock-wave therapies (see for instance Kambe et al., Hum Cell. 10 (1), 87-94 (1997)), and/or anti-cancer nutraceutical therapy (see for instance Roudebush et al., Vet Clin North Am Small Anim Pract. 34 (1), 249-69, viii (2004) and Rafi, Nutrition. 20 (1), 78-82 (2004). Likewise, an anti-CD38 antibody of the present invention may be used for the preparation of a pharmaceutical composition for treating a disorder as described above to be administered with anti-cancer directed photodynamic therapy (for instance anti-cancer laser therapy—which optionally may be practiced with the use of photosensitizing agent, anti-cancer sound-wave and shock-wave therapies, and/or anti-cancer nutraceutical therapy.

In a further embodiment, the anti-CD38 antibody of the present invention is administered together with complement.

As described above, a pharmaceutical composition of the present invention may be administered in combination therapy, i.e., combined with one or more agents relevant for the disease or condition to be treated either as separate pharmaceutical compositions or with a compound of the present invention coformulated with one or more additional therapeutic agents as described above. Such combination therapies may require lower dosages of the compound of the present invention and/or the co-administered agents, thus avoiding possible toxicities or complications associated with the various monotherapies.

In one embodiment, the present invention provides a method for treating a disorder involving cells expressing CD38 in a subject, which method comprises administration of a therapeutically effective amount of an anti-CD38 antibody of the present invention and at least one immunosuppressive and/or immunomodulatory agent to a subject in need thereof.

Diagnostic Uses

The anti-CD38 antibodies of the invention may also be used for diagnostic purposes. Thus, in a further aspect, the invention relates to a diagnostic composition comprising an anti-CD38 antibody as defined herein.

In one embodiment, the anti-CD38 antibodies of the present invention may be used in vivo or in vitro for diagnosing diseases wherein activated cells expressing CD38 play an active role in the pathogenesis, by detecting levels of CD38, or levels of cells which contain CD38 on their membrane surface. This may be achieved, for example, by contacting a sample to be tested, optionally along with a control sample, with the anti-CD38 antibody under conditions that allow for formation of a complex between the antibody and CD38. Complex formation is then detected (e.g., using an ELISA). When using a control sample along with the test sample, complex is detected in both samples and any statistically significant difference in the formation of complexes between the samples is indicative of the presence of CD38 in the test sample.

Thus, in a further aspect, the invention relates to a method for detecting the presence of CD38 antigen, or a cell expressing CD38, in a sample comprising:

contacting the sample with an anti-CD38 antibody of the invention or a bispecific molecule of the invention, under conditions that allow for formation of a complex between the antibody and CD38; and analyzing whether a complex has been formed.

In one embodiment, the method is performed in vitro.

More specifically, the present invention provides methods for the identification of, and diagnosis of invasive cells and tissues, and other cells targeted by anti-CD38 antibodies of the present invention, and for the monitoring of the progress of therapeutic treatments, status after treatment, risk of developing cancer, cancer progression, and the like.

In one example of such a diagnostic assay, the present invention provides a method of diagnosing the level of invasive cells in a tissue comprising forming an immunocomplex between an anti-CD38 antibody and potential CD38-containing tissues, and detecting formation of the immunocomplex, wherein the formation of the immunocomplex correlates with the presence of invasive cells in the tissue. The contacting may be performed in vivo, using labeled isolated antibodies and standard imaging techniques, or may be performed in vitro on tissue samples.

Examples of conventional immunoassays provided by the present invention include, without limitation, an ELISA, an RIA, FACS assays, plasmon resonance assays, chromatographic assays, tissue immunohistochemistry, Western blot, and/or immunoprecipitation using an anti-CD38 antibody. Suitable labels for the anti-CD38 antibody and/or secondary antibodies used in such techniques include, without limitation, various enzymes, prosthetic groups, fluorescent materials, luminescent materials, and radioactive materials.

The anti-CD38 antibodies are particularly useful in the in vivo imaging of tumors. In vivo imaging of tumors associated with CD38 may be performed by any suitable technique. For example, $^{99}$Tc-labeling or labeling with another gamma-ray emitting isotope may be used to label anti-CD38 antibodies in tumors or secondary labeled (e.g., FITC labeled) anti-CD38 antibody:CD38 complexes from tumors and imaged with a gamma scintillation camera (e.g., an Elscint Apex 409ECT device), typically using low-energy, high resolution collimator or a low-energy all-purpose collimator. Stained tissues may then be assessed for radioactivity counting as an indicator of the amount of CD38-associated peptides in the tumor. The images obtained by the use of such techniques may be used to assess biodistribution of CD38 in a patient, mammal, or tissue, for example in the context of using CD38 or CD38-fragments as a biomarker for the presence of invasive cancer cells. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993).

In a further aspect, the invention relates to a kit for detecting the presence of CD38 antigen, or a cell expressing CD38, in a sample comprising an anti-CD38 antibody of the invention or a bispecific molecule of the invention; and instructions for use of the kit.

In one embodiment, the present invention provides a kit for diagnosis of cancer comprising a container comprising an anti-CD38 antibody, and one or more reagents for detecting binding of the anti-CD38 antibody to a CD38 peptide. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more anti-CD38 antibodies of the present invention in labeled or unlabeled form in suitable container(s), reagents for the incubations for an indirect assay, and substrates or derivatizing agents for detection in such an assay, depending on the nature of the label. Control reagent(s) may also be included.

In a further aspect, the invention relates to an anti-idiotypic antibody which binds to an anti-CD38 antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of an anti-CD38 mAb with the mAb to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880.

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to anti-CD38 antibodies of the present invention.

The present invention is further illustrated by the following examples which should not be construed as further limiting.

EXAMPLES

Example 1

Generation of Antibodies

HCo12 mice were immunized every fortnight with 20 µg purified HA-CD38 alternating with NIH-3T3-CD38 transfected cells. The first immunization was performed with 5×10⁶ cells in 100 μl PBS, mixed with 100 μl CFA, i.p., the second and following immunizations with HA-CD38 s.c., in the presence of 100 μl PBS, mixed with 100 μl IFA. The following immunizations with transfected cells were performed in the presence of 200 μl PBS. After titer development, mice were boosted with 20 μg HA-CD38 in PBS, i.v.

Spleens were harvested from these mice, splenocytes were isolated and fused with PEG to a mouse myeloma cell line based upon standard protocols. The resulting hybridomas were then screened for human antibody production by ELISA and for CD38 specificity using human CD38-transfected NS/0 cells by FACS analysis and recombinant HA-CD38 protein binding by ELISA.

Sequence Analysis of the Anti-CD38 HuMab Variable Domains and Cloning in Expression Vectors Total RNA of the anti-CD38 HuMabs was prepared from 5×10⁶ hybridoma cells and 5'-RACE-Complementary DNA (cDNA) was prepared from 100 ng total RNA, using the SMART RACE cDNA Amplification kit (Clontech), according to the manufacturer's instructions.

VH and VL coding regions were amplified by PCR and cloned into the pCR-Blunt II-TOPO vector (Invitrogen) using the Zero Blunt PCR cloning kit (Invitrogen). For each HuMab, 16 VL clones and 8 VH clones were sequenced.

The VL and VH encoding regions were cloned into the pKappa and pG1f vectors.

CDR regions are indicated according to IMGT. (imgt.cines.fr/IMGT_vquest/vquest?livret=0&Option=humanIg)

The following IgG1, κ human monoclonal antibodies were identified:

| | VH | VL |
|---|---|---|
| 025 | SEQ ID NO: 7 | SEQ ID NO: 32 |
| 026 | SEQ ID NO: 12 | SEQ ID NO: 37 |
| 028 | SEQ ID NO: 2 | SEQ ID NO: 27 |
| 049 | SEQ ID NO: 17 | SEQ ID NO: 42 |
| 056 | SEQ ID NO: 22 | SEQ ID NO: 47 |

Example 2

Electrospray Ionisation-Quadrupole-Time of Flight Mass Spectrometry of Anti-CD38 Antibodies Intact molecular weight data for anti-CD38 antibodies 025, 057 (same amino acid sequence as antibody 026), 028, 049 and 056 were obtained using nanospray Electrospray-MS on a Q-TOF mass spectrometer. Aliquots of each antibody sample were desalted offline using $C_4$ micro-tap cartridge and eluted in propanol/trifluoroacetic acid solvent. The instrument was calibrated using glu-fibrinopeptide fragment ions in MS/MS mode. MassLynx 4.0 software was used to de-convolute the multiply-charged data obtained.

Information on the molecular weight of light and heavy chain components of these antibodies was obtained following reduction using dithiothreitol and analysis as described above.

TABLE 1

| Mass of CD38 antibodies (in Dalton) | | | | | | |
|---|---|---|---|---|---|---|
| Anti- | intact MW | | | Light | Heavy Chain | |
| body | K0 | K1 | K2 | Chain | K0 | K1 |
| -025 | 144742.8 | 144874.1 | 144999.8 | 23357.8 | 49017.4 | 49145.8 |
| -057 | 144828.2 | 144946.4 | 145071.2 | 23357.8 | 49047.4 | 49175.8 |
| -028 | 144818.3 | 144946.4 | 145074.7 | 23357.8 | 49054.5 | 49182.8 |
| -049 | 144864.0 | 144990.6 | 145117.8 | 23384.8 | 49049.3 | 49177.9 |
| -056 | | 145100.7 | 145222.7 | 23384.8 | 49099.5 | 49226.4 |

Example 3

Cross-Block Studies Using FACS

CHO-CD38 cells were incubated with an excess of unlabelled CD38-specific antibodies (4° C., min). Then, cells were incubated with FITC-labeled 005 antibody (concentration approximates $EC_{90}$, 4° C., 45 min) (005 is disclosed in WO2006099875). After washing the cells twice with PBS-BSA, fluorescence was measured by flow cytometry. 005-FITC labeled antibody binding was blocked by excess unlabelled antibodies 025, 026, 028, 049 and 056, indicating that these antibodies have overlapping epitopes. Binding of 005-FITC was not blocked by excess unlabelled 003 (disclosed in WO2006099875) providing evidence for binding to a different epitope.

Cross-Blocking Studies Using ELISA

Soluble human CD38 was coated on the surface of an ELISA plate. Coated CD38 was incubated with an excess of unlabelled CD38 specific antibodies for about 15 minutes and subsequently biotinylated CD38-specific antibodies were added (concentration approximates $EC_{90}$, RT, 1 hour). After washing three times with PBS/Tween, horseradish peroxidase (HRP)-conjugated streptavidine was added and the mixture was incubated for 1 hour at RT. The complex was detected by addition of an ABTS-solution and the HRP mediated substrate conversion was measured using an ELISA reader at OD 405 nm.

Cross-Blocking Studies Using Sandwich-ELISA

Anti-CD38 antibodies were coated on the surface of an ELISA plate. Plate-bound antibodies were incubated with biotinylated soluble CD38 in the presence of an excess of anti-CD38 antibodies in fluid phase. After washing with PBS/Tween, bound biotinylated CD38 was detected with HRP-conjugated streptavidine for 1 hr at RT. This complex was detected by addition of an ABTS-solution (after washing with PBS/Tween) and the HRP mediated substrate conversion was measured using an ELISA reader at OD 405 nm.

Example 4

Epitope Mapping

Epitope Mapping
Construction of HA-CD38 and his-CD38 Expression Vectors.

The encoding sequences for the extracellular domain of human CD38 (identical to amino acids 45-300 from Genbank entry AAA68482) were amplified from plasmid pCIpuroCD38 (obtained from Prof. M. Glennie, Tenovus Research Laboratory, Southampton General Hospital, Southampton, UK) using PCR, introducing, restriction sites, an ideal Kozak sequence (GCCGCCACC), and sequences endcoding a signal peptide and a N-terminal HA tag (ypydvpdya) (SEQ ID NO: 54). The construct was cloned in the mammalian expression vector pEE13.4 (Lonza Biologics). This construct was named pEE13.4HACD38.

A similar construct was made synthetically and fully codon optimized (GeneArt, Regensburg, Germany), replacing the HA tag encoding part by a His tag (HHHHHH) (SEQ ID NO: 55) encoding part. The construct was cloned in pEE13.4 and named pEE13.4HisCD38.

Site Directed Mutagenesis

Several mutations were introduced in the putative antibody binding site on the CD38 molecule.

DNA substitutions leading to T237A, Q272R or S274F amino acid substitutions were generated using the Quick-Change II XL Site-directed Mutagenesis Kit (Stratagene, Amsterdam, The Netherlands) in the pEE13.4HACD38 vector. Similarly a D202G encoding substitution was introduced in the pEE13.4HisCD38 vector.

Transient Expression in HEK-293F Cells

Freestyle™293-F (a HEK-293 subclone adapted to suspension growth and chemically defined Freestyle medium, (HEK-293F)) cells were obtained from Invitrogen and transfected with pEE13.4HACD38, pEE13.4HisCD38 or the four constructs carrying the mutations, according to the manufacturer's protocol using 293fectin (Invitrogen). Cell culture supernatants of transfected cells were used in ELISA for anti-CD38 binding studies.

Anti-CD38 Antibody Binding

Mutations T237A, Q272R, and S274F: ELISA plates (Greiner, #655092) were coated O/N at 4° C. with 1 µg anti-HA antibody (Sigma, #H-9658) and subsequently blocked with 2% chicken serum. Culture supernatants of transfected HEK293F cells were diluted, applied to the ELISA plates and incubated for 1 hr at RT. After washing, serial dilutions of anti-CD38 antibodies were added and incubated for 1 hr at RT. Bound antibodies were detected with HRP-conjugated goat-anti-human IgG antibodies. The assay was developed with ABTS (Roche, #1112597) and the absorbance was measured at 405 nm using a spectrophotometer.

Mutation D202G: ELISA plates (Greiner, #655092) were coated O/N at 4° C. with 1 µg penta-His (Qiagen #34660) and subsequently blocked with 2% PBS/BSA. Culture supernatants of transfected HEK293F cells were diluted, applied to the ELISA plates and incubated for 2 hr at RT. After washing, serial dilutions of anti-CD38 antibodies were added and incubated for 1 hr at RT. Bound antibodies were detected with HRP-conjugated goat-anti-human IgG antibodies. The assay was developed with ABTS (Roche, #1112597) and the absorbance was measured at 405 nm using a spectrophotometer.

Figure 2:
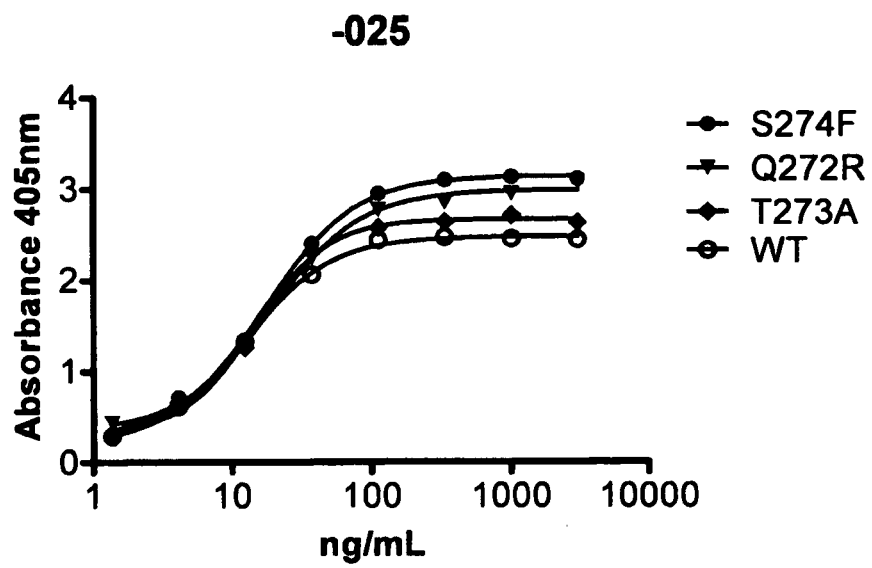
FIG. 2 shows binding of the anti-CD38 antibodies of the invention to wt and mutant CD38.
Figure 2:
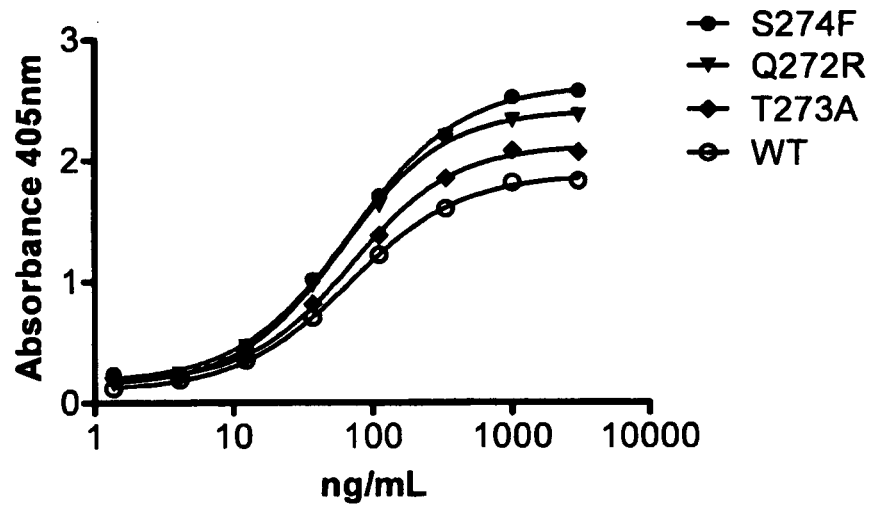
Figure 2:
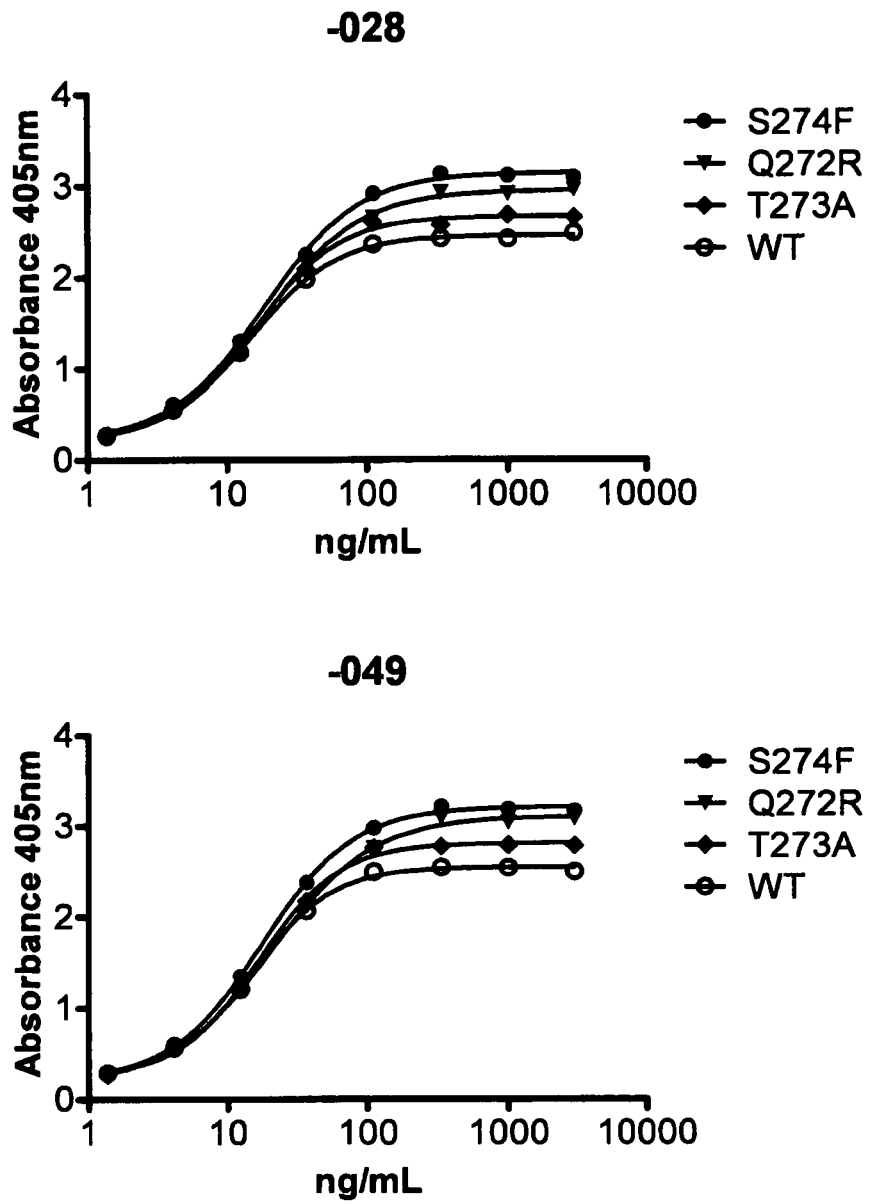
Figure 2:
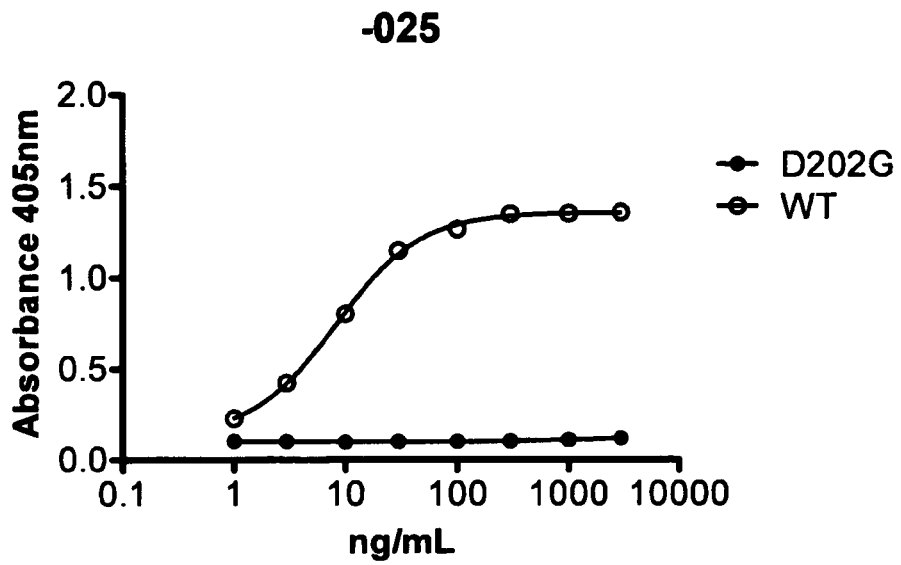
Figure 2:
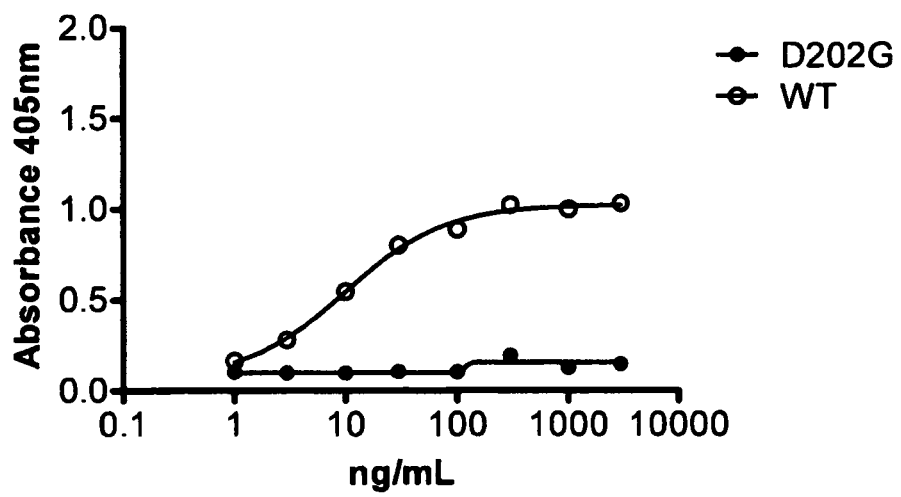
Figure 2:
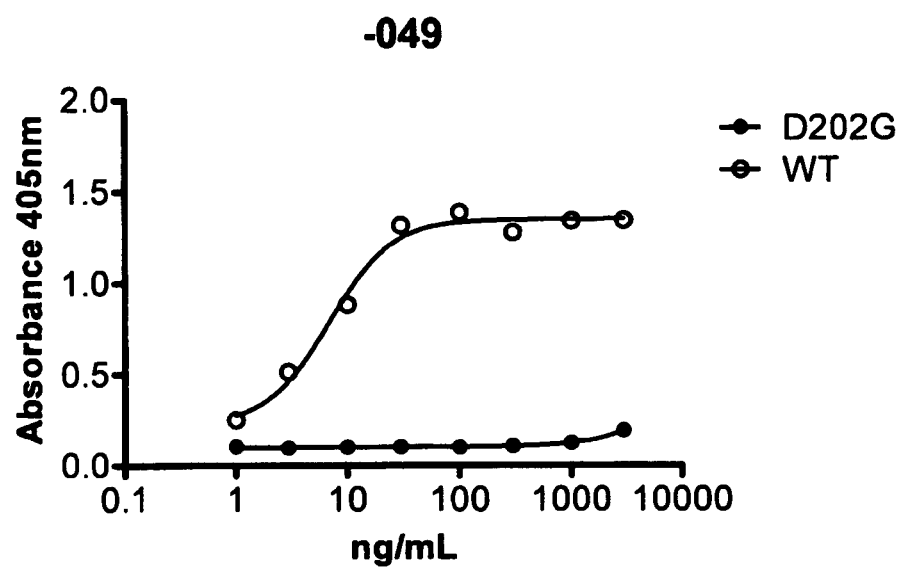

This study revealed that binding of 025, 026, 028 and 049 was not sensitive to mutations T237A, Q272R, S274F, and A199T, but was seriously affected by D202G (025, 028, 049) (FIG. 2).

Example 5

Binding of Anti-CD38 Antibodies to CD38-Transfected CHO(CHO-CD38) Cells and to Daudi-luc Cells After harvesting and counting, Daudi-luc cells, CHO cells transfected with CD38 and control CHO cells, were resuspended in PBS ($1\times10^6$ cells/mL). Cells were transferred to 96-well V-bottom plates (100 µL/well) and washed twice in PBS-BSA (PBS supplemented with 0.1% BSA and 0.02% Na-azide). 50 µL antibody in PBS-BSA was added in three-fold dilutions ranging from 0.3 to 30 µg/mL (4° C., 30 min). After washing three times in PBS-BSA, 50 µL (1:400 dilution) of rabbit anti-human IgG-FITC in PBS-BSA was added (4° C. in the dark, 30 minutes). Cells were washed three times and specific binding of CD38-antibodies to CHO-CD38 and Daudi-luc cells was detected by flow cytometry.

Figure 3:
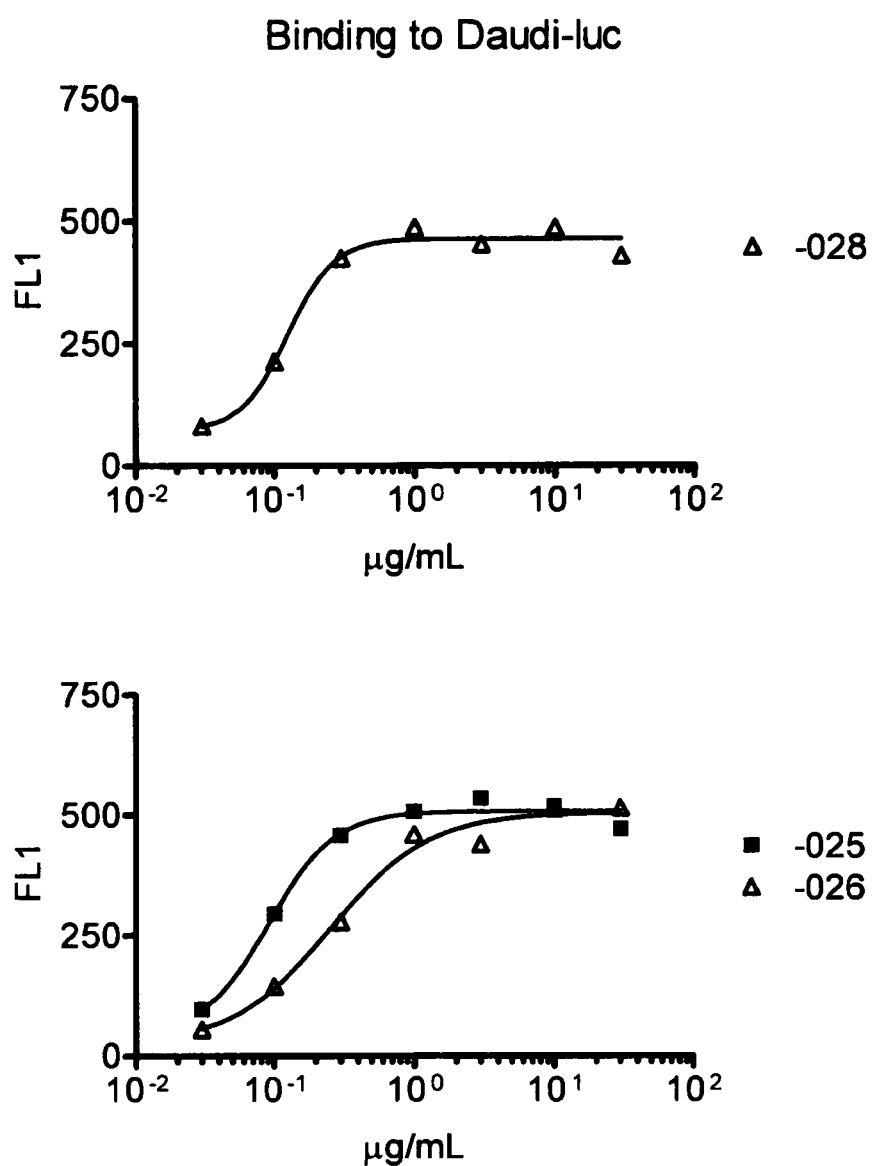
FIG. 3 shows binding of antibodies of the invention to Daudi-luc cells and CHO-CD38 cells.
Figure 3:
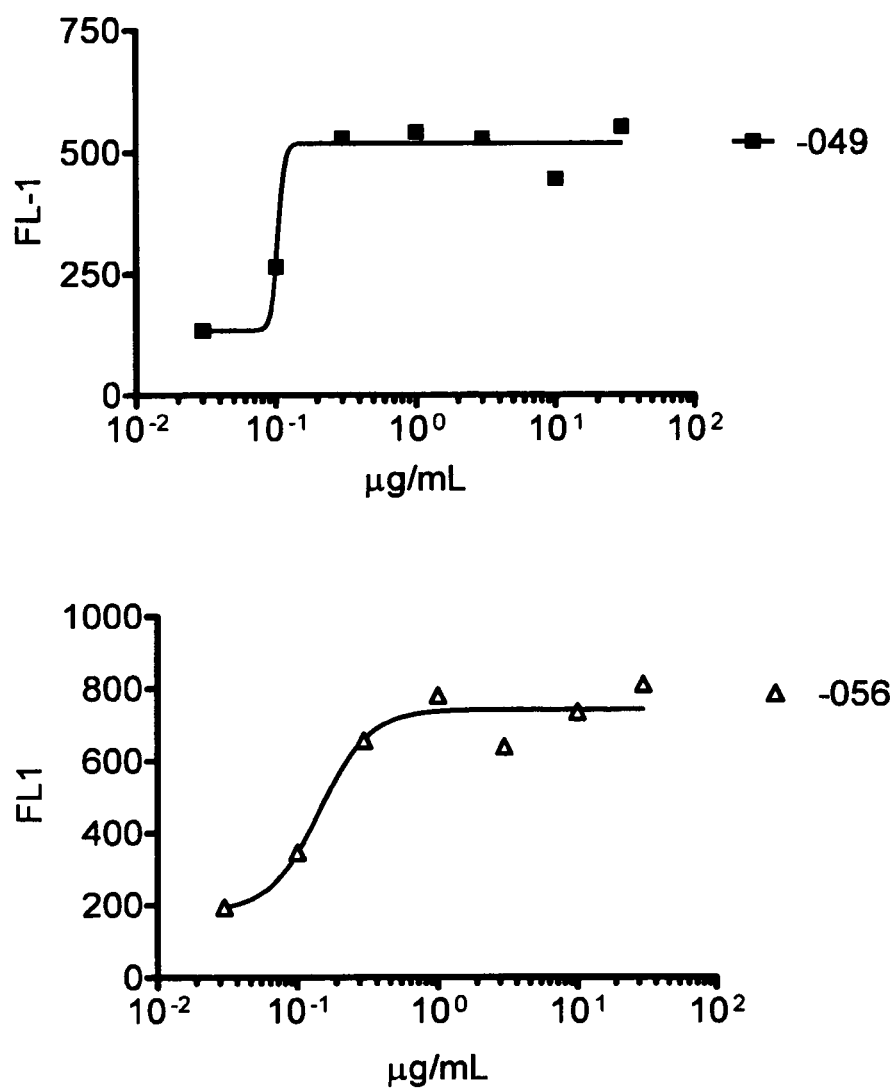
Figure 3:
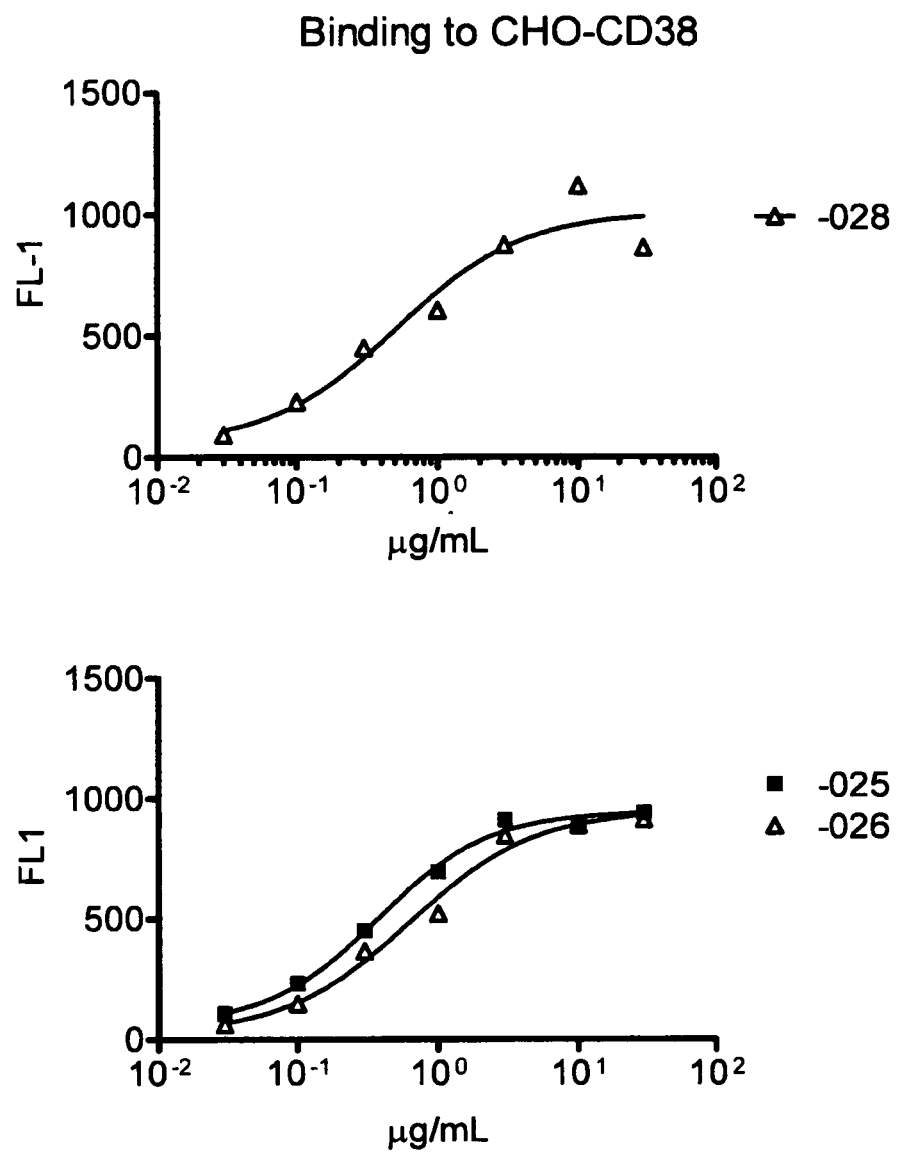
Figure 3:
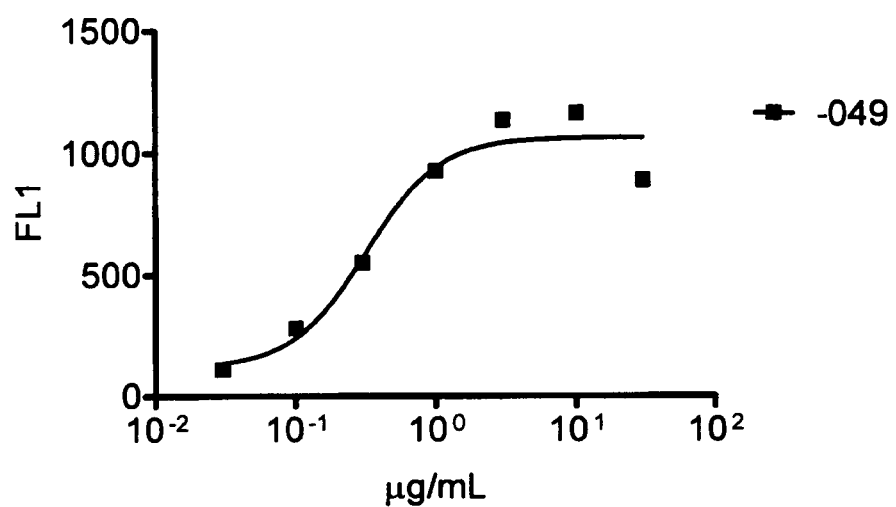
Figure 3:
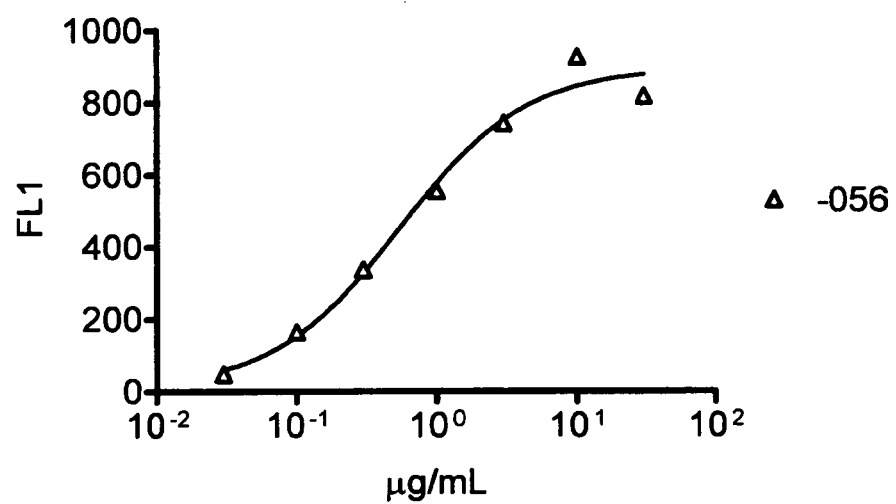

FIG. 3 shows that 025, 026, 028, 049, and 056 bind to CHO-CD38 cells and to Daudi-luc cells.

Example 6

Antibody-Dependent Cell-Mediated Cytotoxicity (ADCC)

The ability of anti-CD38 antibodies to perform ADCC of Daudi-luc cells was determined as explained below. As effector cells, peripheral blood mononuclear cells from healthy volunteers (UMC Utrecht, The Netherlands) were used.

Daudi-luc cells were collected ($5\times10^6$ cells) in RPMI (RPMI 1640 culture medium supplemented with 10% cosmic calf serum (HyClone, Logan, Utah, USA)), to which 100 µCi $^{51}$Cr (Chromium-51; Amersham Biosciences Europe GmbH, Roosendaal, The Netherlands) was added, and the mixture was incubated in a 37° C. water bath for 1 hr. After washing of the cells (twice in PBS, 1500 rpm, 5 min), the cells were resuspended in RPMI$^{++}$ and counted by trypan blue exclusion. Cells were brought at concentration of $1\times10^5$ cells/mL.

Preparation of Effector Cells

Fresh peripheral blood mononuclear cells (healthy volunteers, UMC Utrecht, Utrecht, The Netherlands) were isolated from 40 ml of heparin blood by Ficoll (Bio Whittaker; lymphocyte separation medium, cat 17-829E) according to the manufacturer's instructions. After resuspension of cells in RPMI$^{++}$, cells were counted by trypan blue exclusion and brought at concentration of $1\times10^7$ cells/ml.

ADCC Set Up

50 µl of $^{51}$Cr-labeled targets cells were pipetted into 96-well plates, and 50 µl of antibody was added, diluted in RPMI$^{++}$ (final concentrations 10, 1, 0.1, 0.01 µg/ml). Cells were incubated (RT, 15 min), and 50 µl effector cells were added, resulting in an effector to target ratio of 100:1 (for determination of maximal lysis, 100 µl 5% Triton-X100 was added instead of effector cells; for determination of spontaneous lysis, 50 µL target cells and 100 µL RPMI++ were used). Cells were spun down (500 rpm, 5 min), and incubated (37° C., 5% $CO_2$, 4 hr). After spinning down cells (1500 rpm, 5 min), 100 µL of supernatant was harvested into micronic tubes, and counted in gamma counter. The percentage specific lysis was calculated as follows:

(cpm sample−cpm target cells only)/(cpm maximal lysis−cpm target cells only)

wherein cpm is counts per minute.

Figure 4:
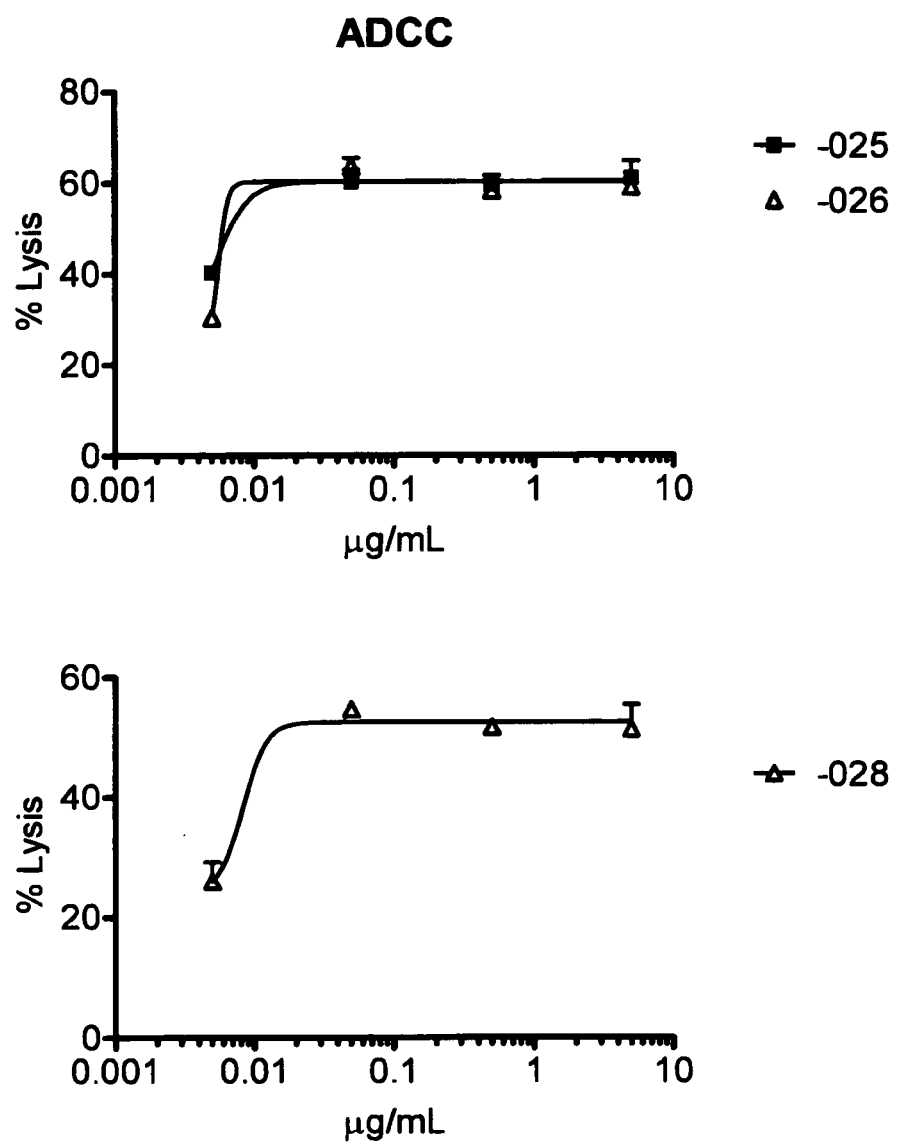
FIG. 4 shows ADCC mediated lysis of Daudi-luc cells caused by the anti-CD38 antibodies of the invention and as isotype control anti-KLH antibody (HuMab-KLH.
Figure 4:
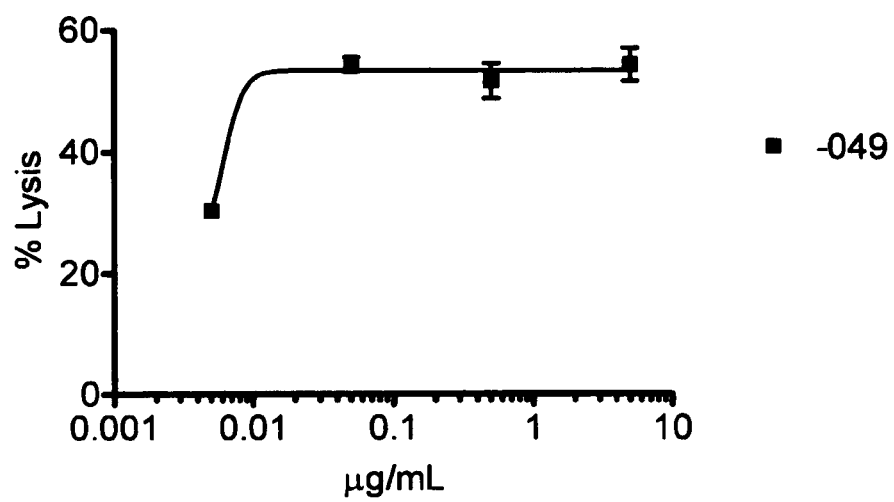
Figure 4:
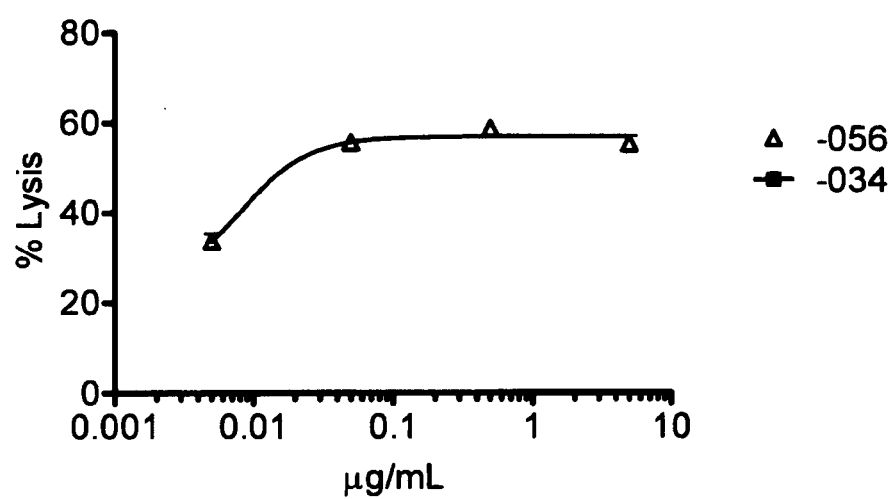

025, 026, 028, 049, and 056 induced ADCC mediated lysis in Daudi cells (FIG. 4).

Example 7

Complement-Dependent Cytotoxicity (CDC)

After harvesting and counting of Daudi-luc cells, the viability of the cells should be ≥90%. After washing (PBS), cells are resuspended at $2.0\times10^6$ cells/ml in RPMI-B (RPMI supplemented with 1% BSA). Thereafter, cells are put in 96-well round-bottom plates at $1\times10^5$ cells/well (50 µL/well). Then, 50 µL antibodies is added to the wells (final concentration range between 0-100 µg/ml (three-fold dilutions in RPMI-B)). After incubation (RT, 15 min), 11 µL of pooled human serum (pool of 18 healthy donors) was added to each well (37° C., 45 min). Wells were resuspended once and 120 µL was transferred to FACS tubes (Greiner). Then, 10 µL propidium iodide (PI; Sigma-Aldrich Chemie B.V.) was added (10 µg/ml solution) to this suspension. Lysis was detected by flow cytometry (FACScalibur™, Becton Dickinson, San Diego, Calif., USA) by measurement of the percentage of dead cells (corresponds to PI-positive cells).

Figure 5:
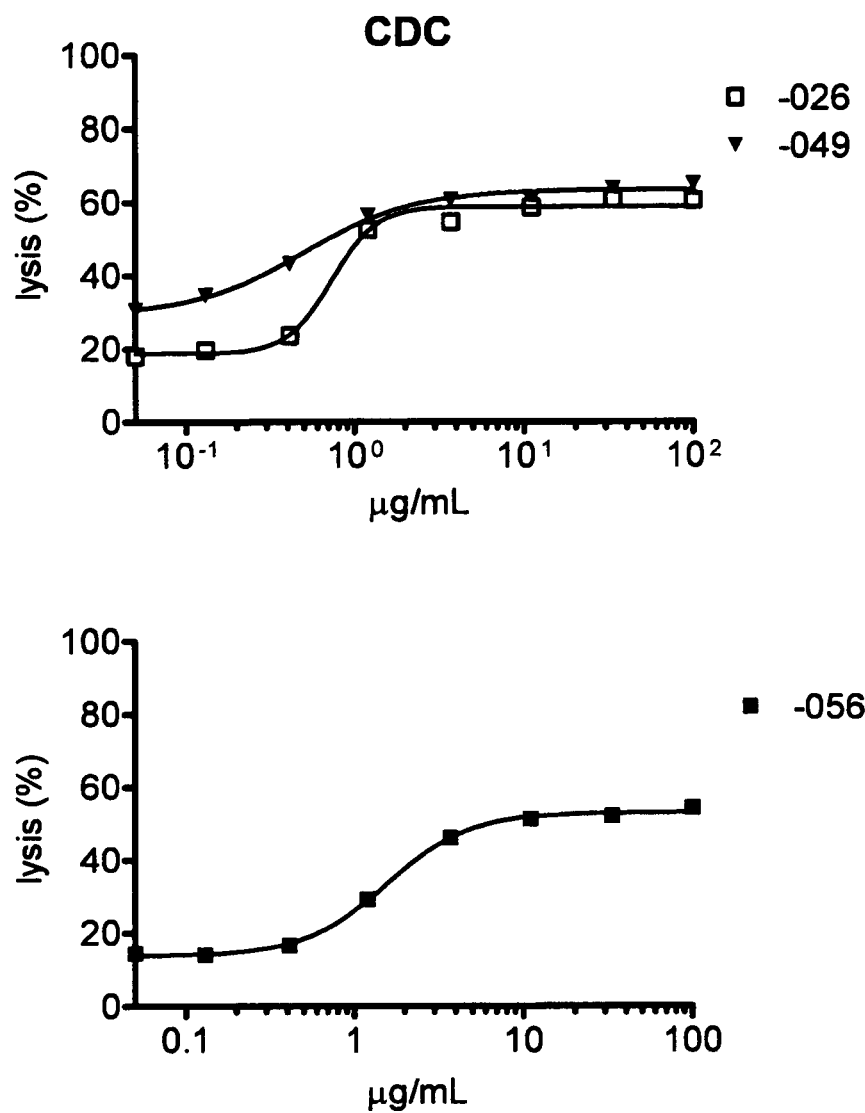
FIG. 5 shows CDC mediated lysis of CHO CD38 cells caused by the anti-CD38 antibodies of the invention.
Figure 5:
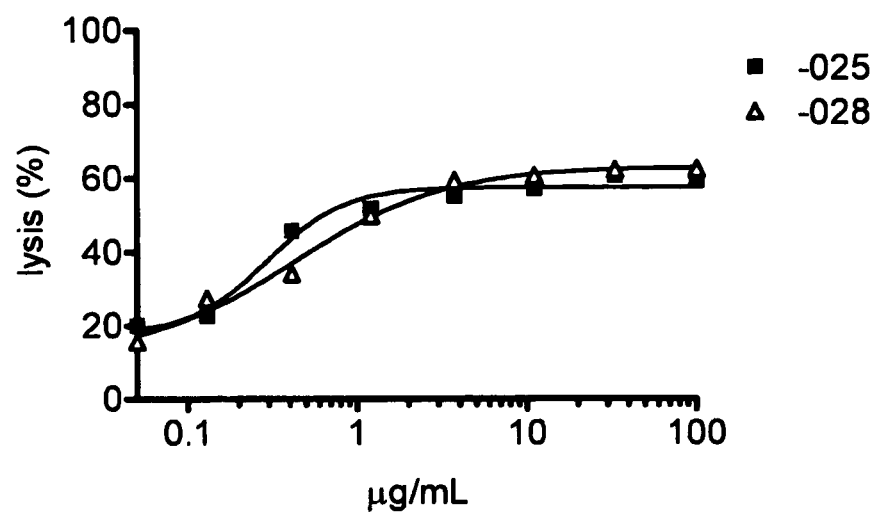

FIG. 5 presents CDC-mediated CHO-CD38 cell lysis caused by anti-CD38 antibodies 025, 026, 028, 049 and 056. These anti-CD38 antibodies failed to induce CDC of Daudi-luc cells.

Example 8

Enzymatic Activity

The effects of anti-CD38 antibodies on the enzymatic activities of CD38 were determined. CD38 is known to catalyze several different enzymatic reactions, including a cyclase reaction converting NAD into cyclic ADP ribose (cADPR), a hydrolase reaction converting NAD or cADPR into ADP ribose, and a base-exchange reaction in which nicotinic acid adenine dinucleotide 2'-phosphate (NAADP) is produced.

Cyclase Activity
NGD Assay

The ability of anti-CD38 antibodies to interfere with the cyclase activity of CD38 using NGD as a substrate was measured in an assay essentially as described in Graeff et al., J. Biol. Chem. 269, 30260-30267 (1994):

Briefly, substrate NGD$^+$ (80 µM) was incubated with CD38 (0.6 µg/ml His-tagged extracellular domain of human CD38, see Example 3 of WO2006099875 regarding purification of His-CD38 in a buffer containing 20 mM Tris-HCl, pH 7.0). The production of cGDPR can be monitored spectrophotometrically at the emission wavelength of 410 nm (excitation at 300 nm). In this example an excitation filter of 340±60 nm and an emission filter of 430±8 nm were used.

To test the effect of 025, 026, 028, 049 and 056 on the enzymatic activity of CD38, recombinant His-CD38 protein was pre-incubated for 15 minutes at room temperature with 3 µg/ml of the antibodies before adding the substrate NGD$^+$. The production of cyclic GDP-ribose (cGDPR) was recorded after 90 minutes.

Figure 6:
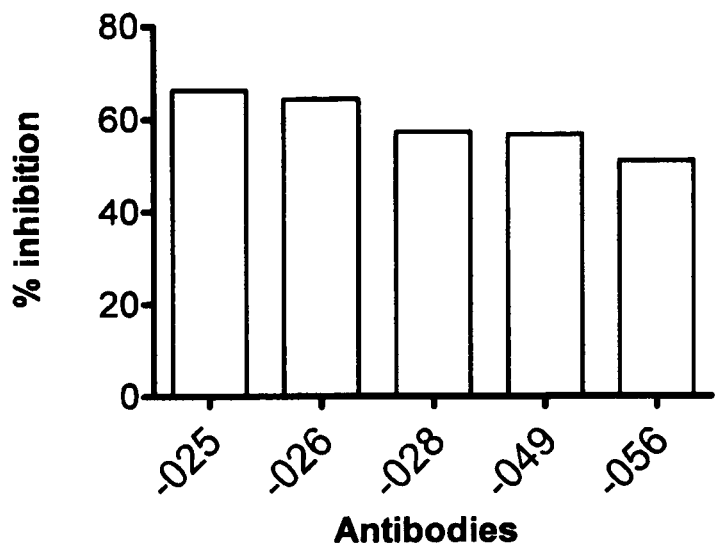
FIG. 6 shows inhibition of cGDPR production by His-tagged CD38 protein and cellular expressed CD38 in the presence of the anti-CD38 antibodies of the invention.
Figure 6:
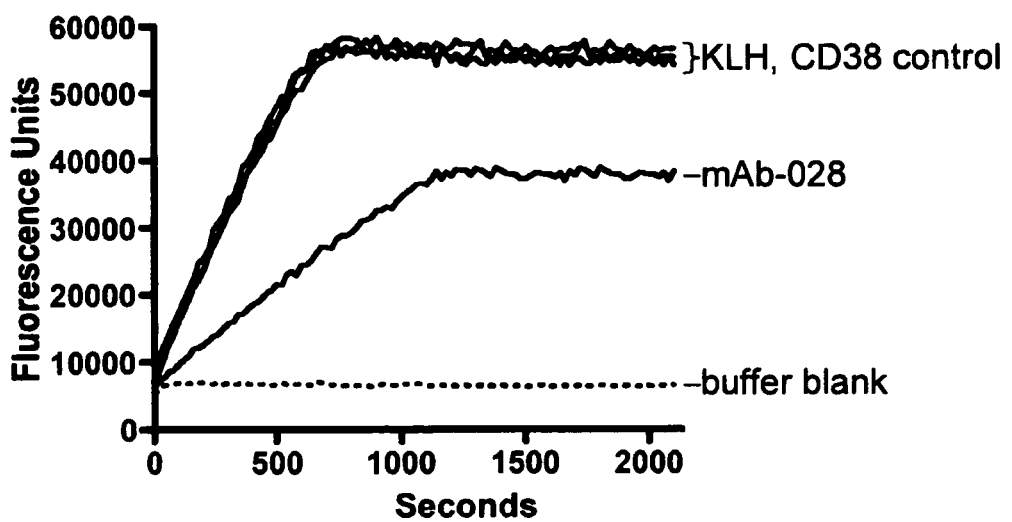
Figure 6:
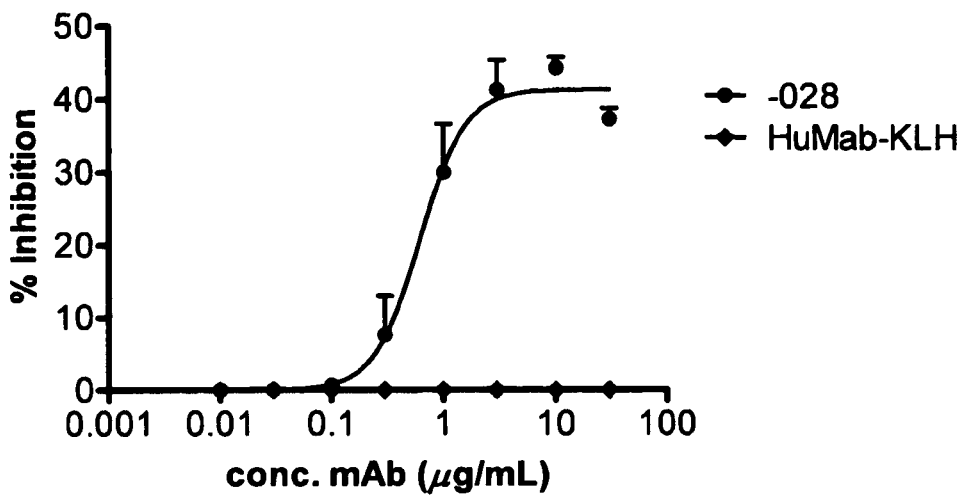
Figure 6:
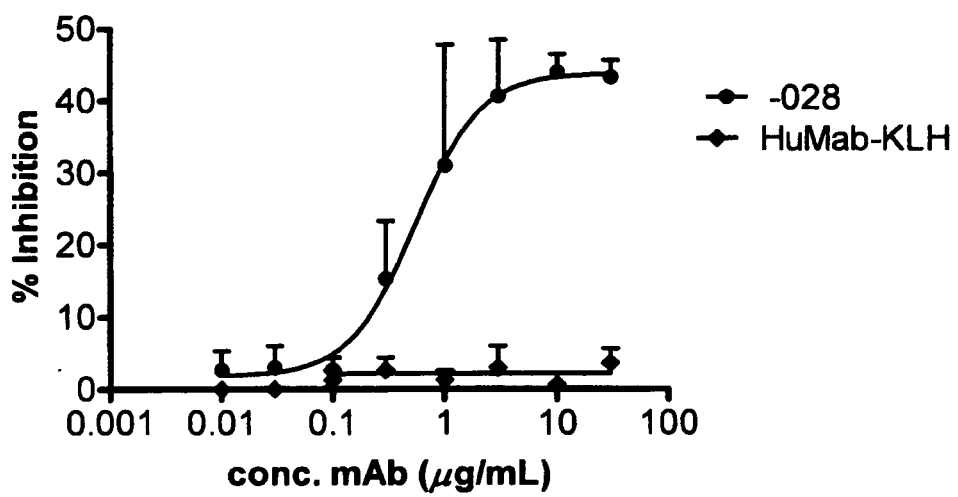

FIG. 6A shows that antibodies 025, 026, 028, 049 and 056 have a pronounced inhibitory effect on the production of cGDPR. After 90 minutes, 3 µg/ml of antibody (025, 026, 028, 049 or 056) resulted in a 53-66% reduced production of cGDPR. In a time course experiment it was shown that the rate of cGDPR production was reduced in samples treated with the CD38-specific antibody mAb 028 compared to the cGDPR production in the presence of HuMab-KLH or in the untreated CD38 control (FIG. 6B). FIG. 6C shows a dose response curve (0.01-30 µg/ml) for antibody 028. In this experiment a maximum reduction of cGDPR production of 41% is observed.

To test the effect of 028 on the enzymatic activity of cellular expressed CD38, CHO-CDC38 cells were pre-incubated for 30 minutes at room temperature with a serial dilution of 028 (0.01-30 µg/ml) before adding the substrate NGD$^+$. The production of cyclic GDP-ribose (cGDPR) was recorded after 90 min. As shown in FIG. 6D antibody 028 inhibits the production of cGDPR in a concentration dependent fashion.

Reverse Cyclase Reaction

The effect of mAb 028 on cADPR production from NAD by CD38 was determined by the reverse cyclase reaction. This assay is based on the reversibility of the reaction catalyzed by CD38. In the presence of high concentrations of nicotinamide and cADPR, the ADP-ribosyl cyclases can produce NAD. Antibodies were diluted to 10 µg/ml in 20 mM Tris-HCl, 0.01% (v/v) BSA, pH 7.2 (Tris/BSA). Human recombinant CD38 was diluted to 2 µg/ml with Tris/BSA. The antibodies were preincubated for 10 minutes with CD38 by mixing equal volumes (50 µL) of the diluted antibodies with the diluted CD38. The preincubation was done at room temperature. The reaction was initiated by transferring 25 µL of CD38/antibody mixture to 25 µL of a solution containing 1 mM cADPR and 10 mM nicotinamide. The reaction was allowed to proceed at room temperature for 1 to 20 minutes and was stopped at the appropriate time by filtering the entire sample through a Millipore MultiScreen-IP Filter 96-well plate to remove protein. The resulting NAD produced was measured by the method of Graeff and Lee (1). Controls containing nicotinamide without cADPR were run to estimate the amount NAD contaminating the reagents. In these experiments there was undetectable contaminating NAD.

Table 2 shows that 1 µg/ml mAb-028 reduced cADPR production from NAD by 67%. mAb-KLH had no effect on cADPR production from NAD.

TABLE 2

The effect of antibody 028 on cADPR production from NAD

| Condition | pmol cADPR/min |
|---|---|
| CD38 control | 4.3 |
| mAb-KLH | 4.3 |
| mAb-028 | 1.4 |

8-Amino-NAD (8NH2-NAD) Assay

As cADPR production only accounts for approximately 1% of the product generated from NAD by CD38 (ADPR accounts for the rest), ribosyl cyclase activity was also assessed using 8-amino-NAD (8NH2-NAD) as a substrate. Unlike NAD, a considerably larger amount (approximately 8%) of the 8NH2-NAD substrate is cyclized to 8-amino-cADPR (8NH2-cADPR) and is detectable by HPLC analysis. Briefly, antibodies were diluted to 10 µg/mL in 20 mM Tris-HCl, 0.01% (v/v) BSA, pH 7.2 (Tris/BSA). Human recombinant CD38 was diluted to 2 µg/ml with Tris/BSA. The antibodies were preincubated for 10 minutes with CD38 by mixing equal volumes (50 µL) of the diluted antibodies with the diluted CD38. The preincubation was done at room temperature. The reaction was initiated by transferring 25 µL of CD38/antibody mixture to 75 µL of 0.5 mM 8NH2-NAD. The reaction was allowed to proceed at room temperature for 10 minutes and was stopped at the appropriate time by filtering the entire sample through a Millipore MultiScreen-IP Filter 96-well plate to remove protein. The reaction products (8NH2-cADPR and 8NH2-ADPR) were analyzed by reverse phase HPLC as follows. The column was a 0.46×15 cm LC18-T reverse phase column from Supelco. Solvent A consisted of 20 mM KH2PO4, 5 mM tetrabutylammonium phosphate, pH 6 and solvent B consisted of 50% A and 50% methanol. The flow rate was 1 mL/min and the initial composition of solvents was 15% B. Separation of substrates and products was accomplished using the following gradient: 0 to 3.5 minutes (15% B), 3.5 to 5.5 minutes (15 to 32.5% B), 5.5 to 9 minutes (32.5 to 40% B), 9 to 11.5 minutes (40 to 50% B) and 16 to 18 minutes (50 to 15% B) gradient was used to elute the substrates and products. Samples were prepared by adding 400 µL of solvent A to 100 µL of filtered sample. The entire sample was injected. The flow rate and buffer composition were controlled by Beckman 125 HPLC pumps and System Gold software and peaks were detected with a Beckman 166 UV detector. The areas of the 8NH2-NAD, 8NH2-cADPR and 8NH2-ADPR peaks were used to calculate the amount of 8NH2-cADPR produced in the assay. The HPLC system is based on a system described by Schweitzer et al. (2).

Figure 7:
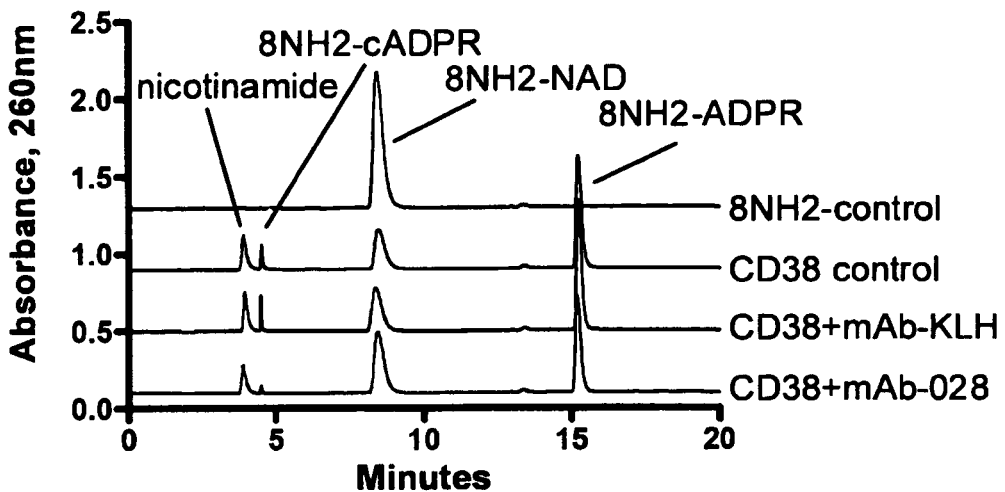
FIG. 7 shows the effect of antibody 028 of the invention on 8NH2-cADPR production. Products of each reaction were analyzed by HPLC.
Figure 7:
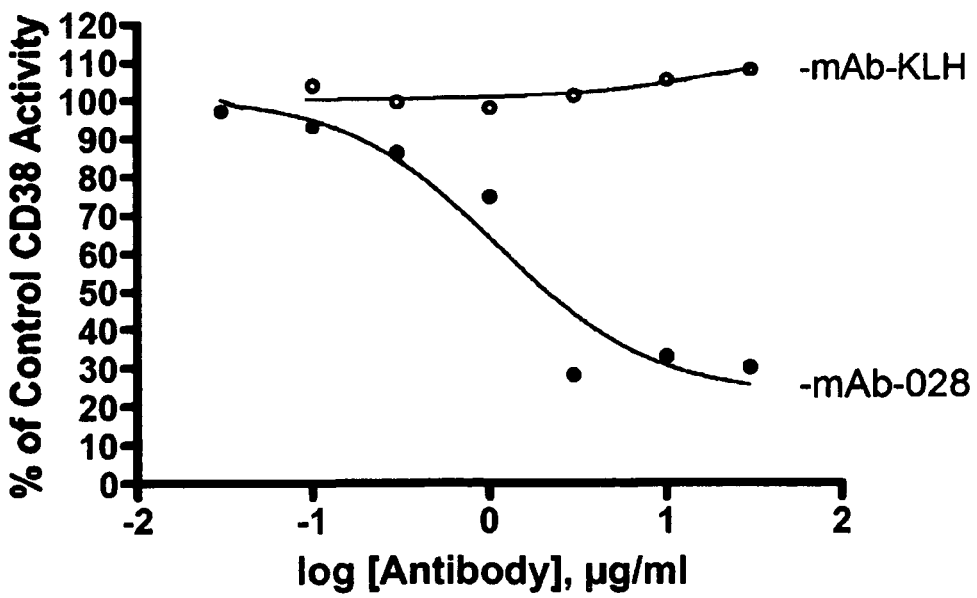

FIG. 7A shows that mAb-028 inhibits 8NH2-cADPR by 78%. mAb-028 inhibits 8NH2-cADPR production in a concentration dependent manner (FIG. 7B)

Thus mAb-028 inhibits the ADP-ribosyl cyclase reaction of CD38 as assayed by three different methods.

Hydrolase Activity
Hydrolase Activity Analysis by HPLC

The hydrolase activity was measured by determining the amount of ADPR produced from cADPR or NAD by HPLC. Antibodies were diluted to 10 µg/mL or titrated in 20 mM Tris-HCl, 0.01% (v/v) BSA, pH 7.2 (Tris/BSA). Human recombinant CD38 was diluted to 2 µg/mL with Tris/BSA. The antibodies were preincubated for 10 minutes with CD38 by mixing equal volumes (50 µL) of the diluted antibodies with the diluted CD38. The preincubation was done at room temperature. For the HPLC-based method the cADPR hydrolase reaction was initiated by transferring 40 µL of CD38/antibody mixture to 10 µL of 4.3 mM cADPR and the NADase reaction was initiated by transferring 40 µL of CD38/antibody mixture to 10 µL 1 mM NAD. The reaction was allowed to proceed at room temperature and was stopped at the appropriate time by adding 25 µL of 1 M HCl. Protein was removed by filtering the entire sample through a Millipore MultiScreen-IP Filter 96-well plate. Each filtrate was neutralized by adding 15 µL of 2M Tris-base and kept on ice until analyzed by HPLC. The analysis of hydrolase activity is based on the HPLC assay developed by Lee and Aarhus (3). The samples were analyzed on a 0.5×5 cm column of AG MP-1 (trifluoroacetate form) eluted at 3 mL/min with a 0 to 150 mM concave upward gradient of trifluoroacetic acid (TFA) over 10 minutes. The flow rate and buffer composition were controlled by Beckman 125 HPLC pumps and System Gold software and peaks were detected with a Beckman 166 UV detector. The areas of NAD, cADPR and ADPR were used to calculate the amount of ADPR produced in the assay.

Figure 8:
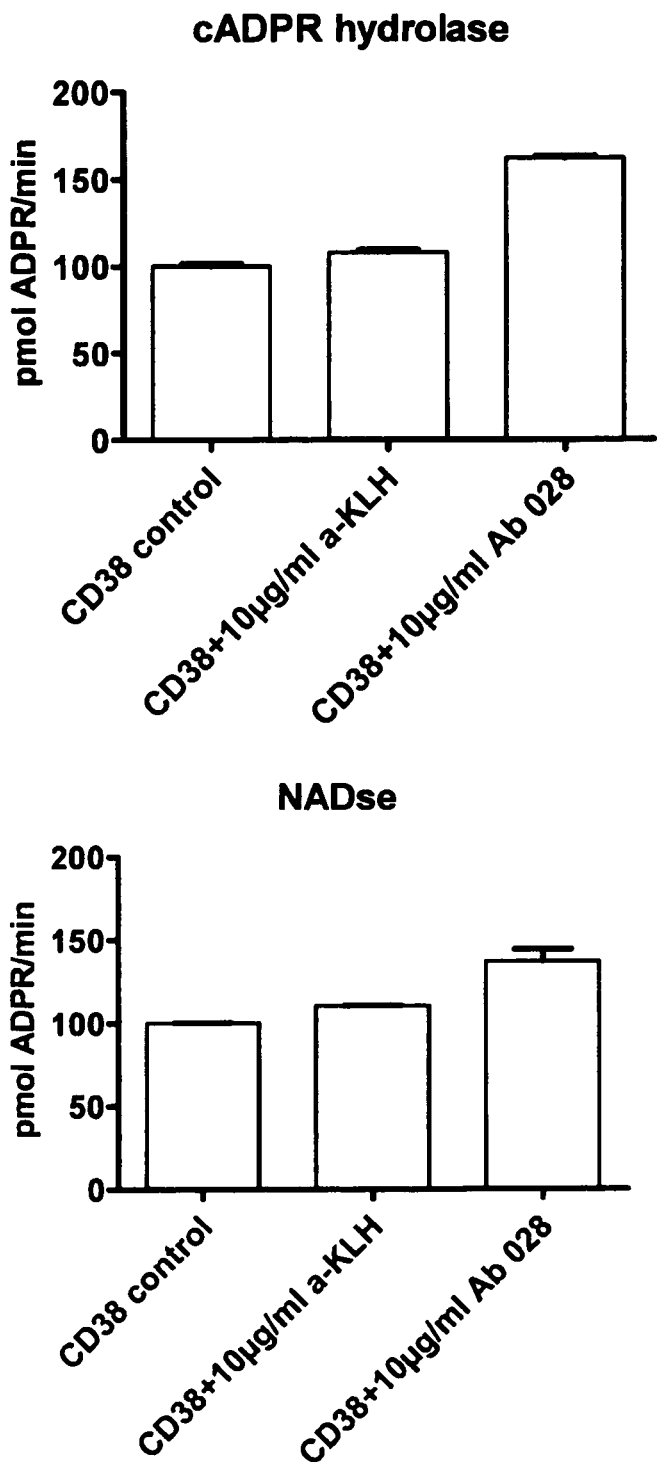
FIG. 8 shows the effect of antibody 028 of the invention on cADPR hydrolase and NADa se activity, more particularly the effect of mAb-028 on cADPR hydrolase (Figure A, upper figure, B and C) and NADse (Figure A, bottom figure) activity.
Figure 8:
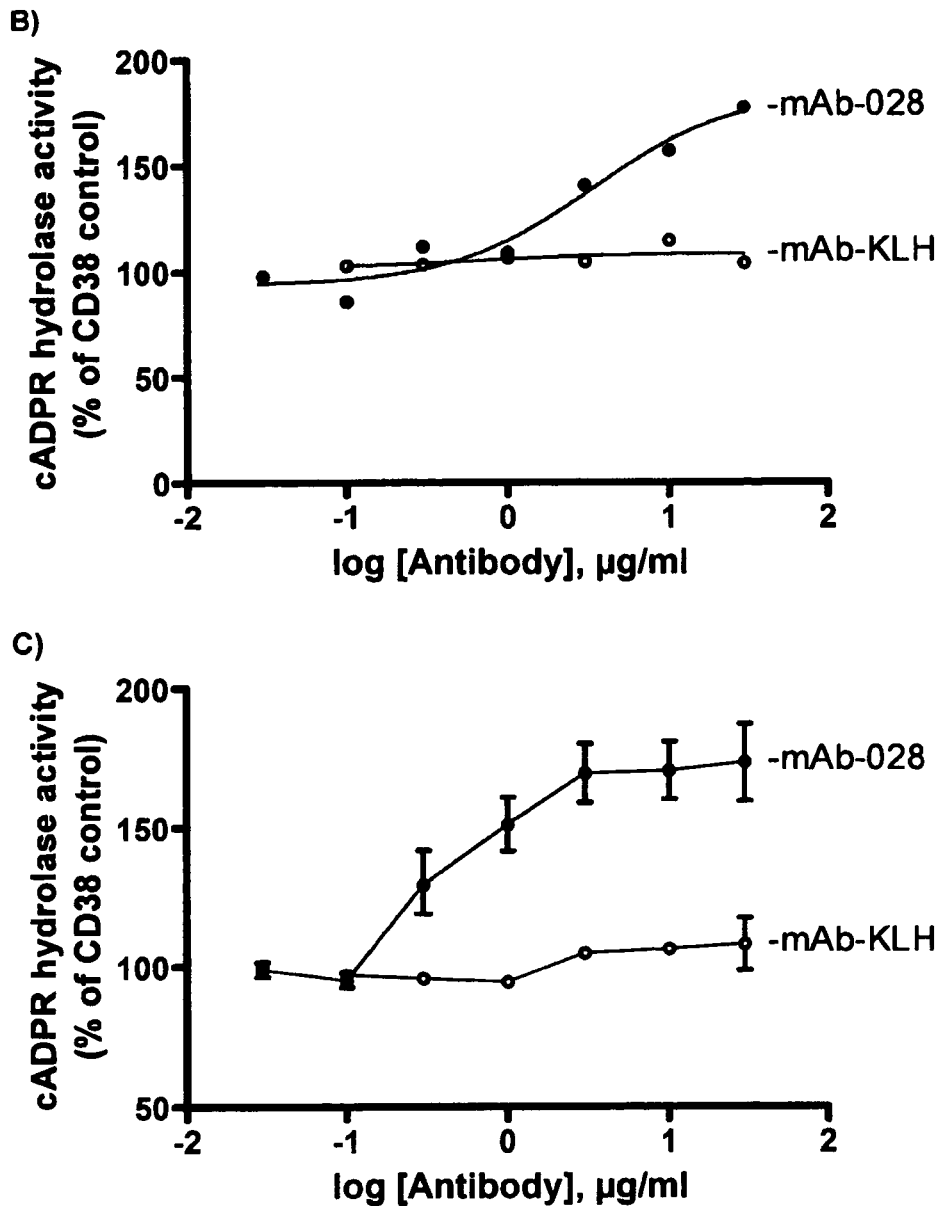

At concentrations of 10 µg/mL mAb-028, but not mAb-KLH, stimulated the cADPR hydrolase activity by 62% and the NAD hydrolase activity by 37% compared to the CD38 control (FIG. 8A). FIG. 8B shows that mAb-028 stimulated cADPR hydrolysis in a dose-dependent manner. At concentrations of 30 µg/mL, mAb-028 stimulated hydrolase activity by 78%.

Hydrolase Activity Analysis by Thin Layer Chromatography (TLC)

The hydrolase activity was measured by measuring the amount of $^{32}$P-ADPR produced from $^{32}$P-cADPR by thin layer chromatography (4). The $^{32}$P-based cADPR hydrolase reaction was initiated by adding 20 µL of CD38/antibody mixture (as above) to 5 µL of a mixture containing 0.5 mM cADPR and approximately 0.1 µCi of $^{32}$P-cADPR. The reaction was allowed to proceed at room temperature and at the appropriate times, 5 µL of the reaction was added to 5 µL of 150 mM TFA to stop the reaction. The reaction was analyzed by PEI-cellulose thin layer chromatography (TLC). One (1) µL of each stopped reaction sample was spotted on the origin of a PEI-cellulose TLC plate (10×20 cm). The plates were developed with 0.2 M NaCl in 30% (v/v) ethanol. The plates were dried and exposed to phosphoimage screens. The screens were analyzed on a Packard Cyclone Phosphorimager to determine the amount of $^{32}$P-ADPR produced.

FIG. 8C shows that mAb-028 stimulated $^{32}$P-cADPR hydrolysis in a dose-dependent manner. These results were similar to the results of the cADPR hydrolase activity measured by HPLC (see FIG. 8B).

Base-Exchange Activity

The effect of CD38 antibodies on nicotinic acid adenine dinucleotide 2'-phosphate (NAADP) synthesis by the base-exchange activity of CD38 was assessed. Antibodies (mAb-KLH and 028) were diluted to 40 µg/mL in 20 mM Hepes, pH 7.3, 0.01% (v/v) BSA (Hepes/BSA). Human recombinant CD38 was diluted to 2 µg/mL with Hepes/BSA. The antibodies were preincubated for 10 minutes with CD38 by mixing equal volumes (90 µL) of the diluted antibodies with the diluted CD38. The preincubation was performed at room temperature. The base-exchange reaction was initiated by transferring 50 µL of CD38/antibody mixture to 50 µL of a reaction mixture containing 200 mM sodium acetate, pH 4.0, 25 mM nicotinic acid and 2 mM nicotinamide adenine dinucleotide 2'-phosphate (NADP). The reaction was allowed to proceed at room temperature for 30 minutes and was stopped by filtering the entire sample through a Millipore MultiScreen-IP Filter 96-well plate to remove protein. The reaction products in the filtrates were determined by anion-exchange HPLC on a 0.5×5 cm column of AG MP-1 (trifluoroacetate form) eluted at 1 mL/min with a 0 to 150 mM concave upward gradient of trifluoroacetic acid (TFA) over 30 minutes (5). The filtrates (50 µL) were neutralized by adding 5 µL of 2 M Tris-base just prior to injection. The flow rate and buffer composition were controlled by Beckman 125 HPLC pumps and System Gold software and peaks were detected with a Beckman 166 UV detector. The areas of the NADP, NAADP (base-exchange product) and adenosine diphospho-ribose 2'-phosphate (ADPR-P, hydrolytic product) peaks were used to calculate the rates of NAADP synthesis and NADP hydrolysis.

Figure 9:
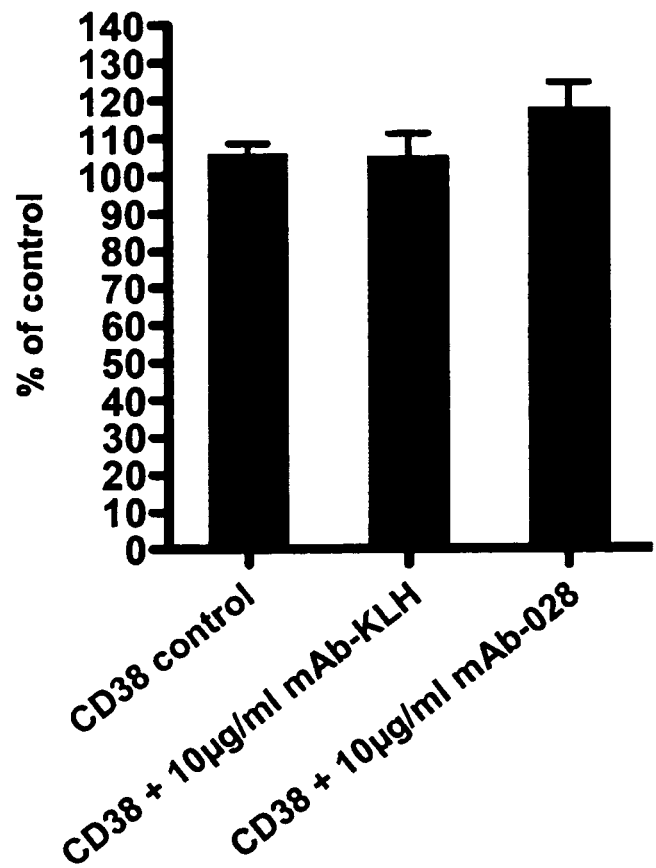
FIG. 9 shows the effect of the anti-CD38 antibodies of the invention on the base-exchange activity of CD38.
Figure 9:
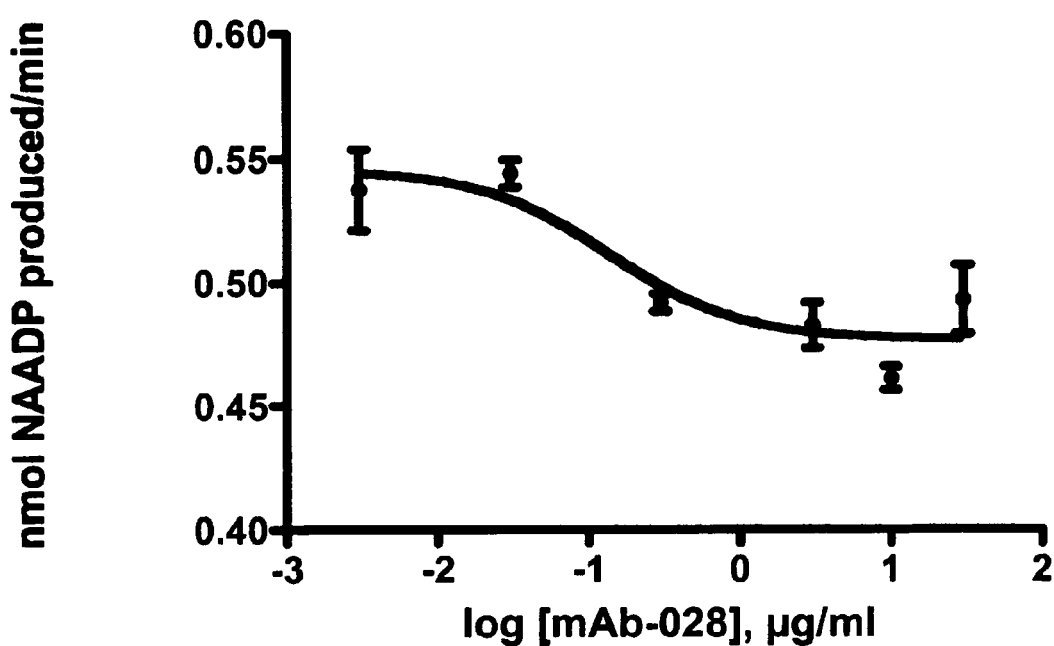

FIG. 9 shows that mAb-028 inhibits the ability of CD38 to catalyze the formation of NAADP. The inhibition of NAADP production by mAb-028 is concentration dependent (FIG. 9B) with an IC50 of 0.14 µg/mL.

LIST OF REFERENCES

1. Graeff, R., and H. C. Lee. 2002. A novel cycling assay for cellular cADP-ribose with nanomolar sensitivity. *Biochem J* 361:379-384.
2. Schweitzer, K., G. W. Mayr, and A. H. Guse. 2001. Assay for ADP-ribosyl cyclase by reverse-phase high-performance liquid chromatography. *Anal Biochem* 299:218-226.
3. Lee, H. C., and R. Aarhus. 1993. Wide distribution of an enzyme that catalyzes the hydrolysis of cyclic ADP-ribose. *Biochim Biophys Acta* 1164:68-74.
4. White, T. A., S. Johnson, T. F. Walseth, H. C. Lee, R. M. Graeff, C. B. Munshi, Y. S. Prakash, G. C. Sieck, and M. S. Kannan. 2000. Subcellular localization of cyclic ADP-ribosyl cyclase and cyclic ADP-ribose hydrolase activities in porcine airway smooth muscle. *Biochim Biophys Acta* 1498:64-71.
5. Aarhus, R., R. M. Graeff, D. M. Dickey, T. F. Walseth, and H. C. Lee. 1995. ADP-ribosyl cyclase and CD38 catalyze the synthesis of a calcium-mobilizing metabolite from NADP. *J Biol Chem* 270:30327-30333.

The invention claimed is:

1. An isolated antibody that binds to human CD38, which antibody is encoded by a human heavy chain nucleic acid comprising a nucleotide sequence in its variable region as set forth in SEQ ID NO: 1, 6, 11, 16 or 21, and a human light chain nucleic acid comprising a nucleotide sequence in its variable region as set forth in SEQ ID NOs: 26, 31, 36, 41 or 46.

2. The antibody of claim 1, which antibody is encoded by a human heavy chain and a human light chain nucleic acid comprising nucleotide sequences in their variable regions as set forth in SEQ ID NOs: 1 and 26, 6 and 31, 11 and 36, 16 and 41, or 21 and 46, respectively.

3. An isolated human antibody that binds to CD38, wherein the antibody comprises
(i) a VH CDR1 having the sequence as set forth in any one of SEQ ID NOs: 3, 8, 13, 18 and 23, a VH CDR2 having the sequence as set forth in any one of SEQ ID NOs: 4, 9, 14, 19 and 24, a VH CDR3 having the sequence as set forth in any one of SEQ ID NOs: 5, 10, 15, 20 and 25, a VL CDR1 having the sequence as set forth in any one of SEQ ID NOs: 28, 33, 38, 43 and 48, a VL CDR2 having the sequence as set forth in any one of SEQ ID NOs: 29, 34, 39, 44 and 49, and a VL CDR3 having the sequence as set forth in any one of SEQ ID NOs: 30, 35, 40, 45 and 50,
(ii) a VH CDR1 having the sequence as set forth in SEQ ID NO: 3, a VH CDR2 having the sequence as set forth in SEQ ID NO: 4, a VH CDR3 having the sequence as set forth in SEQ ID NO: 5, a VL CDR1 having the sequence as set forth in SEQ ID NO: 28, a VL CDR2 having the sequence as set forth in SEQ ID NO: 29, and a VL CDR3 having the sequence as set forth in SEQ ID NO: 30,
(iii) a VH CDR1 having the sequence as set forth in SEQ ID NO: 8, a VH CDR2 having the sequence as set forth in SEQ ID NO: 9, a VH CDR3 having the sequence as set forth in SEQ ID NO: 10, a VL CDR1 having the sequence as set forth in SEQ ID NO: 33, a VL CDR2 having the sequence as set forth in SEQ ID NO: 34, and a VL CDR3 having the sequence as set forth in SEQ ID NO: 35,
(iv) a VH CDR1 having the sequence as set forth in SEQ ID NO: 13, a VH CDR2 having the sequence as set forth in SEQ ID NO: 14, a VH CDR3 having the sequence as set forth in SEQ ID NO: 15, a VL CDR1 having the sequence as set forth in SEQ ID NO: 38, a VL CDR2 having the sequence as set forth in SEQ ID NO: 39, and a VL CDR3 having the sequence as set forth in SEQ ID NO: 40,
(v) a VH CDR1 having the sequence as set forth in SEQ ID NO: 18, a VH CDR2 having the sequence as set forth in SEQ ID NO: 19, a VH CDR3 having the sequence as set forth in SEQ ID NO: 20, a VL CDR1 having the sequence as set forth in SEQ ID NO: 43, a VL CDR2 having the sequence as set forth in SEQ ID NO: 44, and a VL CDR3 having the sequence as set forth in SEQ ID NO: 45, or
(vi) a VH CDR1 having the sequence as set forth in SEQ ID NO: 23, a VH CDR2 having the sequence as set forth in SEQ ID NO: 24, a VH CDR3 having the sequence as set forth in SEQ ID NO: 25, a VL CDR1 having the sequence as set forth in SEQ ID NO 48, a VL CDR2 having the sequence as set forth in SEQ ID NO: 49, and a VL CDR3 having the sequence as set forth in SEQ ID NO: 50.

4. An isolated antibody that binds to CD38 comprising a VH region comprising any one of the sequences as set forth in SEQ ID NOs: 2, 7, 12, 17 and 22, and a VL region comprising any one of the sequences as set forth in SEQ ID NOs: 27, 32, 37, 42 and 47.

5. An isolated antibody that binds to CD38 comprising
(i) a VH region comprising the sequence as set forth in SEQ ID NO: 2, and a VL region comprising the sequence as set forth in SEQ ID NO: 27,
(ii) a VH region comprising the sequence as set forth in SEQ ID NO: 7, and a VL region comprising the sequence as set forth in SEQ ID NO: 32,
(iii) a VH region comprising the sequence as set forth in SEQ ID NO: 12, and a VL region comprising the sequence as set forth in SEQ ID NO: 37,
(iv) a VH region comprising the sequence as set forth in SEQ ID NO: 17, and a VL region comprising the sequence as set forth in SEQ ID NO: 42, or
(v) a VH region comprising the sequence as set forth in SEQ ID NO: 22, and a VL region comprising the sequence as set forth in SEQ ID NO: 47.

6. The antibody of claim 1, wherein the antibody does not bind to a variant of human CD38 wherein Asp in position 202 has been substituted with Gly to the same degree that it binds to human CD38.

7. The antibody of claim 3 or 5 that binds human CD38 and has an inhibitory effect on CD38 cyclase activity and a stimulatory effect on CD38 hydrolase activity.

8. The antibody of claim 7, wherein the inhibitory effect is at least 50-66% compared to the inhibitory effect on CD38 cyclase activity in the absence of antibody.

9. The antibody of claim 3 or 5, wherein the antibody is capable of inducing antibody-dependent cellular cytotoxicity (ADCC).

10. The antibody of claim 3 or 5, wherein the antibody is not capable of inducing ADCC in Daudi cells.

11. The antibody of claim 3 or 5, wherein the antibody is not capable of inducing complement-dependent cytotoxicity (CDC) in CHO-CD38 cells.

12. The antibody of claim 3 or 5, wherein the antibody binds to human CD38 with a $K_D$ of $10^{-8}$ M or less.

13. The antibody of any one of claims 1, 3, 4, and 5, which is a human monovalent antibody.

14. The antibody of any one of claims 1, 3, 4, and 5, characterized in that it is a full length IgG1, IgG2, IgG3, IgG4, IgD, IgA, IgE, or IgM antibody.

15. The antibody of claim 3 or 5, wherein the antibody is an antibody fragment or a single-chain antibody.

16. The antibody of claim 3 or 5, wherein the antibody is an effector-function-deficient antibody.

17. The antibody of claim 16, wherein the effector-function-deficient antibody is a stabilized human IgG4 antibody.

18. The antibody of claim 17, wherein the stabilized IgG4 antibody is an antibody wherein arginine at position 409 in the heavy chain constant region of human IgG4 is substituted with lysine, threonine, methionine, or leucine.

19. The antibody of claim 18, wherein said antibody comprises a Lys residue at the position corresponding to 409 or the CH3 region of the antibody has been replaced by the CH3 region of human IgG1, of human IgG2 or of human IgG3.

20. The antibody of claim 18, wherein said antibody does not comprise a Cys-Pro-Pro-Cys (SEQ ID NO: 53) sequence in the hinge region.

21. The antibody of claim 18, wherein said antibody comprises a Cys-Pro-Pro-Cys (SEQ ID NO: 53) sequence in the hinge region.

22. The antibody of claim 3 or 5, wherein the antibody is a monovalent antibody.

23. The antibody of claim 22, wherein said monovalent antibody is constructed by a method comprising:
i) providing a nucleic acid construct encoding the light chain of said monovalent antibody, said construct comprising a nucleotide sequence encoding the VL region of SEQ ID NO: 27, 32, 37, 42 or 47 and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of SEQ ID NO: 2, 7, 12 17 or 22 and a nucleotide sequence encoding a constant CH region of a human Ig, wherein the nucleotide sequence encoding the CH region has been modified such that the region corresponding to the hinge region and, as required by the Ig subtype, other regions of the CH region do not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal or human being, wherein said nucleotide sequence encoding the VH region of a selected antigen specific antibody and said nucleotide sequence encoding the CH region of said Ig are operably linked together;

iii) providing a cell expression system for producing said monovalent antibody; and iv) producing said monovalent antibody by co-expressing the nucleic acid constructs of (i) and (ii) in cells of the cell expression system of (iii).

24. The antibody of claim 22, wherein the $C_H$ region comprising the $C_H2$ and $C_H3$ regions has been modified such that the region corresponding to the hinge region and, if the immunoglobulin is not an IgG4 subtype, other regions of the $C_H$ region do not comprise any amino acid residues which are capable of forming disulfide bonds with an identical $C_H$ region or other covalent or stable non-covalent inter-heavy chain bonds with an identical $C_H$ region in the presence of polyclonal human IgG.

25. The antibody of claim 22, wherein said monovalent antibody is of the IgG4 subtype, but the $C_H3$ region has been modified so that one or more of the following amino acid substitutions have been made: Thr (T) in position 366 has been replaced by Ala (A); Leu (L) in position 368 has been replaced by Ala (A); Leu (L) in position 368 has been replaced by Val (V); Phe (F) in position 405 has been replaced by Ala (A); Phe (F) in position 405 has been replaced by Leu (L); Tyr (Y) in position 407 has been replaced by Ala (A); Arg (R) in position 409 has been replaced by Ala (A).

26. The antibody of claim 22, wherein the heavy chain has been modified such that the entire hinge has been deleted.

27. The antibody of claim 22, wherein the sequence of said monovalent antibody has been modified so that it does not comprise any acceptor sites for N-linked glycosylation.

28. The antibody of claim 3 or 5, which inhibits the CD38 catalyzed synthesis of cGDPR by at least 25%.

29. The antibody of claim 3 or 5, which inhibits the CD38 catalyzed synthesis of cADPR by at least 25%.

30. The antibody of claim 3 or 5, which stimulates the hydrolase activity of CD38 by at least 25%.

31. The antibody of claim 3 or 5, which stimulates the NAD hydrolase activity of CD38 by at least 25%.

32. The antibody of claim 3 or 5, which stimulates the cADPR-hydrolase activity of CD38 by at least 25%.

33. The antibody of claim 3 or 5, which inhibits the ability of CD38 to catalyze the formation, via a base-exchange reaction, of NAADP with an IC50 of below 0.5 µg/mL.

34. An antibody drug conjugate comprising the antibody of any one of claims 1, 3, 4, and 5, wherein the antibody is conjugated to a cytotoxic agent, a radioisotope, or a drug.

35. The antibody drug conjugate of claim 34, wherein the antibody is conjugated to an auristatin or a functional peptide analog or derivate thereof via a linker.

36. A bispecific antibody comprising the antibody of any one of claims 1, 3, 4, and 5 and a second binding specificity for a human effector cell or a cancer antigen.

37. The bispecific antibody of claim 36, wherein the second binding specificity is for a human Fc receptor or for a T cell receptor.

38. A composition comprising the antibody of any one of claims 1, 3, 4, and 5.

39. A kit for detecting the presence of CD38 antigen, or a cell expressing CD38, in a sample comprising an anti-CD38 antibody of any one of claims 1, 3, 4, and 5 and instructions for use.

40. A composition comprising the immunoconjugate of claim 34 and a pharmaceutically acceptable carrier.

41. A composition comprising the bispecific antibody of claim 36 and a pharmaceutically acceptable carrier.

42. The antibody of claim 3, wherein the antibody comprises a VH CDR1 having the sequence as set forth in any one of SEQ ID NOs: 3, 8, 13, 18 and 23, a VH CDR2 having the sequence as set forth in any one of SEQ ID NOs: 4, 9, 14, 19 and 24, a VH CDR3 having the sequence as set forth in any one of SEQ ID NOs: 5, 10, 15, 20 and 25, a VL CDR1 having the sequence as set forth in any one of SEQ ID NOs: 28, 33, 38, 43 and 48, a VL CDR2 having the sequence as set forth in any one of SEQ ID NOs: 29, 34, 39, 44 and 49, and a VL CDR3 having the sequence as set forth in any one of SEQ ID NOs: 30, 35, 40, 45 and 50.

43. The antibody of claim 3, wherein the antibody comprises a VH CDR1 having the sequence as set forth in SEQ ID NO: 3, a VH CDR2 having the sequence as set forth in SEQ ID NO: 4, a VH CDR3 having the sequence as set forth in SEQ ID NO: 5, a VL CDR1 having the sequence as set forth in SEQ ID NO: 28, a VL CDR2 having the sequence as set forth in SEQ ID NO: 29, and a VL CDR3 having the sequence as set forth in SEQ ID NO: 30.

44. The antibody of claim 3, wherein the antibody comprises a VH CDR1 having the sequence as set forth in SEQ ID NO: 8, a VH CDR2 having the sequence as set forth in SEQ ID NO: 9, a VH CDR3 having the sequence as set forth in SEQ ID NO: 10, a VL CDR1 having the sequence as set forth in SEQ ID NO: 33, a VL CDR2 having the sequence as set forth in SEQ ID NO: 34, and a VL CDR3 having the sequence as set forth in SEQ ID NO: 35.

45. The antibody of claim 3, wherein the antibody comprises a VH CDR1 having the sequence as set forth in SEQ ID NO: 13, a VH CDR2 having the sequence as set forth in SEQ ID NO: 14, a VH CDR3 having the sequence as set forth in SEQ ID NO: 15, a VL CDR1 having the sequence as set forth in SEQ ID NO: 38, a VL CDR2 having the sequence as set forth in SEQ ID NO: 39, and a VL CDR3 having the sequence as set forth in SEQ ID NO: 40.

46. The antibody of claim 3, wherein the antibody comprises a VH CDR1 having the sequence as set forth in SEQ ID NO: 18, a VH CDR2 having the sequence as set forth in SEQ ID NO: 19, a VH CDR3 having the sequence as set forth in SEQ ID NO: 20, a VL CDR1 having the sequence as set forth in SEQ ID NO: 43, a VL CDR2 having the sequence as set forth in SEQ ID NO: 44, and a VL CDR3 having the sequence as set forth in SEQ ID NO: 45.

47. The antibody of claim 3, wherein the antibody comprises a VH CDR1 having the sequence as set forth in SEQ ID NO: 23, a VH CDR2 having the sequence as set forth in SEQ ID NO: 24, a VH CDR3 having the sequence as set forth in SEQ ID NO: 25, a VL CDR1 having the sequence as set forth in SEQ ID NO 48, a VL CDR2 having the sequence as set forth in SEQ ID NO: 49, and a VL CDR3 having the sequence as set forth in SEQ ID NO: 50.

48. The antibody of claim 5, wherein the antibody comprises a VH region comprising the sequence as set forth in SEQ ID NO: 2, and a VL region comprising the sequence as set forth in SEQ ID NO: 27.

49. The antibody of claim 5, wherein the antibody comprises a VH region comprising the sequence as set forth in SEQ ID NO: 7, and a VL region comprising the sequence as set forth in SEQ ID NO: 32.

50. The antibody of claim 5, wherein the antibody comprises a VH region comprising the sequence as set forth in SEQ ID NO: 12, and a VL region comprising the sequence as set forth in SEQ ID NO: 37.

51. The antibody of claim 5, wherein the antibody comprises a VH region comprising the sequence as set forth in SEQ ID NO: 17, and a VL region comprising the sequence as set forth in SEQ ID NO: 42.

52. The antibody of claim 5, wherein the antibody comprises a VH region comprising the sequence as set forth in SEQ ID NO: 22, and a VL region comprising the sequence as set forth in SEQ ID NO: 47.

* * * * *